US012049486B2

(12) United States Patent
Pisegna et al.

(10) Patent No.: US 12,049,486 B2
(45) Date of Patent: Jul. 30, 2024

(54) PAC1 RECEPTOR AGONISTS (MAXCAPS) AND USES THEREOF

(71) Applicants: The Regents of the University of California, Oakland, CA (US); The United States Government Represented by The Department Of Veterans Affairs, Washington, DC (US)

(72) Inventors: Joseph R. Pisegna, Santa Monica, CA (US); Patrizia M. Germano, Santa Monica, CA (US); John P. Vu, Los Angeles, CA (US)

(73) Assignees: THE REGENTS OF THE UNIVERSITY OF CALIFORNIA, Oakland, CA (US); THE UNITED STATES GOVERNMENT REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 18 days.

(21) Appl. No.: 17/510,090

(22) Filed: Oct. 25, 2021

(65) Prior Publication Data
US 2022/0251162 A1  Aug. 11, 2022

Related U.S. Application Data

(63) Continuation of application No. 16/473,240, filed as application No. PCT/US2018/012405 on Jan. 4, 2018, now Pat. No. 11,186,622.

(60) Provisional application No. 62/442,906, filed on Jan. 5, 2017.

(51) Int. Cl.
| | |
|---|---|
| *C07K 14/575* | (2006.01) |
| *A61K 31/4985* | (2006.01) |
| *A61K 38/22* | (2006.01) |
| *A61K 47/60* | (2017.01) |
| *A61K 47/61* | (2017.01) |
| *A61K 47/65* | (2017.01) |
| *C07K 14/435* | (2006.01) |
| *A61K 38/00* | (2006.01) |

(52) U.S. Cl.
CPC .... *C07K 14/57563* (2013.01); *A61K 31/4985* (2013.01); *A61K 38/2278* (2013.01); *A61K 47/60* (2017.08); *A61K 47/61* (2017.08); *A61K 47/65* (2017.08); *C07K 14/43577* (2013.01); *A61K 38/00* (2013.01); *C07K 2319/00* (2013.01)

(58) Field of Classification Search
CPC .............................................. C07K 14/57563
See application file for complete search history.

(56) References Cited

U.S. PATENT DOCUMENTS

| | | | |
|---|---|---|---|
| 5,480,864 A | 1/1996 | Tajima et al. | |
| 5,637,309 A | 6/1997 | Tajima et al. | |
| 5,763,271 A | 6/1998 | Ribeiro et al. | |
| 6,017,533 A | 1/2000 | Moro et al. | |
| 6,462,016 B1 | 10/2002 | Wakita et al. | |
| 7,928,186 B2 | 4/2011 | Chang | |
| 8,916,517 B2 | 12/2014 | Coy et al. | |
| 11,186,622 B2 | 11/2021 | Pisegna et al. | |
| 2002/0182729 A1 | 12/2002 | DiCicco-Bloom et al. | |
| 2004/0038888 A1 | 2/2004 | Mercer et al. | |
| 2009/0030178 A1 | 1/2009 | Chang | |
| 2011/0268789 A1 | 11/2011 | Li et al. | |
| 2012/0309683 A1 | 12/2012 | Coy et al. | |
| 2015/0104388 A1 | 4/2015 | Coy et al. | |
| 2016/0122406 A1 | 5/2016 | Coy et al. | |
| 2017/0343561 A1 | 11/2017 | May et al. | |
| 2019/0322718 A1 | 10/2019 | Pisegna et al. | |

FOREIGN PATENT DOCUMENTS

| | | |
|---|---|---|
| CA | 2335341 A1 | 2/2000 |
| CA | 2485216 A1 | 11/2003 |
| CN | 101125882 A | 2/2008 |
| CN | 102883739 A | 1/2013 |
| WO | WO-0185100 A2 | 11/2001 |
| WO | WO-03092716 A2 | 11/2003 |
| WO | WO-2018129200 A2 | 7/2018 |

OTHER PUBLICATIONS

Sherwood, Can You Reverse Type 2 Diabetes?, WebMD, https://www.webmd.com/diabetes/can-you-reverse-type-2-diabetes, 2023 (Year: 2023).*
Vu et al., "PACAP intraperitoneal treatment suppresses appetite and food intake via PAC1 receptor in mice by inhibiting ghrelin and increasing GLP-1 and leptin", Am J Physiol Gastrointest Liver Physiol, 2015, G816-G825 (Year: 2015).*
The BetterHealth Channel, "Dry Eye", https://www.betterhealth.vic.gov.au/health/conditionsandtreatments/dry-eye, 2021 (Year: 2021).*
Whelan, "Can IBS Go Away Permanently?"Healthline, https://www.healthline.com/health/irritable-bowel-syndrome/how-to-cure-ibs-permanently#:~:text=There's no cure for IBS,the reduction of flare-ups.2023. (Year: 2023).*

(Continued)

*Primary Examiner* — Lianko G Garyu
(74) *Attorney, Agent, or Firm* — Karen S. Conady; canady + lortz LLP

(57) ABSTRACT

In certain embodiments novel PAC1 receptor agonists are provided wherein the agonists comprise a targeting sequence that binds to the PAC1 receptor and said targeting sequence is attached to an amino acid sequence comprising a fragment of the maxadilan amino acid sequence, wherein the targeting sequence comprises a full-length 38 amino acid PACAP peptide or an N-terminus fragment thereof containing the amino acid sequence HSDGIF, wherein said targeting sequence optionally comprises an amino acid insertion between residues 11 and 12 of said PACAP peptide or fragment thereof; and the fragment of the maxadilan amino acid sequence comprises a fragment of the maxadilan sequence effective to activate PAC1 signaling.

16 Claims, 8 Drawing Sheets

Specification includes a Sequence Listing.

(56) References Cited

OTHER PUBLICATIONS

Harmar et al. "Pharmacology and functions of receptors for vasoactive intestinal peptide and pituitary adenylate cyclase-activating polypeptide: IUPHAR Review 1", 2012, Br J Pharmacol 166: 4-17 (Year: 2012).*

Reddy et al. "Functional Analysis of Recombinant Mutants of Maxadilan with a PAC1 Receptor-expressing Melanophore Cell Line", Journal of Biological Chemistry, 2006, pp. 16197-16201 (Year: 2006).*

Sato et al. "Therapeutic peptides: technological advances driving peptides into development", Current Opinion in Biotechnology, 2006, pp. 638-642). (Year: 2006).*

Banki et al. (2014) "The selective PAC1 receptor agonist maxadilan inhibits neurogenic vasodilation and edema formation in the mouse skin," Neuropharmacology, 85: 538-547.

Eggenberger (1999) "Maxadilan interacts with receptors for pituitary adenylyl cyclase activating peptide in human SH-SY5Y and SK-N-MC neuroblastoma cells," Neuropeptides, 32(2): 107-114.

European Extended Search Report dated Jul. 10, 2020 issued in EP 18736163.9.

European Office Action dated Jun. 30, 2021 issued in EP 18736163.9.

Harmar et al. (May 2012) "Pharmacology and functions of receptors for vasoactive intestinal peptide and pituitary adenylate cyclase-activating polypeptide: IUPHAR review 1," Br J Pharmacol. 166: 4-17.

Johns Hopkins Medicine (2021) "Nonalcoholic Fatty Liver Disease", https://www.hopkinsmedicine.org/health; Downloaded 2021 [5 pages].

JP Office Action dated Dec. 6, 2021, in Application No. JP2019-537254 with English translation.

Lerner et al. (2007) "Maxadilan, a PAC1 receptor agonist from sand flies," Peptides 28(9): 1651-1654 [HHS Public Access—Author manuscript—7 pages].

Moro et al. (1999) "Functional characterization of structural alterations in the sequence of the vasodilatory peptide maxadilan yields a pituitary adenylate cyclase-activating peptide type 1 receptor-specific antagonist." J Biol Chem 274:23103-23110.

PCT International Preliminary Report on Patentability dated Jul. 9, 2019 issued in PCT/US2018/012405.

PCT International Search Report and Written Opinion dated Jun. 25, 2018 issued in PCT/US2018/012405.

Pereira et al. (2002) "Maxadilan Activates PAC1 Receptors Expressed in Xenopus laevis Melanophores," Pigment Cell Research, 15(6): 461-466.

Reddy et al. (2008) "Maxadilan, the PAC1 Receptor, and Leishmaniasis," J. Mol. Neurosci. 36(1-3): 241-244.

Reddy, V. B. et al., "Functional Analysis of Recombinant Mutants of Maxadilan with a PAC1 Receptor-expressing Melanophore Cell Line", The Journal of Biological Chemistry, 2006, vol. 281, No. 24, pp. 16197-16201.

Soares et al. (1998) "The Vasoactive Peptide Maxadilan from Sand Fly Saliva Inhibits TNF-a and Induces IL-6 by Mouse Macrophages Through Interaction with the Pituitary Adenylate Cyclase-Activating Polypeptide (PACAP) Receptor," J. Immunol., 160:1811-1816.

Stawikowski et al. (2001) "Introduction to Peptide Synthesis", Current Protocols in Protein Science, 18.1.1-18.1.9 [Supplement 26].

Uchida et al. (1998) "Maxadilan is a Specific Agonist and its Deleted Peptide (M65) is a Specific Antagonist for PACAP Type 1 Receptor," Annals of the New York Academy of Sciences, 865(1): 253-258.

U.S. Final Office Action dated Jun. 14, 2021 issued in U.S. Appl. No. 16/473,240.

U.S. Notice of Allowance dated Jul. 26, 2021 issued in U.S. Appl. No. 16/473,240.

U.S. Office Action dated Feb. 19, 2021 issued in U.S. Appl. No. 16/473,240.

Vaudry et al. (2009) "Pituitary Adenylate Cyclase-Activating Polypeptide and its Receptors: 20 Years after the Discovery," Pharmacol. Rev., 61(3):283-357.

Vu, J. P. et al., "PACAP Intraperitoneal Treatment Suppresses Appetite and Food intake via PAC1 Receptor in Mice by Inhibiting Ghrelin and Increasing GLP-1 and Leptin", American Journal of Physiology. Gastrointestinal and Liver Physiology, 2015, vol. 309, No. 10, pp. G816-G825.

CN Office Action dated Oct. 26, 2022 in Application No. CN201880005836 with English translation.

MX Office Action dated Nov. 23, 2022, in Application No. MX/a/2019/008056 with English translation.

\* cited by examiner

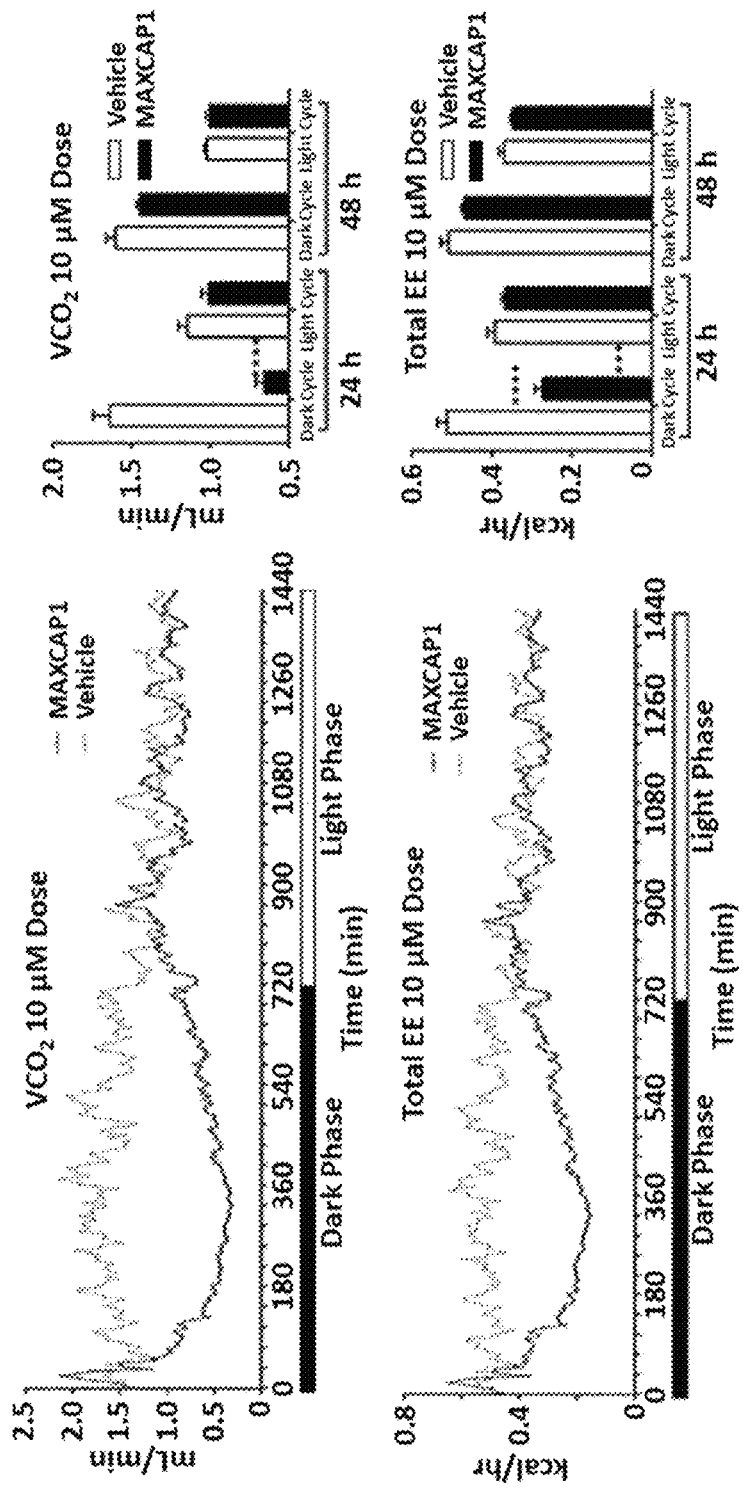
*Fig. 3, cont'd.*

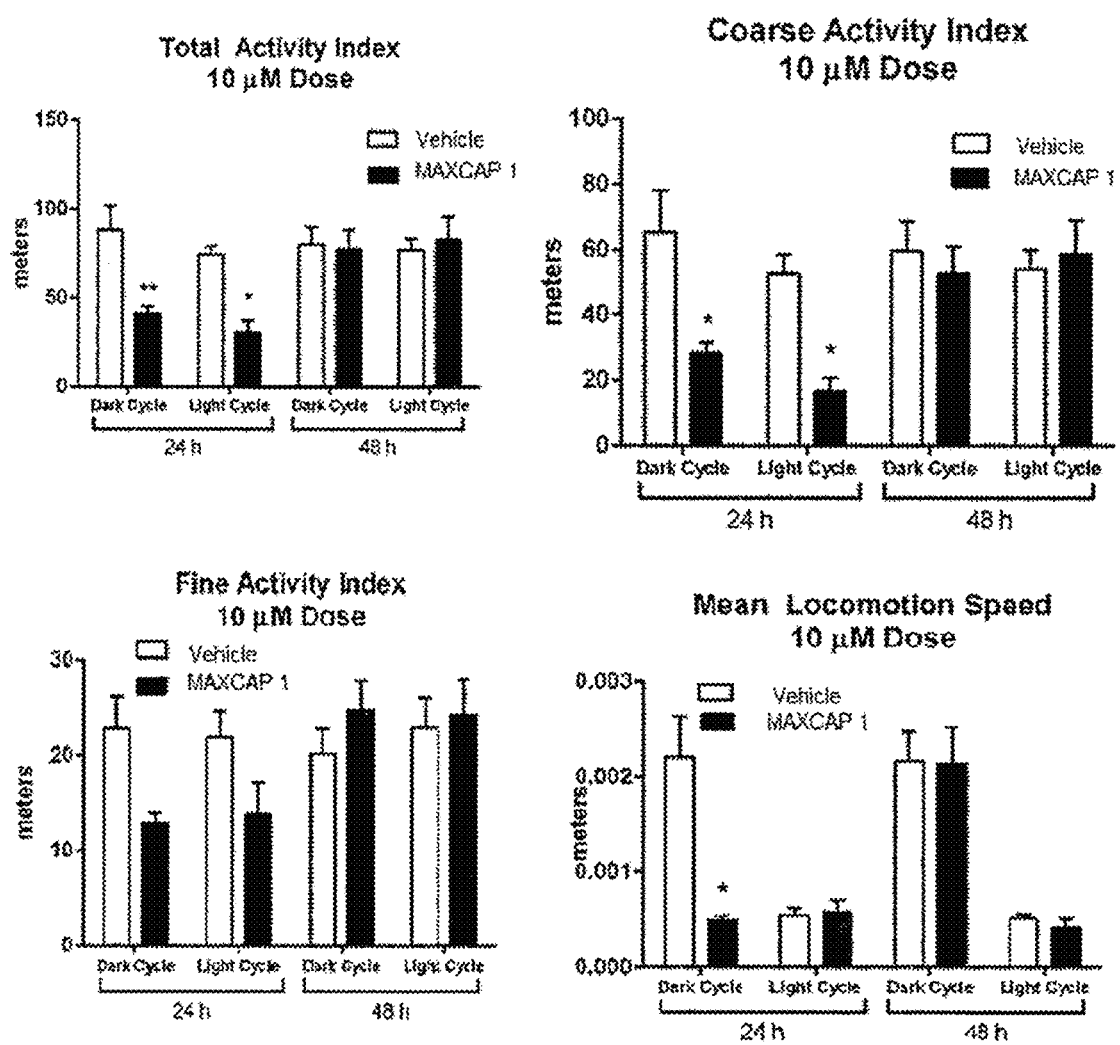
Fig. 3, cont'd.

SEQUENCE LISTING

```
<160> NUMBER OF SEQ ID NOS: 181

<210> SEQ ID NO 1
<211> LENGTH: 61
<212> TYPE: PRT
<213> ORGANISM: Utzomyial ongipalpis

<400> SEQUENCE: 1

Cys Asp Ala Thr Cys Gln Phe Arg Lys Ala Ile Asp Asp Cys Gln Lys
1               5                   10                  15

Gln Ala His His Ser Asn Val Leu Gln Thr Ser Val Gln Thr Thr Ala
            20                  25                  30

Thr Phe Thr Ser Met Asp Thr Ser Gln Leu Pro Gly Asn Ser Val Phe
        35                  40                  45

Lys Glu Cys Met Lys Gln Lys Lys Glu Phe Lys Ala
    50                  55                  60

<210> SEQ ID NO 2
<211> LENGTH: 38
<212> TYPE: PRT
<213> ORGANISM: Homo sapiens

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35
```

<210> SEQ ID NO 3
<211> LENGTH: 27
<212> TYPE: PRT
<213> ORGANISM: Homo sapiens

<400> SEQUENCE: 3

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 4
<211> LENGTH: 21
<212> TYPE: PRT
<213> ORGANISM: Utzomyia longipalpis

<400> SEQUENCE: 4

Pro Gly Asn Ser Val Phe Lys Glu Cys Met Lys Gln Lys Lys Lys Glu
1               5                   10                  15

Phe Lys Ala Gly Lys
            20

<210> SEQ ID NO 5
<211> LENGTH: 49
<212> TYPE: PRT
<213> ORGANISM: Artificial
<220> FEATURE:
<223> OTHER INFORMATION: Synthetic fusion protein

<400> SEQUENCE: 5

His Ser Asp Gly Ile Phe Thr Asp Ser Tyr Ser Arg Tyr Arg Lys
1               5                   10                  15

Gln Met Ala Val Lys Lys Tyr Leu Ala Ala Val Leu Pro Gly Asn Ser
                20                  25                  30

Val Phe Lys Glu Cys Met Lys Gln Lys Lys Lys Glu Phe Lys Ala Gly
            35                  40                  45

Lys

<210> SEQ ID NO 6
<211> LENGTH: 28
<212> TYPE: PRT
<213> ORGANISM: Artificial
<220> FEATURE:
<223> OTHER INFORMATION: Synthetic fusion protein

<400> SEQUENCE: 6

His Ser Asp Gly Ile Phe Ala Pro Gly Asn Ser Val Phe Lys Glu Cys
1               5                   10                  15

Met Lys Gln Lys Lys Lys Glu Phe Lys Ala Gly Lys
            20                  25

<210> SEQ ID NO 7
<211> LENGTH: 35
<212> TYPE: PRT
<213> ORGANISM: Artificial
<220> FEATURE:
<223> OTHER INFORMATION: Synthetic fusion protein

<400> SEQUENCE: 7

His Ser Asp Gly Ile Phe Thr Ser Met Asp Thr Ser Gln Leu Pro Gly
1               5                   10                  15

Asn Ser Val Phe Lys Glu Cys Met Lys Gln Lys Lys Glu Phe Lys
            20                  25                  30

Ala Gly Lys
        35

<210> SEQ ID NO 8
<211> LENGTH: 28
<212> TYPE: PRT
<213> ORGANISM: Artificial
<220> FEATURE:
<223> OTHER INFORMATION: Synthetic fusion protein

<400> SEQUENCE: 8

His Ser Asp Gly Ile Phe Thr Pro Gly Asn Ser Val Phe Lys Glu Cys
1               5                   10                  15

Met Lys Gln Lys Lys Glu Phe Lys Ala Gly Lys
            20                  25

<210> SEQ ID NO 9
<211> LENGTH: 33
<212> TYPE: PRT
<213> ORGANISM: Artificial
<220> FEATURE:
<223> OTHER INFORMATION: Synthetic fusion protein

<400> SEQUENCE: 9

His Ser Asp Gly Ile Phe Thr Asp Ser Tyr Ser Ala Pro Gly Asn Ser
1               5                   10                  15

Val Phe Lys Glu Cys Met Lys Gln Lys Lys Glu Phe Lys Ala Gly
            20                  25                  30

Lys

<210> SEQ ID NO 10
<211> LENGTH: 33
<212> TYPE: PRT
<213> ORGANISM: Artificial
<220> FEATURE:
<223> OTHER INFORMATION: Synthetic fusion protein

<400> SEQUENCE: 10

His Ser Asp Gly Ile Phe Thr Asp Ser Tyr Ser Lys Pro Gly Asn Ser
1               5                   10                  15

Val Phe Lys Glu Cys Met Lys Gln Lys Lys Glu Phe Lys Ala Gly
            20                  25                  30

Lys

<210> SEQ ID NO 11
<211> LENGTH: 36
<212> TYPE: PRT
<213> ORGANISM: Artificial
<220> FEATURE:
<223> OTHER INFORMATION: Synthetic fusion protein

<400> SEQUENCE: 11

His Ser Asp Gly Ile Phe Thr Asp Ser Tyr Ser Arg Tyr Arg Ala Pro
1               5                   10                  15

Gly Asn Ser Val Phe Lys Glu Cys Met Lys Gln Lys Lys Glu Phe
            20                  25                  30

Lys Ala Gly Lys
        35

```
<210> SEQ ID NO 12
<211> LENGTH: 36
<212> TYPE: PRT
<213> ORGANISM: Artificial
<220> FEATURE:
<223> OTHER INFORMATION: Synthetic fusion protein

<400> SEQUENCE: 12

His Ser Asp Gly Ile Phe Thr Asp Ser Tyr Ser Arg Tyr Arg Lys Pro
1               5                   10                  15

Gly Asn Ser Val Phe Lys Glu Cys Met Lys Gln Lys Lys Lys Glu Phe
            20                  25                  30

Lys Ala Gly Lys
        35

<210> SEQ ID NO 13
<211> LENGTH: 31
<212> TYPE: PRT
<213> ORGANISM: Artificial
<220> FEATURE:
<223> OTHER INFORMATION: Synthetic fusion protein

<400> SEQUENCE: 13

Thr Ala Thr Phe Thr Ser Met Asp Thr Ser Gln Leu Pro Gly Asn Ser
1               5                   10                  15

Val Phe Lys Glu Cys Met Lys Gln Lys Lys Lys Glu Phe Lys Ala
            20                  25                  30

<210> SEQ ID NO 14
<211> LENGTH: 30
<212> TYPE: PRT
<213> ORGANISM: Artificial
<220> FEATURE:
<223> OTHER INFORMATION: Synthetic fusion protein

<400> SEQUENCE: 14

Ala Thr Phe Thr Ser Met Asp Thr Ser Gln Leu Pro Gly Asn Ser Val
1               5                   10                  15

Phe Lys Glu Cys Met Lys Gln Lys Lys Lys Glu Phe Lys Ala
            20                  25                  30

<210> SEQ ID NO 15
<211> LENGTH: 29
<212> TYPE: PRT
<213> ORGANISM: Artificial
<220> FEATURE:
<223> OTHER INFORMATION: Synthetic fusion protein

<400> SEQUENCE: 15

Thr Phe Thr Ser Met Asp Thr Ser Gln Leu Pro Gly Asn Ser Val Phe
1               5                   10                  15

Lys Glu Cys Met Lys Gln Lys Lys Lys Glu Phe Lys Ala
            20                  25

<210> SEQ ID NO 16
<211> LENGTH: 28
<212> TYPE: PRT
<213> ORGANISM: Artificial
<220> FEATURE:
<223> OTHER INFORMATION: Synthetic fusion protein

<400> SEQUENCE: 16

Phe Thr Ser Met Asp Thr Ser Gln Leu Pro Gly Asn Ser Val Phe Lys
1               5                   10                  15
```

Glu Cys Met Lys Gln Lys Lys Lys Glu Phe Lys Ala
            20                  25

<210> SEQ ID NO 17
<211> LENGTH: 27
<212> TYPE: PRT
<213> ORGANISM: Artificial
<220> FEATURE:
<223> OTHER INFORMATION: Synthetic fusion protein

<400> SEQUENCE: 17

Thr Ser Met Asp Thr Ser Gln Leu Pro Gly Asn Ser Val Phe Lys Glu
1               5                   10                  15

Cys Met Lys Gln Lys Lys Lys Glu Phe Lys Ala
            20                  25

<210> SEQ ID NO 18
<211> LENGTH: 26
<212> TYPE: PRT
<213> ORGANISM: Artificial
<220> FEATURE:
<223> OTHER INFORMATION: Synthetic fusion protein

<400> SEQUENCE: 18

Ser Met Asp Thr Ser Gln Leu Pro Gly Asn Ser Val Phe Lys Glu Cys
1               5                   10                  15

Met Lys Gln Lys Lys Lys Glu Phe Lys Ala
            20                  25

<210> SEQ ID NO 19
<211> LENGTH: 25
<212> TYPE: PRT
<213> ORGANISM: Artificial
<220> FEATURE:
<223> OTHER INFORMATION: Synthetic fusion protein

<400> SEQUENCE: 19

Met Asp Thr Ser Gln Leu Pro Gly Asn Ser Val Phe Lys Glu Cys Met
1               5                   10                  15

Lys Gln Lys Lys Lys Glu Phe Lys Ala
            20                  25

<210> SEQ ID NO 20
<211> LENGTH: 24
<212> TYPE: PRT
<213> ORGANISM: Artificial
<220> FEATURE:
<223> OTHER INFORMATION: Synthetic fusion protein

<400> SEQUENCE: 20

Asp Thr Ser Gln Leu Pro Gly Asn Ser Val Phe Lys Glu Cys Met Lys
1               5                   10                  15

Gln Lys Lys Lys Glu Phe Lys Ala
            20

<210> SEQ ID NO 21
<211> LENGTH: 23
<212> TYPE: PRT
<213> ORGANISM: Artificial
<220> FEATURE:
<223> OTHER INFORMATION: Synthetic fusion protein

<400> SEQUENCE: 21

Thr Ser Gln Leu Pro Gly Asn Ser Val Phe Lys Glu Cys Met Lys Gln
1               5                   10                  15

-continued

Lys Lys Lys Glu Phe Lys Ala
            20

<210> SEQ ID NO 22
<211> LENGTH: 22
<212> TYPE: PRT
<213> ORGANISM: Artificial
<220> FEATURE:
<223> OTHER INFORMATION: Synthetic fusion protein

<400> SEQUENCE: 22

Ser Gln Leu Pro Gly Asn Ser Val Phe Lys Glu Cys Met Lys Gln Lys
1               5                   10                  15

Lys Lys Glu Phe Lys Ala
            20

<210> SEQ ID NO 23
<211> LENGTH: 21
<212> TYPE: PRT
<213> ORGANISM: Artificial
<220> FEATURE:
<223> OTHER INFORMATION: Synthetic fusion protein

<400> SEQUENCE: 23

Gln Leu Pro Gly Asn Ser Val Phe Lys Glu Cys Met Lys Gln Lys Lys
1               5                   10                  15

Lys Glu Phe Lys Ala
            20

<210> SEQ ID NO 24
<211> LENGTH: 20
<212> TYPE: PRT
<213> ORGANISM: Artificial
<220> FEATURE:
<223> OTHER INFORMATION: Synthetic fusion protein

<400> SEQUENCE: 24

Leu Pro Gly Asn Ser Val Phe Lys Glu Cys Met Lys Gln Lys Lys Lys
1               5                   10                  15

Glu Phe Lys Ala
            20

<210> SEQ ID NO 25
<211> LENGTH: 19
<212> TYPE: PRT
<213> ORGANISM: Artificial
<220> FEATURE:
<223> OTHER INFORMATION: Synthetic fusion protein

<400> SEQUENCE: 25

Pro Gly Asn Ser Val Phe Lys Glu Cys Met Lys Gln Lys Lys Lys Glu
1               5                   10                  15

Phe Lys Ala

<210> SEQ ID NO 26
<211> LENGTH: 86
<212> TYPE: PRT
<213> ORGANISM: Artificial
<220> FEATURE:
<223> OTHER INFORMATION: Synthetic fusion protein

<400> SEQUENCE: 26

Met Lys Gln Ile Leu Leu Ile Ser Leu Val Val Val Leu Ala Val Phe
1               5                   10                  15

```
Ala Phe Asn Val Ala Glu Gly Cys Asp Ala Thr Cys Gln Phe Arg Lys
             20                  25                  30

Ala Ile Asp Asp Cys Gln Lys Gln Ala His His Ser Asn Val Leu Gln
         35                  40                  45

Thr Ser Val Gln Thr Thr Ala Thr Phe Thr Ser Met Asp Thr Ser Gln
     50                  55                  60

Leu Pro Gly Asn Ser Val Phe Lys Glu Cys Met Lys Gln Lys Lys Lys
65                  70                  75                  80

Glu Phe Ser Ser Gly Lys
                 85

<210> SEQ ID NO 27
<211> LENGTH: 85
<212> TYPE: PRT
<213> ORGANISM: Artificial
<220> FEATURE:
<223> OTHER INFORMATION: Synthetic fusion protein

<400> SEQUENCE: 27

Lys Gln Ile Leu Leu Ile Ser Leu Val Val Val Leu Ala Val Phe Ala
1               5                   10                  15

Phe Asn Val Ala Glu Gly Cys Asp Ala Thr Cys Gln Phe Arg Lys Ala
             20                  25                  30

Ile Asp Asp Cys Gln Lys Gln Ala His His Ser Asn Val Leu Gln Thr
         35                  40                  45

Ser Val Gln Thr Thr Ala Thr Phe Thr Ser Met Asp Thr Ser Gln Leu
     50                  55                  60

Pro Gly Asn Ser Val Phe Lys Glu Cys Met Lys Gln Lys Lys Lys Glu
65                  70                  75                  80

Phe Ser Ser Gly Lys
                 85

<210> SEQ ID NO 28
<211> LENGTH: 84
<212> TYPE: PRT
<213> ORGANISM: Artificial
<220> FEATURE:
<223> OTHER INFORMATION: Synthetic fusion protein

<400> SEQUENCE: 28

Gln Ile Leu Leu Ile Ser Leu Val Val Val Leu Ala Val Phe Ala Phe
1               5                   10                  15

Asn Val Ala Glu Gly Cys Asp Ala Thr Cys Gln Phe Arg Lys Ala Ile
             20                  25                  30

Asp Asp Cys Gln Lys Gln Ala His His Ser Asn Val Leu Gln Thr Ser
         35                  40                  45

Val Gln Thr Thr Ala Thr Phe Thr Ser Met Asp Thr Ser Gln Leu Pro
     50                  55                  60

Gly Asn Ser Val Phe Lys Glu Cys Met Lys Gln Lys Lys Lys Glu Phe
65                  70                  75                  80

Ser Ser Gly Lys

<210> SEQ ID NO 29
<211> LENGTH: 83
<212> TYPE: PRT
<213> ORGANISM: Artificial
<220> FEATURE:
<223> OTHER INFORMATION: Synthetic fusion protein
```

<400> SEQUENCE: 29

Ile Leu Ile Ser Leu Val Val Leu Ala Val Phe Ala Phe Asn
1               5                   10                  15

Val Ala Glu Gly Cys Asp Ala Thr Cys Gln Phe Arg Lys Ala Ile Asp
            20                  25                  30

Asp Cys Gln Lys Gln Ala His His Ser Asn Val Leu Gln Thr Ser Val
                35                  40                  45

Gln Thr Thr Ala Thr Phe Thr Ser Met Asp Thr Ser Gln Leu Pro Gly
    50                  55                  60

Asn Ser Val Phe Lys Glu Cys Met Lys Gln Lys Lys Glu Phe Ser
65                  70                  75                  80

Ser Gly Lys

<210> SEQ ID NO 30
<211> LENGTH: 82
<212> TYPE: PRT
<213> ORGANISM: Artificial
<220> FEATURE:
<223> OTHER INFORMATION: Synthetic fusion protein

<400> SEQUENCE: 30

Leu Leu Ile Ser Leu Val Val Leu Ala Val Phe Ala Phe Asn Val
1               5                   10                  15

Ala Glu Gly Cys Asp Ala Thr Cys Gln Phe Arg Lys Ala Ile Asp Asp
            20                  25                  30

Cys Gln Lys Gln Ala His His Ser Asn Val Leu Gln Thr Ser Val Gln
                35                  40                  45

Thr Thr Ala Thr Phe Thr Ser Met Asp Thr Ser Gln Leu Pro Gly Asn
    50                  55                  60

Ser Val Phe Lys Glu Cys Met Lys Gln Lys Lys Glu Phe Ser Ser
65                  70                  75                  80

Gly Lys

<210> SEQ ID NO 31
<211> LENGTH: 81
<212> TYPE: PRT
<213> ORGANISM: Artificial
<220> FEATURE:
<223> OTHER INFORMATION: Synthetic fusion protein

<400> SEQUENCE: 31

Leu Ile Ser Leu Val Val Leu Ala Val Phe Ala Phe Asn Val Ala
1               5                   10                  15

Glu Gly Cys Asp Ala Thr Cys Gln Phe Arg Lys Ala Ile Asp Asp Cys
            20                  25                  30

Gln Lys Gln Ala His His Ser Asn Val Leu Gln Thr Ser Val Gln Thr
                35                  40                  45

Thr Ala Thr Phe Thr Ser Met Asp Thr Ser Gln Leu Pro Gly Asn Ser
    50                  55                  60

Val Phe Lys Glu Cys Met Lys Gln Lys Lys Glu Phe Ser Ser Gly
65                  70                  75                  80

Lys

<210> SEQ ID NO 32
<211> LENGTH: 80
<212> TYPE: PRT
<213> ORGANISM: Artificial
<220> FEATURE:

<223> OTHER INFORMATION: Synthetic fusion protein

<400> SEQUENCE: 32

```
Ile Ser Leu Val Val Leu Ala Val Phe Ala Phe Asn Val Ala Glu
1               5                   10                  15
Gly Cys Asp Ala Thr Cys Gln Phe Arg Lys Ala Ile Asp Asp Cys Gln
                20                  25                  30
Lys Gln Ala His His Ser Asn Val Leu Gln Thr Ser Val Gln Thr Thr
            35                  40                  45
Ala Thr Phe Thr Ser Met Asp Thr Ser Gln Leu Pro Gly Asn Ser Val
        50                  55                  60
Phe Lys Glu Cys Met Lys Gln Lys Lys Glu Phe Ser Ser Gly Lys
65                  70                  75                  80
```

<210> SEQ ID NO 33
<211> LENGTH: 79
<212> TYPE: PRT
<213> ORGANISM: Artificial
<220> FEATURE:
<223> OTHER INFORMATION: Synthetic fusion protein

<400> SEQUENCE: 33

```
Ser Leu Val Val Val Leu Ala Val Phe Ala Phe Asn Val Ala Glu Gly
1               5                   10                  15
Cys Asp Ala Thr Cys Gln Phe Arg Lys Ala Ile Asp Asp Cys Gln Lys
                20                  25                  30
Gln Ala His His Ser Asn Val Leu Gln Thr Ser Val Gln Thr Thr Ala
            35                  40                  45
Thr Phe Thr Ser Met Asp Thr Ser Gln Leu Pro Gly Asn Ser Val Phe
        50                  55                  60
Lys Glu Cys Met Lys Gln Lys Lys Glu Phe Ser Ser Gly Lys
65                  70                  75
```

<210> SEQ ID NO 34
<211> LENGTH: 78
<212> TYPE: PRT
<213> ORGANISM: Artificial
<220> FEATURE:
<223> OTHER INFORMATION: Synthetic fusion protein

<400> SEQUENCE: 34

```
Leu Val Val Val Leu Ala Val Phe Ala Phe Asn Val Ala Glu Gly Cys
1               5                   10                  15
Asp Ala Thr Cys Gln Phe Arg Lys Ala Ile Asp Asp Cys Gln Lys Gln
                20                  25                  30
Ala His His Ser Asn Val Leu Gln Thr Ser Val Gln Thr Thr Ala Thr
            35                  40                  45
Phe Thr Ser Met Asp Thr Ser Gln Leu Pro Gly Asn Ser Val Phe Lys
        50                  55                  60
Glu Cys Met Lys Gln Lys Lys Glu Phe Ser Ser Gly Lys
65                  70                  75
```

<210> SEQ ID NO 35
<211> LENGTH: 77
<212> TYPE: PRT
<213> ORGANISM: Artificial
<220> FEATURE:
<223> OTHER INFORMATION: Synthetic fusion protein

<400> SEQUENCE: 35

Val Val Val Leu Ala Val Phe Ala Phe Asn Val Ala Glu Gly Cys Asp
1               5                   10                  15

Ala Thr Cys Gln Phe Arg Lys Ala Ile Asp Asp Cys Gln Lys Gln Ala
            20                  25                  30

His His Ser Asn Val Leu Gln Thr Ser Val Gln Thr Thr Ala Thr Phe
        35                  40                  45

Thr Ser Met Asp Thr Ser Gln Leu Pro Gly Asn Ser Val Phe Lys Glu
    50                  55                  60

Cys Met Lys Gln Lys Lys Lys Glu Phe Ser Ser Gly Lys
65                  70                  75

<210> SEQ ID NO 36
<211> LENGTH: 76
<212> TYPE: PRT
<213> ORGANISM: Artificial
<220> FEATURE:
<223> OTHER INFORMATION: Synthetic fusion protein

<400> SEQUENCE: 36

Val Val Leu Ala Val Phe Ala Phe Asn Val Ala Glu Gly Cys Asp Ala
1               5                   10                  15

Thr Cys Gln Phe Arg Lys Ala Ile Asp Asp Cys Gln Lys Gln Ala His
            20                  25                  30

His Ser Asn Val Leu Gln Thr Ser Val Gln Thr Thr Ala Thr Phe Thr
        35                  40                  45

Ser Met Asp Thr Ser Gln Leu Pro Gly Asn Ser Val Phe Lys Glu Cys
    50                  55                  60

Met Lys Gln Lys Lys Lys Glu Phe Ser Ser Gly Lys
65                  70                  75

<210> SEQ ID NO 37
<211> LENGTH: 75
<212> TYPE: PRT
<213> ORGANISM: Artificial
<220> FEATURE:
<223> OTHER INFORMATION: Synthetic fusion protein

<400> SEQUENCE: 37

Val Leu Ala Val Phe Ala Phe Asn Val Ala Glu Gly Cys Asp Ala Thr
1               5                   10                  15

Cys Gln Phe Arg Lys Ala Ile Asp Asp Cys Gln Lys Gln Ala His His
            20                  25                  30

Ser Asn Val Leu Gln Thr Ser Val Gln Thr Thr Ala Thr Phe Thr Ser
        35                  40                  45

Met Asp Thr Ser Gln Leu Pro Gly Asn Ser Val Phe Lys Glu Cys Met
    50                  55                  60

Lys Gln Lys Lys Lys Glu Phe Ser Ser Gly Lys
65                  70                  75

<210> SEQ ID NO 38
<211> LENGTH: 74
<212> TYPE: PRT
<213> ORGANISM: Artificial
<220> FEATURE:
<223> OTHER INFORMATION: Synthetic fusion protein

<400> SEQUENCE: 38

Leu Ala Val Phe Ala Phe Asn Val Ala Glu Gly Cys Asp Ala Thr Cys
1               5                   10                  15

Gln Phe Arg Lys Ala Ile Asp Asp Cys Gln Lys Gln Ala His His Ser
            20                  25                  30

Asn Val Leu Gln Thr Ser Val Gln Thr Thr Ala Thr Phe Thr Ser Met
        35                  40                  45

Asp Thr Ser Gln Leu Pro Gly Asn Ser Val Phe Lys Glu Cys Met Lys
    50                  55                  60

Gln Lys Lys Lys Glu Phe Ser Ser Gly Lys
65                  70

<210> SEQ ID NO 39
<211> LENGTH: 73
<212> TYPE: PRT
<213> ORGANISM: Artificial
<220> FEATURE:
<223> OTHER INFORMATION: Synthetic fusion protein

<400> SEQUENCE: 39

Ala Val Phe Ala Phe Asn Val Ala Glu Gly Cys Asp Ala Thr Cys Gln
1               5                   10                  15

Phe Arg Lys Ala Ile Asp Asp Cys Gln Lys Gln Ala His His Ser Asn
            20                  25                  30

Val Leu Gln Thr Ser Val Gln Thr Thr Ala Thr Phe Thr Ser Met Asp
        35                  40                  45

Thr Ser Gln Leu Pro Gly Asn Ser Val Phe Lys Glu Cys Met Lys Gln
    50                  55                  60

Lys Lys Lys Glu Phe Ser Ser Gly Lys
65                  70

<210> SEQ ID NO 40
<211> LENGTH: 72
<212> TYPE: PRT
<213> ORGANISM: Artificial
<220> FEATURE:
<223> OTHER INFORMATION: Synthetic fusion protein

<400> SEQUENCE: 40

Val Phe Ala Phe Asn Val Ala Glu Gly Cys Asp Ala Thr Cys Gln Phe
1               5                   10                  15

Arg Lys Ala Ile Asp Asp Cys Gln Lys Gln Ala His His Ser Asn Val
            20                  25                  30

Leu Gln Thr Ser Val Gln Thr Thr Ala Thr Phe Thr Ser Met Asp Thr
        35                  40                  45

Ser Gln Leu Pro Gly Asn Ser Val Phe Lys Glu Cys Met Lys Gln Lys
    50                  55                  60

Lys Lys Glu Phe Ser Ser Gly Lys
65                  70

<210> SEQ ID NO 41
<211> LENGTH: 71
<212> TYPE: PRT
<213> ORGANISM: Artificial
<220> FEATURE:
<223> OTHER INFORMATION: Synthetic fusion protein

<400> SEQUENCE: 41

Phe Ala Phe Asn Val Ala Glu Gly Cys Asp Ala Thr Cys Gln Phe Arg
1               5                   10                  15

Lys Ala Ile Asp Asp Cys Gln Lys Gln Ala His His Ser Asn Val Leu
            20                  25                  30

Gln Thr Ser Val Gln Thr Thr Ala Thr Phe Thr Ser Met Asp Thr Ser
        35                  40                  45

Gln Leu Pro Gly Asn Ser Val Phe Lys Glu Cys Met Lys Gln Lys Lys
    50                  55                  60

Lys Glu Phe Ser Ser Gly Lys
65                  70

<210> SEQ ID NO 42
<211> LENGTH: 70
<212> TYPE: PRT
<213> ORGANISM: Artificial
<220> FEATURE:
<223> OTHER INFORMATION: Synthetic fusion protein

<400> SEQUENCE: 42

Ala Phe Asn Val Ala Glu Gly Cys Asp Ala Thr Cys Gln Phe Arg Lys
1               5                   10                  15

Ala Ile Asp Asp Cys Gln Lys Gln Ala His His Ser Asn Val Leu Gln
            20                  25                  30

Thr Ser Val Gln Thr Thr Ala Thr Phe Thr Ser Met Asp Thr Ser Gln
        35                  40                  45

Leu Pro Gly Asn Ser Val Phe Lys Glu Cys Met Lys Gln Lys Lys Lys
    50                  55                  60

Glu Phe Ser Ser Gly Lys
65                  70

<210> SEQ ID NO 43
<211> LENGTH: 69
<212> TYPE: PRT
<213> ORGANISM: Artificial
<220> FEATURE:
<223> OTHER INFORMATION: Synthetic fusion protein

<400> SEQUENCE: 43

Phe Asn Val Ala Glu Gly Cys Asp Ala Thr Cys Gln Phe Arg Lys Ala
1               5                   10                  15

Ile Asp Asp Cys Gln Lys Gln Ala His His Ser Asn Val Leu Gln Thr
            20                  25                  30

Ser Val Gln Thr Thr Ala Thr Phe Thr Ser Met Asp Thr Ser Gln Leu
        35                  40                  45

Pro Gly Asn Ser Val Phe Lys Glu Cys Met Lys Gln Lys Lys Lys Glu
    50                  55                  60

Phe Ser Ser Gly Lys
65

<210> SEQ ID NO 44
<211> LENGTH: 68
<212> TYPE: PRT
<213> ORGANISM: Artificial
<220> FEATURE:
<223> OTHER INFORMATION: Synthetic fusion protein -continued

```
<400> SEQUENCE: 44

Asn Val Ala Glu Gly Cys Asp Ala Thr Cys Gln Phe Arg Lys Ala Ile
1               5                   10                  15

Asp Asp Cys Gln Lys Gln Ala His His Ser Asn Val Leu Gln Thr Ser
            20                  25                  30

Val Gln Thr Thr Ala Thr Phe Thr Ser Met Asp Thr Ser Gln Leu Pro
        35                  40                  45

Gly Asn Ser Val Phe Lys Glu Cys Met Lys Gln Lys Lys Lys Glu Phe
50                  55                  60

Ser Ser Gly Lys
65

<210> SEQ ID NO 45
<211> LENGTH: 67
<212> TYPE: PRT
<213> ORGANISM: Artificial
<220> FEATURE:
<223> OTHER INFORMATION: Synthetic fusion protein

<400> SEQUENCE: 45

Val Ala Glu Gly Cys Asp Ala Thr Cys Gln Phe Arg Lys Ala Ile Asp
1               5                   10                  15

Asp Cys Gln Lys Gln Ala His His Ser Asn Val Leu Gln Thr Ser Val
            20                  25                  30

Gln Thr Thr Ala Thr Phe Thr Ser Met Asp Thr Ser Gln Leu Pro Gly
        35                  40                  45

Asn Ser Val Phe Lys Glu Cys Met Lys Gln Lys Lys Lys Glu Phe Ser
50                  55                  60

Ser Gly Lys
65

<210> SEQ ID NO 46
<211> LENGTH: 66
<212> TYPE: PRT
<213> ORGANISM: Artificial
<220> FEATURE:
<223> OTHER INFORMATION: Synthetic fusion protein

<400> SEQUENCE: 46

Ala Glu Gly Cys Asp Ala Thr Cys Gln Phe Arg Lys Ala Ile Asp Asp
1               5                   10                  15

Cys Gln Lys Gln Ala His His Ser Asn Val Leu Gln Thr Ser Val Gln
            20                  25                  30

Thr Thr Ala Thr Phe Thr Ser Met Asp Thr Ser Gln Leu Pro Gly Asn
        35                  40                  45

Ser Val Phe Lys Glu Cys Met Lys Gln Lys Lys Lys Glu Phe Ser Ser
50                  55                  60

Gly Lys
65

<210> SEQ ID NO 47
<211> LENGTH: 65
<212> TYPE: PRT
<213> ORGANISM: Artificial
<220> FEATURE:
<223> OTHER INFORMATION: Synthetic fusion protein

<400> SEQUENCE: 47

Glu Gly Cys Asp Ala Thr Cys Gln Phe Arg Lys Ala Ile Asp Asp Cys
1               5                   10                  15
```

Gln Lys Gln Ala His His Ser Asn Val Leu Gln Thr Ser Val Gln Thr
              20                  25                  30

Thr Ala Thr Phe Thr Ser Met Asp Thr Ser Gln Leu Pro Gly Asn Ser
          35                  40                  45

Val Phe Lys Glu Cys Met Lys Gln Lys Lys Glu Phe Ser Ser Gly
 50                  55                  60

Lys
65

<210> SEQ ID NO 48
<211> LENGTH: 64
<212> TYPE: PRT
<213> ORGANISM: Artificial
<220> FEATURE:
<223> OTHER INFORMATION: Synthetic fusion protein

<400> SEQUENCE: 48

Gly Cys Asp Ala Thr Cys Gln Phe Arg Lys Ala Ile Asp Asp Cys Gln
1               5                   10                  15

Lys Gln Ala His His Ser Asn Val Leu Gln Thr Ser Val Gln Thr Thr
              20                  25                  30

Ala Thr Phe Thr Ser Met Asp Thr Ser Gln Leu Pro Gly Asn Ser Val
          35                  40                  45

Phe Lys Glu Cys Met Lys Gln Lys Lys Glu Phe Ser Ser Gly Lys
 50                  55                  60

<210> SEQ ID NO 49
<211> LENGTH: 63
<212> TYPE: PRT
<213> ORGANISM: Artificial
<220> FEATURE:
<223> OTHER INFORMATION: Synthetic fusion protein

<400> SEQUENCE: 49

Cys Asp Ala Thr Cys Gln Phe Arg Lys Ala Ile Asp Asp Cys Gln Lys
1               5                   10                  15

Gln Ala His His Ser Asn Val Leu Gln Thr Ser Val Gln Thr Thr Ala
              20                  25                  30

Thr Phe Thr Ser Met Asp Thr Ser Gln Leu Pro Gly Asn Ser Val Phe
          35                  40                  45

Lys Glu Cys Met Lys Gln Lys Lys Glu Phe Ser Ser Gly Lys
 50                  55                  60

<210> SEQ ID NO 50
<211> LENGTH: 62
<212> TYPE: PRT
<213> ORGANISM: Artificial
<220> FEATURE:
<223> OTHER INFORMATION: Synthetic fusion protein

<400> SEQUENCE: 50

Asp Ala Thr Cys Gln Phe Arg Lys Ala Ile Asp Asp Cys Gln Lys Gln
1               5                   10                  15

Ala His His Ser Asn Val Leu Gln Thr Ser Val Gln Thr Thr Ala Thr
              20                  25                  30

Phe Thr Ser Met Asp Thr Ser Gln Leu Pro Gly Asn Ser Val Phe Lys
          35                  40                  45

Glu Cys Met Lys Gln Lys Lys Glu Phe Ser Ser Gly Lys
 50                  55                  60

```
<210> SEQ ID NO 51
<211> LENGTH: 61
<212> TYPE: PRT
<213> ORGANISM: Artificial
<220> FEATURE:
<223> OTHER INFORMATION: Synthetic fusion protein

<400> SEQUENCE: 51

Ala Thr Cys Gln Phe Arg Lys Ala Ile Asp Asp Cys Gln Lys Gln Ala
1               5                   10                  15

His His Ser Asn Val Leu Gln Thr Ser Val Gln Thr Thr Ala Thr Phe
            20                  25                  30

Thr Ser Met Asp Thr Ser Gln Leu Pro Gly Asn Ser Val Phe Lys Glu
        35                  40                  45

Cys Met Lys Gln Lys Lys Lys Glu Phe Ser Ser Gly Lys
    50                  55                  60

<210> SEQ ID NO 52
<211> LENGTH: 60
<212> TYPE: PRT
<213> ORGANISM: Artificial
<220> FEATURE:
<223> OTHER INFORMATION: Synthetic fusion protein

<400> SEQUENCE: 52

Thr Cys Gln Phe Arg Lys Ala Ile Asp Asp Cys Gln Lys Gln Ala His
1               5                   10                  15

His Ser Asn Val Leu Gln Thr Ser Val Gln Thr Thr Ala Thr Phe Thr
            20                  25                  30

Ser Met Asp Thr Ser Gln Leu Pro Gly Asn Ser Val Phe Lys Glu Cys
        35                  40                  45

Met Lys Gln Lys Lys Lys Glu Phe Ser Ser Gly Lys
    50                  55                  60

<210> SEQ ID NO 53
<211> LENGTH: 59
<212> TYPE: PRT
<213> ORGANISM: Artificial
<220> FEATURE:
<223> OTHER INFORMATION: Synthetic fusion protein

<400> SEQUENCE: 53

Cys Gln Phe Arg Lys Ala Ile Asp Asp Cys Gln Lys Gln Ala His His
1               5                   10                  15

Ser Asn Val Leu Gln Thr Ser Val Gln Thr Thr Ala Thr Phe Thr Ser
            20                  25                  30

Met Asp Thr Ser Gln Leu Pro Gly Asn Ser Val Phe Lys Glu Cys Met
        35                  40                  45

Lys Gln Lys Lys Lys Glu Phe Ser Ser Gly Lys
    50                  55

<210> SEQ ID NO 54
<211> LENGTH: 58
<212> TYPE: PRT
<213> ORGANISM: Artificial
<220> FEATURE:
<223> OTHER INFORMATION: Synthetic fusion protein

<400> SEQUENCE: 54

Gln Phe Arg Lys Ala Ile Asp Asp Cys Gln Lys Gln Ala His His Ser
1               5                   10                  15
```

```
Asn Val Leu Gln Thr Ser Val Gln Thr Thr Ala Thr Phe Thr Ser Met
             20                  25                  30

Asp Thr Ser Gln Leu Pro Gly Asn Ser Val Phe Lys Glu Cys Met Lys
         35                  40                  45

Gln Lys Lys Lys Glu Phe Ser Ser Gly Lys
     50                  55

<210> SEQ ID NO 55
<211> LENGTH: 57
<212> TYPE: PRT
<213> ORGANISM: Artificial
<220> FEATURE:
<223> OTHER INFORMATION: Synthetic fusion protein

<400> SEQUENCE: 55

Phe Arg Lys Ala Ile Asp Asp Cys Gln Lys Gln Ala His His Ser Asn
1               5                   10                  15

Val Leu Gln Thr Ser Val Gln Thr Thr Ala Thr Phe Thr Ser Met Asp
             20                  25                  30

Thr Ser Gln Leu Pro Gly Asn Ser Val Phe Lys Glu Cys Met Lys Gln
         35                  40                  45

Lys Lys Lys Glu Phe Ser Ser Gly Lys
     50                  55

<210> SEQ ID NO 56
<211> LENGTH: 56
<212> TYPE: PRT
<213> ORGANISM: Artificial
<220> FEATURE:
<223> OTHER INFORMATION: Synthetic fusion protein

<400> SEQUENCE: 56

Arg Lys Ala Ile Asp Asp Cys Gln Lys Gln Ala His His Ser Asn Val
1               5                   10                  15

Leu Gln Thr Ser Val Gln Thr Thr Ala Thr Phe Thr Ser Met Asp Thr
             20                  25                  30

Ser Gln Leu Pro Gly Asn Ser Val Phe Lys Glu Cys Met Lys Gln Lys
         35                  40                  45

Lys Lys Glu Phe Ser Ser Gly Lys
     50                  55

<210> SEQ ID NO 57
<211> LENGTH: 55
<212> TYPE: PRT
<213> ORGANISM: Artificial
<220> FEATURE:
<223> OTHER INFORMATION: Synthetic fusion protein

<400> SEQUENCE: 57

Lys Ala Ile Asp Asp Cys Gln Lys Gln Ala His His Ser Asn Val Leu
1               5                   10                  15

Gln Thr Ser Val Gln Thr Thr Ala Thr Phe Thr Ser Met Asp Thr Ser
             20                  25                  30

Gln Leu Pro Gly Asn Ser Val Phe Lys Glu Cys Met Lys Gln Lys Lys
         35                  40                  45

Lys Glu Phe Ser Ser Gly Lys
     50                  55

<210> SEQ ID NO 58
<211> LENGTH: 54
<212> TYPE: PRT
```

```
<213> ORGANISM: Artificial
<220> FEATURE:
<223> OTHER INFORMATION: Synthetic fusion protein

<400> SEQUENCE: 58

Ala Ile Asp Asp Cys Gln Lys Gln Ala His His Ser Asn Val Leu Gln
1               5                   10                  15

Thr Ser Val Gln Thr Thr Ala Thr Phe Thr Ser Met Asp Thr Ser Gln
            20                  25                  30

Leu Pro Gly Asn Ser Val Phe Lys Glu Cys Met Lys Gln Lys Lys Lys
        35                  40                  45

Glu Phe Ser Ser Gly Lys
    50

<210> SEQ ID NO 59
<211> LENGTH: 53
<212> TYPE: PRT
<213> ORGANISM: Artificial
<220> FEATURE:
<223> OTHER INFORMATION: Synthetic fusion protein

<400> SEQUENCE: 59

Ile Asp Asp Cys Gln Lys Gln Ala His His Ser Asn Val Leu Gln Thr
1               5                   10                  15

Ser Val Gln Thr Thr Ala Thr Phe Thr Ser Met Asp Thr Ser Gln Leu
            20                  25                  30

Pro Gly Asn Ser Val Phe Lys Glu Cys Met Lys Gln Lys Lys Lys Glu
        35                  40                  45

Phe Ser Ser Gly Lys
    50

<210> SEQ ID NO 60
<211> LENGTH: 52
<212> TYPE: PRT
<213> ORGANISM: Artificial
<220> FEATURE:
<223> OTHER INFORMATION: Synthetic fusion protein

<400> SEQUENCE: 60

Asp Asp Cys Gln Lys Gln Ala His His Ser Asn Val Leu Gln Thr Ser
1               5                   10                  15

Val Gln Thr Thr Ala Thr Phe Thr Ser Met Asp Thr Ser Gln Leu Pro
            20                  25                  30

Gly Asn Ser Val Phe Lys Glu Cys Met Lys Gln Lys Lys Lys Glu Phe
        35                  40                  45

Ser Ser Gly Lys
    50

<210> SEQ ID NO 61
<211> LENGTH: 51
<212> TYPE: PRT
<213> ORGANISM: Artificial
<220> FEATURE:
<223> OTHER INFORMATION: Synthetic fusion protein

<400> SEQUENCE: 61

Asp Cys Gln Lys Gln Ala His His Ser Asn Val Leu Gln Thr Ser Val
1               5                   10                  15

Gln Thr Thr Ala Thr Phe Thr Ser Met Asp Thr Ser Gln Leu Pro Gly
            20                  25                  30
```

Asn Ser Val Phe Lys Glu Cys Met Lys Gln Lys Lys Glu Phe Ser
        35                  40                  45

Ser Gly Lys
    50

<210> SEQ ID NO 62
<211> LENGTH: 50
<212> TYPE: PRT
<213> ORGANISM: Artificial
<220> FEATURE:
<223> OTHER INFORMATION: Synthetic fusion protein

<400> SEQUENCE: 62

Cys Gln Lys Gln Ala His His Ser Asn Val Leu Gln Thr Ser Val Gln
1               5                   10                  15

Thr Thr Ala Thr Phe Thr Ser Met Asp Thr Ser Gln Leu Pro Gly Asn
            20                  25                  30

Ser Val Phe Lys Glu Cys Met Lys Gln Lys Lys Glu Phe Ser Ser
        35                  40                  45

Gly Lys
    50

<210> SEQ ID NO 63
<211> LENGTH: 49
<212> TYPE: PRT
<213> ORGANISM: Artificial
<220> FEATURE:
<223> OTHER INFORMATION: Synthetic fusion protein

<400> SEQUENCE: 63

Gln Lys Gln Ala His His Ser Asn Val Leu Gln Thr Ser Val Gln Thr
1               5                   10                  15

Thr Ala Thr Phe Thr Ser Met Asp Thr Ser Gln Leu Pro Gly Asn Ser
            20                  25                  30

Val Phe Lys Glu Cys Met Lys Gln Lys Lys Glu Phe Ser Ser Gly
        35                  40                  45

Lys

<210> SEQ ID NO 64
<211> LENGTH: 48
<212> TYPE: PRT
<213> ORGANISM: Artificial
<220> FEATURE:
<223> OTHER INFORMATION: Synthetic fusion protein

<400> SEQUENCE: 64

Lys Gln Ala His His Ser Asn Val Leu Gln Thr Ser Val Gln Thr Thr
1               5                   10                  15

Ala Thr Phe Thr Ser Met Asp Thr Ser Gln Leu Pro Gly Asn Ser Val
            20                  25                  30

Phe Lys Glu Cys Met Lys Gln Lys Lys Glu Phe Ser Ser Gly Lys
        35                  40                  45

<210> SEQ ID NO 65
<211> LENGTH: 47
<212> TYPE: PRT
<213> ORGANISM: Artificial
<220> FEATURE:
<223> OTHER INFORMATION: Synthetic fusion protein

<400> SEQUENCE: 65

Gln Ala His His Ser Asn Val Leu Gln Thr Ser Val Gln Thr Thr Ala
1               5                   10                  15

Thr Phe Thr Ser Met Asp Thr Ser Gln Leu Pro Gly Asn Ser Val Phe
            20                  25                  30

Lys Glu Cys Met Lys Gln Lys Lys Lys Glu Phe Ser Ser Gly Lys
        35                  40                  45

<210> SEQ ID NO 66
<211> LENGTH: 46
<212> TYPE: PRT
<213> ORGANISM: Artificial
<220> FEATURE:
<223> OTHER INFORMATION: Synthetic fusion protein

<400> SEQUENCE: 66

Ala His His Ser Asn Val Leu Gln Thr Ser Val Gln Thr Thr Ala Thr
1               5                   10                  15

Phe Thr Ser Met Asp Thr Ser Gln Leu Pro Gly Asn Ser Val Phe Lys
            20                  25                  30

Glu Cys Met Lys Gln Lys Lys Lys Glu Phe Ser Ser Gly Lys
        35                  40                  45

<210> SEQ ID NO 67
<211> LENGTH: 45
<212> TYPE: PRT
<213> ORGANISM: Artificial
<220> FEATURE:
<223> OTHER INFORMATION: Synthetic fusion protein

<400> SEQUENCE: 67

His His Ser Asn Val Leu Gln Thr Ser Val Gln Thr Thr Ala Thr Phe
1               5                   10                  15

Thr Ser Met Asp Thr Ser Gln Leu Pro Gly Asn Ser Val Phe Lys Glu
            20                  25                  30

Cys Met Lys Gln Lys Lys Lys Glu Phe Ser Ser Gly Lys
        35                  40                  45

<210> SEQ ID NO 68
<211> LENGTH: 44
<212> TYPE: PRT
<213> ORGANISM: Artificial
<220> FEATURE:
<223> OTHER INFORMATION: Synthetic fusion protein

<400> SEQUENCE: 68

His Ser Asn Val Leu Gln Thr Ser Val Gln Thr Thr Ala Thr Phe Thr
1               5                   10                  15

Ser Met Asp Thr Ser Gln Leu Pro Gly Asn Ser Val Phe Lys Glu Cys
            20                  25                  30

Met Lys Gln Lys Lys Lys Glu Phe Ser Ser Gly Lys
        35                  40

<210> SEQ ID NO 69
<211> LENGTH: 43
<212> TYPE: PRT
<213> ORGANISM: Artificial
<220> FEATURE:
<223> OTHER INFORMATION: Synthetic fusion protein

<400> SEQUENCE: 69

Ser Asn Val Leu Gln Thr Ser Val Gln Thr Thr Ala Thr Phe Thr Ser
1               5                   10                  15

Met Asp Thr Ser Gln Leu Pro Gly Asn Ser Val Phe Lys Glu Cys Met
            20                  25                  30

Lys Gln Lys Lys Lys Glu Phe Ser Ser Gly Lys
        35                  40

<210> SEQ ID NO 70
<211> LENGTH: 42
<212> TYPE: PRT
<213> ORGANISM: Artificial
<220> FEATURE:
<223> OTHER INFORMATION: Synthetic fusion protein

<400> SEQUENCE: 70

Asn Val Leu Gln Thr Ser Val Gln Thr Thr Ala Thr Phe Thr Ser Met
1               5                   10                  15

Asp Thr Ser Gln Leu Pro Gly Asn Ser Val Phe Lys Glu Cys Met Lys
            20                  25                  30

Gln Lys Lys Lys Glu Phe Ser Ser Gly Lys
        35                  40

<210> SEQ ID NO 71
<211> LENGTH: 41
<212> TYPE: PRT
<213> ORGANISM: Artificial
<220> FEATURE:
<223> OTHER INFORMATION: Synthetic fusion protein

<400> SEQUENCE: 71

Val Leu Gln Thr Ser Val Gln Thr Thr Ala Thr Phe Thr Ser Met Asp
1               5                   10                  15

Thr Ser Gln Leu Pro Gly Asn Ser Val Phe Lys Glu Cys Met Lys Gln
            20                  25                  30

Lys Lys Lys Glu Phe Ser Ser Gly Lys
        35                  40

<210> SEQ ID NO 72
<211> LENGTH: 40
<212> TYPE: PRT
<213> ORGANISM: Artificial
<220> FEATURE:
<223> OTHER INFORMATION: Synthetic fusion protein

<400> SEQUENCE: 72

Leu Gln Thr Ser Val Gln Thr Thr Ala Thr Phe Thr Ser Met Asp Thr
1               5                   10                  15

Ser Gln Leu Pro Gly Asn Ser Val Phe Lys Glu Cys Met Lys Gln Lys
            20                  25                  30

Lys Lys Glu Phe Ser Ser Gly Lys
        35                  40

<210> SEQ ID NO 73
<211> LENGTH: 39
<212> TYPE: PRT
<213> ORGANISM: Artificial
<220> FEATURE:
<223> OTHER INFORMATION: Synthetic fusion protein

```
<400> SEQUENCE: 73

Gln Thr Ser Val Gln Thr Thr Ala Thr Phe Thr Ser Met Asp Thr Ser
1               5                   10                  15

Gln Leu Pro Gly Asn Ser Val Phe Lys Glu Cys Met Lys Gln Lys Lys
            20                  25                  30

Lys Glu Phe Ser Ser Gly Lys
        35

<210> SEQ ID NO 74
<211> LENGTH: 38
<212> TYPE: PRT
<213> ORGANISM: Artificial
<220> FEATURE:
<223> OTHER INFORMATION: Synthetic fusion protein

<400> SEQUENCE: 74

Thr Ser Val Gln Thr Thr Ala Thr Phe Thr Ser Met Asp Thr Ser Gln
1               5                   10                  15

Leu Pro Gly Asn Ser Val Phe Lys Glu Cys Met Lys Gln Lys Lys Lys
            20                  25                  30

Glu Phe Ser Ser Gly Lys
        35

<210> SEQ ID NO 75
<211> LENGTH: 37
<212> TYPE: PRT
<213> ORGANISM: Artificial
<220> FEATURE:
<223> OTHER INFORMATION: Synthetic fusion protein

<400> SEQUENCE: 75

Ser Val Gln Thr Thr Ala Thr Phe Thr Ser Met Asp Thr Ser Gln Leu
1               5                   10                  15

Pro Gly Asn Ser Val Phe Lys Glu Cys Met Lys Gln Lys Lys Lys Glu
            20                  25                  30

Phe Ser Ser Gly Lys
        35

<210> SEQ ID NO 76
<211> LENGTH: 36
<212> TYPE: PRT
<213> ORGANISM: Artificial
<220> FEATURE:
<223> OTHER INFORMATION: Synthetic fusion protein

<400> SEQUENCE: 76

Val Gln Thr Thr Ala Thr Phe Thr Ser Met Asp Thr Ser Gln Leu Pro
1               5                   10                  15

Gly Asn Ser Val Phe Lys Glu Cys Met Lys Gln Lys Lys Lys Glu Phe
            20                  25                  30

Ser Ser Gly Lys
        35

<210> SEQ ID NO 77
<211> LENGTH: 35
<212> TYPE: PRT
<213> ORGANISM: Artificial
<220> FEATURE:
<223> OTHER INFORMATION: Synthetic fusion protein
```

<400> SEQUENCE: 77

Gln Thr Thr Ala Thr Phe Thr Ser Met Asp Thr Ser Gln Leu Pro Gly
1               5                   10                  15

Asn Ser Val Phe Lys Glu Cys Met Lys Gln Lys Lys Lys Glu Phe Ser
            20                  25                  30

Ser Gly Lys
        35

<210> SEQ ID NO 78
<211> LENGTH: 34
<212> TYPE: PRT
<213> ORGANISM: Artificial
<220> FEATURE:
<223> OTHER INFORMATION: Synthetic fusion protein

<400> SEQUENCE: 78

Thr Thr Ala Thr Phe Thr Ser Met Asp Thr Ser Gln Leu Pro Gly Asn
1               5                   10                  15

Ser Val Phe Lys Glu Cys Met Lys Gln Lys Lys Lys Glu Phe Ser Ser
            20                  25                  30

Gly Lys

<210> SEQ ID NO 79
<211> LENGTH: 20
<212> TYPE: PRT
<213> ORGANISM: Artificial
<220> FEATURE:
<223> OTHER INFORMATION: Synthetic fusion protein

<400> SEQUENCE: 79

Gly Asn Ser Val Phe Lys Glu Cys Met Lys Gln Lys Lys Lys Glu Phe
1               5                   10                  15

Ser Ser Gly Lys
            20

<210> SEQ ID NO 80
<211> LENGTH: 19
<212> TYPE: PRT
<213> ORGANISM: Artificial
<220> FEATURE:
<223> OTHER INFORMATION: Synthetic fusion protein

<400> SEQUENCE: 80

Asn Ser Val Phe Lys Glu Cys Met Lys Gln Lys Lys Lys Glu Phe Ser
1               5                   10                  15

Ser Gly Lys

<210> SEQ ID NO 81
<211> LENGTH: 18
<212> TYPE: PRT
<213> ORGANISM: Artificial
<220> FEATURE:
<223> OTHER INFORMATION: Synthetic fusion protein

<400> SEQUENCE: 81

Ser Val Phe Lys Glu Cys Met Lys Gln Lys Lys Lys Glu Phe Ser Ser
1               5                   10                  15

Gly Lys

<210> SEQ ID NO 82
<211> LENGTH: 17

```
<212> TYPE: PRT
<213> ORGANISM: Artificial
<220> FEATURE:
<223> OTHER INFORMATION: Synthetic fusion protein

<400> SEQUENCE: 82

Val Phe Lys Glu Cys Met Lys Gln Lys Lys Lys Glu Phe Ser Ser Gly
1               5                   10                  15

Lys

<210> SEQ ID NO 83
<211> LENGTH: 16
<212> TYPE: PRT
<213> ORGANISM: Artificial
<220> FEATURE:
<223> OTHER INFORMATION: Synthetic fusion protein

<400> SEQUENCE: 83

Phe Lys Glu Cys Met Lys Gln Lys Lys Lys Glu Phe Ser Ser Gly Lys
1               5                   10                  15

<210> SEQ ID NO 84
<211> LENGTH: 15
<212> TYPE: PRT
<213> ORGANISM: Artificial
<220> FEATURE:
<223> OTHER INFORMATION: Synthetic fusion protein

<400> SEQUENCE: 84

Lys Glu Cys Met Lys Gln Lys Lys Lys Glu Phe Ser Ser Gly Lys
1               5                   10                  15

<210> SEQ ID NO 85
<211> LENGTH: 14
<212> TYPE: PRT
<213> ORGANISM: Artificial
<220> FEATURE:
<223> OTHER INFORMATION: Synthetic fusion protein

<400> SEQUENCE: 85

Glu Cys Met Lys Gln Lys Lys Lys Glu Phe Ser Ser Gly Lys
1               5                   10

<210> SEQ ID NO 86
<211> LENGTH: 13
<212> TYPE: PRT
<213> ORGANISM: Artificial
<220> FEATURE:
<223> OTHER INFORMATION: Synthetic fusion protein

<400> SEQUENCE: 86

Cys Met Lys Gln Lys Lys Lys Glu Phe Ser Ser Gly Lys
1               5                   10

<210> SEQ ID NO 87
<211> LENGTH: 12
<212> TYPE: PRT
<213> ORGANISM: Artificial
<220> FEATURE:
<223> OTHER INFORMATION: Synthetic fusion protein

<400> SEQUENCE: 87

Met Lys Gln Lys Lys Lys Glu Phe Ser Ser Gly Lys
1               5                   10

<210> SEQ ID NO 88
```

```
<211> LENGTH: 11
<212> TYPE: PRT
<213> ORGANISM: Artificial
<220> FEATURE:
<223> OTHER INFORMATION: Synthetic fusion protein

<400> SEQUENCE: 88

Lys Gln Lys Lys Lys Glu Phe Ser Ser Gly Lys
1               5                   10

<210> SEQ ID NO 89
<211> LENGTH: 10
<212> TYPE: PRT
<213> ORGANISM: Artificial
<220> FEATURE:
<223> OTHER INFORMATION: Synthetic fusion protein

<400> SEQUENCE: 89

Gln Lys Lys Lys Glu Phe Ser Ser Gly Lys
1               5                   10

<210> SEQ ID NO 90
<211> LENGTH: 9
<212> TYPE: PRT
<213> ORGANISM: Artificial
<220> FEATURE:
<223> OTHER INFORMATION: Synthetic fusion protein

<400> SEQUENCE: 90

Lys Lys Lys Glu Phe Ser Ser Gly Lys
1               5

<210> SEQ ID NO 91
<211> LENGTH: 8
<212> TYPE: PRT
<213> ORGANISM: Artificial
<220> FEATURE:
<223> OTHER INFORMATION: Synthetic fusion protein

<400> SEQUENCE: 91

Lys Lys Glu Phe Ser Ser Gly Lys
1               5

<210> SEQ ID NO 92
<211> LENGTH: 7
<212> TYPE: PRT
<213> ORGANISM: Artificial
<220> FEATURE:
<223> OTHER INFORMATION: Synthetic fusion protein

<400> SEQUENCE: 92

Lys Glu Phe Ser Ser Gly Lys
1               5

<210> SEQ ID NO 93
<211> LENGTH: 6
<212> TYPE: PRT
<213> ORGANISM: Artificial
<220> FEATURE:
<223> OTHER INFORMATION: Synthetic fusion protein

<400> SEQUENCE: 93

Glu Phe Ser Ser Gly Lys
1               5

<210> SEQ ID NO 94
<211> LENGTH: 5
```

```
<212> TYPE: PRT
<213> ORGANISM: Artificial
<220> FEATURE:
<223> OTHER INFORMATION: Synthetic fusion protein

<400> SEQUENCE: 94

Phe Ser Ser Gly Lys
1               5

<210> SEQ ID NO 95
<211> LENGTH: 38
<212> TYPE: PRT
<213> ORGANISM: Artificial
<220> FEATURE:
<223> OTHER INFORMATION: Synthetic fusion protein

<400> SEQUENCE: 95

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 96
<211> LENGTH: 37
<212> TYPE: PRT
<213> ORGANISM: Artificial
<220> FEATURE:
<223> OTHER INFORMATION: Synthetic fusion protein

<400> SEQUENCE: 96

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn
        35

<210> SEQ ID NO 97
<211> LENGTH: 36
<212> TYPE: PRT
<213> ORGANISM: Artificial
<220> FEATURE:
<223> OTHER INFORMATION: Synthetic fusion protein

<400> SEQUENCE: 97

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys
        35

<210> SEQ ID NO 98
<211> LENGTH: 35
<212> TYPE: PRT
<213> ORGANISM: Artificial
<220> FEATURE:
<223> OTHER INFORMATION: Synthetic fusion protein

<400> SEQUENCE: 98

His Ser Asp Gly Ile Phe Thr Asp Ser Tyr Ser Arg Tyr Arg Lys Gln
1               5                   10                  15
```

Met Ala Val Lys Lys Tyr Leu Ala Ala Val Leu Gly Lys Arg Tyr Lys
            20                  25                  30

Gln Arg Val
        35

<210> SEQ ID NO 99
<211> LENGTH: 34
<212> TYPE: PRT
<213> ORGANISM: Artificial
<220> FEATURE:
<223> OTHER INFORMATION: Synthetic fusion protein

<400> SEQUENCE: 99

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg

<210> SEQ ID NO 100
<211> LENGTH: 33
<212> TYPE: PRT
<213> ORGANISM: Artificial
<220> FEATURE:
<223> OTHER INFORMATION: Synthetic fusion protein

<400> SEQUENCE: 100

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln

<210> SEQ ID NO 101
<211> LENGTH: 32
<212> TYPE: PRT
<213> ORGANISM: Artificial
<220> FEATURE:
<223> OTHER INFORMATION: Synthetic fusion protein

<400> SEQUENCE: 101

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

<210> SEQ ID NO 102
<211> LENGTH: 31
<212> TYPE: PRT
<213> ORGANISM: Artificial
<220> FEATURE:
<223> OTHER INFORMATION: Synthetic fusion protein

<400> SEQUENCE: 102

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr
            20                  25                  30

<210> SEQ ID NO 103
<211> LENGTH: 30
<212> TYPE: PRT

```
<213> ORGANISM: Artificial
<220> FEATURE:
<223> OTHER INFORMATION: Synthetic fusion protein

<400> SEQUENCE: 103

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg
            20                  25                  30

<210> SEQ ID NO 104
<211> LENGTH: 29
<212> TYPE: PRT
<213> ORGANISM: Artificial
<220> FEATURE:
<223> OTHER INFORMATION: Synthetic fusion protein

<400> SEQUENCE: 104

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys
            20                  25

<210> SEQ ID NO 105
<211> LENGTH: 28
<212> TYPE: PRT
<213> ORGANISM: Artificial
<220> FEATURE:
<223> OTHER INFORMATION: Synthetic fusion protein

<400> SEQUENCE: 105

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly
            20                  25

<210> SEQ ID NO 106
<211> LENGTH: 27
<212> TYPE: PRT
<213> ORGANISM: Artificial
<220> FEATURE:
<223> OTHER INFORMATION: Synthetic fusion protein

<400> SEQUENCE: 106

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 107
<211> LENGTH: 26
<212> TYPE: PRT
<213> ORGANISM: Artificial
<220> FEATURE:
<223> OTHER INFORMATION: Synthetic fusion protein

<400> SEQUENCE: 107

His Ser Asp Gly Ile Phe Thr Asp Ser Tyr Ser Arg Tyr Arg Lys Gln
1               5                   10                  15

Met Ala Val Lys Lys Tyr Leu Ala Ala Val
            20                  25

<210> SEQ ID NO 108
<211> LENGTH: 25
```

```
<212> TYPE: PRT
<213> ORGANISM: Artificial
<220> FEATURE:
<223> OTHER INFORMATION: Synthetic fusion protein

<400> SEQUENCE: 108

His Ser Asp Gly Ile Phe Thr Asp Ser Tyr Ser Arg Tyr Arg Lys Gln
1               5                   10                  15

Met Ala Val Lys Lys Tyr Leu Ala Ala
            20                  25

<210> SEQ ID NO 109
<211> LENGTH: 24
<212> TYPE: PRT
<213> ORGANISM: Artificial
<220> FEATURE:
<223> OTHER INFORMATION: Synthetic fusion protein

<400> SEQUENCE: 109

His Ser Asp Gly Ile Phe Thr Asp Ser Tyr Ser Arg Tyr Arg Lys Gln
1               5                   10                  15

Met Ala Val Lys Lys Tyr Leu Ala
            20

<210> SEQ ID NO 110
<211> LENGTH: 23
<212> TYPE: PRT
<213> ORGANISM: Artificial
<220> FEATURE:
<223> OTHER INFORMATION: Synthetic fusion protein

<400> SEQUENCE: 110

His Ser Asp Gly Ile Phe Thr Asp Ser Tyr Ser Arg Tyr Arg Lys Gln
1               5                   10                  15

Met Ala Val Lys Lys Tyr Leu
            20

<210> SEQ ID NO 111
<211> LENGTH: 22
<212> TYPE: PRT
<213> ORGANISM: Artificial
<220> FEATURE:
<223> OTHER INFORMATION: Synthetic fusion protein

<400> SEQUENCE: 111

His Ser Asp Gly Ile Phe Thr Asp Ser Tyr Ser Arg Tyr Arg Lys Gln
1               5                   10                  15

Met Ala Val Lys Lys Tyr
            20

<210> SEQ ID NO 112
<211> LENGTH: 21
<212> TYPE: PRT
<213> ORGANISM: Artificial
<220> FEATURE:
<223> OTHER INFORMATION: Synthetic fusion protein

<400> SEQUENCE: 112

His Ser Asp Gly Ile Phe Thr Asp Ser Tyr Ser Arg Tyr Arg Lys Gln
1               5                   10                  15

Met Ala Val Lys Lys
            20

<210> SEQ ID NO 113
```

<211> LENGTH: 20
<212> TYPE: PRT
<213> ORGANISM: Artificial
<220> FEATURE:
<223> OTHER INFORMATION: Synthetic fusion protein

<400> SEQUENCE: 113

His Ser Asp Gly Ile Phe Thr Asp Ser Tyr Ser Arg Tyr Arg Lys Gln
1               5                   10                  15

Met Ala Val Lys
            20

<210> SEQ ID NO 114
<211> LENGTH: 19
<212> TYPE: PRT
<213> ORGANISM: Artificial
<220> FEATURE:
<223> OTHER INFORMATION: Synthetic fusion protein

<400> SEQUENCE: 114

His Ser Asp Gly Ile Phe Thr Asp Ser Tyr Ser Arg Tyr Arg Lys Gln
1               5                   10                  15

Met Ala Val

<210> SEQ ID NO 115
<211> LENGTH: 18
<212> TYPE: PRT
<213> ORGANISM: Artificial
<220> FEATURE:
<223> OTHER INFORMATION: Synthetic fusion protein

<400> SEQUENCE: 115

His Ser Asp Gly Ile Phe Thr Asp Ser Tyr Ser Arg Tyr Arg Lys Gln
1               5                   10                  15

Met Ala

<210> SEQ ID NO 116
<211> LENGTH: 17
<212> TYPE: PRT
<213> ORGANISM: Artificial
<220> FEATURE:
<223> OTHER INFORMATION: Synthetic fusion protein

<400> SEQUENCE: 116

His Ser Asp Gly Ile Phe Thr Asp Ser Tyr Ser Arg Tyr Arg Lys Gln
1               5                   10                  15

Met

<210> SEQ ID NO 117
<211> LENGTH: 16
<212> TYPE: PRT
<213> ORGANISM: Artificial
<220> FEATURE:
<223> OTHER INFORMATION: Synthetic fusion protein

<400> SEQUENCE: 117

His Ser Asp Gly Ile Phe Thr Asp Ser Tyr Ser Arg Tyr Arg Lys Gln
1               5                   10                  15

<210> SEQ ID NO 118
<211> LENGTH: 15
<212> TYPE: PRT
<213> ORGANISM: Artificial
<220> FEATURE:
<223> OTHER INFORMATION: Synthetic fusion protein

<400> SEQUENCE: 118

His Ser Asp Gly Ile Phe Thr Asp Ser Tyr Ser Arg Tyr Arg Lys
1               5                   10                  15

<210> SEQ ID NO 119
<211> LENGTH: 15
<212> TYPE: PRT
<213> ORGANISM: Artificial
<220> FEATURE:
<223> OTHER INFORMATION: Synthetic fusion protein

<400> SEQUENCE: 119

His Ser Asp Gly Ile Phe Thr Asp Ser Tyr Ser Arg Tyr Arg Ala
1               5                   10                  15

<210> SEQ ID NO 120
<211> LENGTH: 14
<212> TYPE: PRT
<213> ORGANISM: Artificial
<220> FEATURE:
<223> OTHER INFORMATION: Synthetic fusion protein

<400> SEQUENCE: 120

His Ser Asp Gly Ile Phe Thr Asp Ser Tyr Ser Arg Tyr Arg
1               5                   10

<210> SEQ ID NO 121
<211> LENGTH: 13
<212> TYPE: PRT
<213> ORGANISM: Artificial
<220> FEATURE:
<223> OTHER INFORMATION: Synthetic fusion protein

<400> SEQUENCE: 121

His Ser Asp Gly Ile Phe Thr Asp Ser Tyr Ser Arg Tyr
1               5                   10

<210> SEQ ID NO 122
<211> LENGTH: 12
<212> TYPE: PRT
<213> ORGANISM: Artificial
<220> FEATURE:
<223> OTHER INFORMATION: Synthetic fusion protein

<400> SEQUENCE: 122

His Ser Asp Gly Ile Phe Thr Asp Ser Tyr Ser Arg
1               5                   10

<210> SEQ ID NO 123
<211> LENGTH: 12
<212> TYPE: PRT
<213> ORGANISM: Artificial
<220> FEATURE:
<223> OTHER INFORMATION: Synthetic fusion protein

<400> SEQUENCE: 123

His Ser Asp Gly Ile Phe Thr Asp Ser Tyr Ser Ala
1               5                   10

<210> SEQ ID NO 124
<211> LENGTH: 12
<212> TYPE: PRT
<213> ORGANISM: Artificial
<220> FEATURE:
<223> OTHER INFORMATION: Synthetic fusion protein

```
<400> SEQUENCE: 124

His Ser Asp Gly Ile Phe Thr Asp Ser Tyr Ser Lys
1               5                   10

<210> SEQ ID NO 125
<211> LENGTH: 11
<212> TYPE: PRT
<213> ORGANISM: Artificial
<220> FEATURE:
<223> OTHER INFORMATION: Synthetic fusion protein

<400> SEQUENCE: 125

His Ser Asp Gly Ile Phe Thr Asp Ser Tyr Ser
1               5                   10

<210> SEQ ID NO 126
<211> LENGTH: 10
<212> TYPE: PRT
<213> ORGANISM: Artificial
<220> FEATURE:
<223> OTHER INFORMATION: Synthetic fusion protein

<400> SEQUENCE: 126

His Ser Asp Gly Ile Phe Thr Asp Ser Tyr
1               5                   10

<210> SEQ ID NO 127
<211> LENGTH: 9
<212> TYPE: PRT
<213> ORGANISM: Artificial
<220> FEATURE:
<223> OTHER INFORMATION: Synthetic fusion protein

<400> SEQUENCE: 127

His Ser Asp Gly Ile Phe Thr Asp Ser
1               5

<210> SEQ ID NO 128
<211> LENGTH: 8
<212> TYPE: PRT
<213> ORGANISM: Artificial
<220> FEATURE:
<223> OTHER INFORMATION: Synthetic fusion protein

<400> SEQUENCE: 128

His Ser Asp Gly Ile Phe Thr Asp
1               5

<210> SEQ ID NO 129
<211> LENGTH: 7
<212> TYPE: PRT
<213> ORGANISM: Artificial
<220> FEATURE:
<223> OTHER INFORMATION: Synthetic fusion protein

<400> SEQUENCE: 129

His Ser Asp Gly Ile Phe Thr
1               5

<210> SEQ ID NO 130
<211> LENGTH: 6
<212> TYPE: PRT
<213> ORGANISM: Artificial
<220> FEATURE:
<223> OTHER INFORMATION: Synthetic fusion protein
```

```
<400> SEQUENCE: 130

His Ser Asp Gly Ile Phe
1               5

<210> SEQ ID NO 131
<211> LENGTH: 39
<212> TYPE: PRT
<213> ORGANISM: Artificial
<220> FEATURE:
<223> OTHER INFORMATION: Synthetic fusion protein

<400> SEQUENCE: 131

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg Tyr
            20                  25                  30

Lys Gln Arg Val Lys Asn Lys
        35

<210> SEQ ID NO 132
<211> LENGTH: 39
<212> TYPE: PRT
<213> ORGANISM: Artificial
<220> FEATURE:
<223> OTHER INFORMATION: Synthetic fusion protein

<400> SEQUENCE: 132

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg Tyr
            20                  25                  30

Lys Gln Arg Val Lys Asn Lys
        35

<210> SEQ ID NO 133
<211> LENGTH: 38
<212> TYPE: PRT
<213> ORGANISM: Artificial
<220> FEATURE:
<223> OTHER INFORMATION: Synthetic fusion protein

<400> SEQUENCE: 133

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg Tyr
            20                  25                  30

Lys Gln Arg Val Lys Asn
        35

<210> SEQ ID NO 134
<211> LENGTH: 37
<212> TYPE: PRT
<213> ORGANISM: Artificial
<220> FEATURE:
<223> OTHER INFORMATION: Synthetic fusion protein

<400> SEQUENCE: 134

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg Tyr
            20                  25                  30
```

Lys Gln Arg Val Lys
        35

<210> SEQ ID NO 135
<211> LENGTH: 36
<212> TYPE: PRT
<213> ORGANISM: Artificial
<220> FEATURE:
<223> OTHER INFORMATION: Synthetic fusion protein

<400> SEQUENCE: 135

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg Tyr
            20                  25                  30

Lys Gln Arg Val
        35

<210> SEQ ID NO 136
<211> LENGTH: 35
<212> TYPE: PRT
<213> ORGANISM: Artificial
<220> FEATURE:
<223> OTHER INFORMATION: Synthetic fusion protein

<400> SEQUENCE: 136

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg Tyr
            20                  25                  30

Lys Gln Arg
        35

<210> SEQ ID NO 137
<211> LENGTH: 34
<212> TYPE: PRT
<213> ORGANISM: Artificial
<220> FEATURE:
<223> OTHER INFORMATION: Synthetic fusion protein

<400> SEQUENCE: 137

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg Tyr
            20                  25                  30

Lys Gln

<210> SEQ ID NO 138
<211> LENGTH: 33
<212> TYPE: PRT
<213> ORGANISM: Artificial
<220> FEATURE:
<223> OTHER INFORMATION: Synthetic fusion protein

<400> SEQUENCE: 138

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg Tyr
            20                  25                  30

Lys

<210> SEQ ID NO 139

```
<211> LENGTH: 32
<212> TYPE: PRT
<213> ORGANISM: Artificial
<220> FEATURE:
<223> OTHER INFORMATION: Synthetic fusion protein

<400> SEQUENCE: 139

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg Tyr
            20                  25                  30

<210> SEQ ID NO 140
<211> LENGTH: 31
<212> TYPE: PRT
<213> ORGANISM: Artificial
<220> FEATURE:
<223> OTHER INFORMATION: Synthetic fusion protein

<400> SEQUENCE: 140

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys Arg
            20                  25                  30

<210> SEQ ID NO 141
<211> LENGTH: 30
<212> TYPE: PRT
<213> ORGANISM: Artificial
<220> FEATURE:
<223> OTHER INFORMATION: Synthetic fusion protein

<400> SEQUENCE: 141

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly Lys
            20                  25                  30

<210> SEQ ID NO 142
<211> LENGTH: 29
<212> TYPE: PRT
<213> ORGANISM: Artificial
<220> FEATURE:
<223> OTHER INFORMATION: Synthetic fusion protein

<400> SEQUENCE: 142

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Gly
            20                  25

<210> SEQ ID NO 143
<211> LENGTH: 28
<212> TYPE: PRT
<213> ORGANISM: Artificial
<220> FEATURE:
<223> OTHER INFORMATION: Synthetic fusion protein

<400> SEQUENCE: 143

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu
            20                  25
```

```
<210> SEQ ID NO 144
<211> LENGTH: 27
<212> TYPE: PRT
<213> ORGANISM: Artificial
<220> FEATURE:
<223> OTHER INFORMATION: Synthetic fusion protein

<400> SEQUENCE: 144

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val
            20                  25

<210> SEQ ID NO 145
<211> LENGTH: 26
<212> TYPE: PRT
<213> ORGANISM: Artificial
<220> FEATURE:
<223> OTHER INFORMATION: Synthetic fusion protein

<400> SEQUENCE: 145

His Ser Asp Gly Ile Phe Thr Asp Ser Tyr Ser Ser Arg Tyr Arg Lys
1               5                   10                  15

Gln Met Ala Val Lys Lys Tyr Leu Ala Ala
            20                  25

<210> SEQ ID NO 146
<211> LENGTH: 25
<212> TYPE: PRT
<213> ORGANISM: Artificial
<220> FEATURE:
<223> OTHER INFORMATION: Synthetic fusion protein

<400> SEQUENCE: 146

His Ser Asp Gly Ile Phe Thr Asp Ser Tyr Ser Ser Arg Tyr Arg Lys
1               5                   10                  15

Gln Met Ala Val Lys Lys Tyr Leu Ala
            20                  25

<210> SEQ ID NO 147
<211> LENGTH: 24
<212> TYPE: PRT
<213> ORGANISM: Artificial
<220> FEATURE:
<223> OTHER INFORMATION: Synthetic fusion protein

<400> SEQUENCE: 147

His Ser Asp Gly Ile Phe Thr Asp Ser Tyr Ser Ser Arg Tyr Arg Lys
1               5                   10                  15

Gln Met Ala Val Lys Lys Tyr Leu
            20

<210> SEQ ID NO 148
<211> LENGTH: 23
<212> TYPE: PRT
<213> ORGANISM: Artificial
<220> FEATURE:
<223> OTHER INFORMATION: Synthetic fusion protein

<400> SEQUENCE: 148

His Ser Asp Gly Ile Phe Thr Asp Ser Tyr Ser Ser Arg Tyr Arg Lys
1               5                   10                  15

Gln Met Ala Val Lys Lys Tyr
            20
```

<210> SEQ ID NO 149
<211> LENGTH: 22
<212> TYPE: PRT
<213> ORGANISM: Artificial
<220> FEATURE:
<223> OTHER INFORMATION: Synthetic fusion protein

<400> SEQUENCE: 149

His Ser Asp Gly Ile Phe Thr Asp Ser Tyr Ser Ser Arg Tyr Arg Lys
1               5                   10                  15

Gln Met Ala Val Lys Lys
            20

<210> SEQ ID NO 150
<211> LENGTH: 21
<212> TYPE: PRT
<213> ORGANISM: Artificial
<220> FEATURE:
<223> OTHER INFORMATION: Synthetic fusion protein

<400> SEQUENCE: 150

His Ser Asp Gly Ile Phe Thr Asp Ser Tyr Ser Ser Arg Tyr Arg Lys
1               5                   10                  15

Gln Met Ala Val Lys
            20

<210> SEQ ID NO 151
<211> LENGTH: 20
<212> TYPE: PRT
<213> ORGANISM: Artificial
<220> FEATURE:
<223> OTHER INFORMATION: Synthetic fusion protein

<400> SEQUENCE: 151

His Ser Asp Gly Ile Phe Thr Asp Ser Tyr Ser Ser Arg Tyr Arg Lys
1               5                   10                  15

Gln Met Ala Val
            20

<210> SEQ ID NO 152
<211> LENGTH: 19
<212> TYPE: PRT
<213> ORGANISM: Artificial
<220> FEATURE:
<223> OTHER INFORMATION: Synthetic fusion protein

<400> SEQUENCE: 152

His Ser Asp Gly Ile Phe Thr Asp Ser Tyr Ser Ser Arg Tyr Arg Lys
1               5                   10                  15

Gln Met Ala

<210> SEQ ID NO 153
<211> LENGTH: 18
<212> TYPE: PRT
<213> ORGANISM: Artificial
<220> FEATURE:
<223> OTHER INFORMATION: Synthetic fusion protein

<400> SEQUENCE: 153

His Ser Asp Gly Ile Phe Thr Asp Ser Tyr Ser Ser Arg Tyr Arg Lys
1               5                   10                  15

Gln Met

```
<210> SEQ ID NO 154
<211> LENGTH: 17
<212> TYPE: PRT
<213> ORGANISM: Artificial
<220> FEATURE:
<223> OTHER INFORMATION: Synthetic fusion protein

<400> SEQUENCE: 154

His Ser Asp Gly Ile Phe Thr Asp Ser Tyr Ser Ser Arg Tyr Arg Lys
1               5                   10                  15

Gln

<210> SEQ ID NO 155
<211> LENGTH: 16
<212> TYPE: PRT
<213> ORGANISM: Artificial
<220> FEATURE:
<223> OTHER INFORMATION: Synthetic fusion protein

<400> SEQUENCE: 155

His Ser Asp Gly Ile Phe Thr Asp Ser Tyr Ser Ser Arg Tyr Arg Lys
1               5                   10                  15

<210> SEQ ID NO 156
<211> LENGTH: 15
<212> TYPE: PRT
<213> ORGANISM: Artificial
<220> FEATURE:
<223> OTHER INFORMATION: Synthetic fusion protein

<400> SEQUENCE: 156

His Ser Asp Gly Ile Phe Thr Asp Ser Tyr Ser Ser Arg Tyr Arg
1               5                   10                  15

<210> SEQ ID NO 157
<211> LENGTH: 14
<212> TYPE: PRT
<213> ORGANISM: Artificial
<220> FEATURE:
<223> OTHER INFORMATION: Synthetic fusion protein

<400> SEQUENCE: 157

His Ser Asp Gly Ile Phe Thr Asp Ser Tyr Ser Ser Arg Tyr
1               5                   10

<210> SEQ ID NO 158
<211> LENGTH: 13
<212> TYPE: PRT
<213> ORGANISM: Artificial
<220> FEATURE:
<223> OTHER INFORMATION: Synthetic fusion protein

<400> SEQUENCE: 158

His Ser Asp Gly Ile Phe Thr Asp Ser Tyr Ser Ser Arg
1               5                   10

<210> SEQ ID NO 159
<211> LENGTH: 12
<212> TYPE: PRT
<213> ORGANISM: Artificial
<220> FEATURE:
<223> OTHER INFORMATION: Synthetic fusion protein

<400> SEQUENCE: 159

His Ser Asp Gly Ile Phe Thr Asp Ser Tyr Ser Ser
1               5                   10
```

```
<210> SEQ ID NO 160
<211> LENGTH: 5
<212> TYPE: PRT
<213> ORGANISM: Artificial
<220> FEATURE:
<223> OTHER INFORMATION: Peptide linker

<400> SEQUENCE: 160

Pro Ser Gly Ser Pro
1               5

<210> SEQ ID NO 161
<211> LENGTH: 5
<212> TYPE: PRT
<213> ORGANISM: Artificial
<220> FEATURE:
<223> OTHER INFORMATION: Peptide linker

<400> SEQUENCE: 161

Ala Ser Ala Ser Ala
1               5

<210> SEQ ID NO 162
<211> LENGTH: 3
<212> TYPE: PRT
<213> ORGANISM: Artificial
<220> FEATURE:
<223> OTHER INFORMATION: Peptide linker

<400> SEQUENCE: 162

Gly Gly Gly
1

<210> SEQ ID NO 163
<211> LENGTH: 15
<212> TYPE: PRT
<213> ORGANISM: Artificial
<220> FEATURE:
<223> OTHER INFORMATION: Peptide linker

<400> SEQUENCE: 163

Gly Gly Gly Gly Ser Gly Gly Gly Gly Ser Gly Gly Gly Gly Ser
1               5                   10                  15

<210> SEQ ID NO 164
<211> LENGTH: 4
<212> TYPE: PRT
<213> ORGANISM: Artificial
<220> FEATURE:
<223> OTHER INFORMATION: Peptide linker

<400> SEQUENCE: 164

Gly Gly Gly Gly
1

<210> SEQ ID NO 165
<211> LENGTH: 6
<212> TYPE: PRT
<213> ORGANISM: Artificial
<220> FEATURE:
<223> OTHER INFORMATION: Peptide linker

<400> SEQUENCE: 165

Gly Gly Ser Gly Gly Ser
1               5
```

<210> SEQ ID NO 166
<211> LENGTH: 5
<212> TYPE: PRT
<213> ORGANISM: Artificial
<220> FEATURE:
<223> OTHER INFORMATION: Peptide linker

<400> SEQUENCE: 166

Pro Ser Pro Ser Pro
1               5

<210> SEQ ID NO 167
<211> LENGTH: 5
<212> TYPE: PRT
<213> ORGANISM: Artificial
<220> FEATURE:
<223> OTHER INFORMATION: Peptide linker

<400> SEQUENCE: 167

Ala Ser Ala Ser Ala
1               5

<210> SEQ ID NO 168
<211> LENGTH: 5
<212> TYPE: PRT
<213> ORGANISM: Artificial
<220> FEATURE:
<223> OTHER INFORMATION: Peptide linker

<400> SEQUENCE: 168

Pro Ser Pro Ser Pro
1               5

<210> SEQ ID NO 169
<211> LENGTH: 4
<212> TYPE: PRT
<213> ORGANISM: Artificial
<220> FEATURE:
<223> OTHER INFORMATION: Peptide linker

<400> SEQUENCE: 169

Lys Lys Lys Lys
1

<210> SEQ ID NO 170
<211> LENGTH: 4
<212> TYPE: PRT
<213> ORGANISM: Artificial
<220> FEATURE:
<223> OTHER INFORMATION: Peptide linker

<400> SEQUENCE: 170

Arg Arg Arg Arg
1

<210> SEQ ID NO 171
<211> LENGTH: 7
<212> TYPE: PRT
<213> ORGANISM: Artificial
<220> FEATURE:
<223> OTHER INFORMATION: Peptide linker

<400> SEQUENCE: 171

Ser Met Asp Thr Ser Gln Leu
1               5

<210> SEQ ID NO 172

```
<211> LENGTH: 5
<212> TYPE: PRT
<213> ORGANISM: Artificial
<220> FEATURE:
<223> OTHER INFORMATION: Peptide linker

<400> SEQUENCE: 172

Gly Gly Gly Gly Ser
1               5

<210> SEQ ID NO 173
<211> LENGTH: 10
<212> TYPE: PRT
<213> ORGANISM: Artificial
<220> FEATURE:
<223> OTHER INFORMATION: Peptide linker

<400> SEQUENCE: 173

Gly Gly Gly Gly Ser Gly Gly Gly Gly Ser
1               5                   10

<210> SEQ ID NO 174
<211> LENGTH: 15
<212> TYPE: PRT
<213> ORGANISM: Artificial
<220> FEATURE:
<223> OTHER INFORMATION: Peptide linker

<400> SEQUENCE: 174

Gly Gly Gly Gly Ser Gly Gly Gly Gly Ser Gly Gly Gly Gly Ser
1               5                   10                  15

<210> SEQ ID NO 175
<211> LENGTH: 20
<212> TYPE: PRT
<213> ORGANISM: Artificial
<220> FEATURE:
<223> OTHER INFORMATION: Peptide linker

<400> SEQUENCE: 175

Gly Gly Gly Gly Ser Gly Gly Gly Gly Ser Gly Gly Gly Gly Ser Gly
1               5                   10                  15

Gly Gly Gly Ser
            20

<210> SEQ ID NO 176
<211> LENGTH: 25
<212> TYPE: PRT
<213> ORGANISM: Artificial
<220> FEATURE:
<223> OTHER INFORMATION: Peptide linker

<400> SEQUENCE: 176

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 177
<211> LENGTH: 30
<212> TYPE: PRT
<213> ORGANISM: Artificial
<220> FEATURE:
<223> OTHER INFORMATION: Peptide linker
```

```
<400> SEQUENCE: 177

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25                  30

<210> SEQ ID NO 178
<211> LENGTH: 49
<212> TYPE: PRT
<213> ORGANISM: Artificial
<220> FEATURE:
<223> OTHER INFORMATION: Synthetic peptide with protecting group

<400> SEQUENCE: 178

His Ser Asp Gly Ile Phe Thr Asp Ser Tyr Ser Ser Arg Tyr Arg Lys
1               5                   10                  15

Gln Met Ala Val Lys Lys Tyr Leu Ala Ala Val Leu Pro Gly Asn Ser
            20                  25                  30

Val Phe Lys Glu Cys Met Lys Gln Lys Lys Glu Phe Lys Ala Gly
        35                  40                  45

Lys

<210> SEQ ID NO 179
<211> LENGTH: 28
<212> TYPE: PRT
<213> ORGANISM: Artificial
<220> FEATURE:
<223> OTHER INFORMATION: Synthetic peptide with protecting group

<400> SEQUENCE: 179

His Ser Asp Gly Ile Phe Ala Pro Gly Asn Ser Val Phe Lys Glu Cys
1               5                   10                  15

Met Lys Gln Lys Lys Lys Glu Phe Lys Ala Gly Lys
            20                  25

<210> SEQ ID NO 180
<211> LENGTH: 35
<212> TYPE: PRT
<213> ORGANISM: Artificial
<220> FEATURE:
<223> OTHER INFORMATION: Synthetic peptide with protecting group

<400> SEQUENCE: 180

His Ser Asp Gly Ile Phe Thr Ser Met Asp Thr Ser Gln Leu Pro Gly
1               5                   10                  15

Asn Ser Val Phe Lys Glu Cys Met Lys Gln Lys Lys Glu Phe Lys
            20                  25                  30

Ala Gly Lys
        35

<210> SEQ ID NO 181
<211> LENGTH: 28
<212> TYPE: PRT
<213> ORGANISM: Artificial
<220> FEATURE:
<223> OTHER INFORMATION: Synthetic peptide with protecting group

<400> SEQUENCE: 181

His Ser Asp Gly Ile Phe Thr Pro Gly Asn Ser Val Phe Lys Glu Cys
1               5                   10                  15

Met Lys Gln Lys Lys Lys Glu Phe Lys Ala Gly Lys
            20                  25
```

PAC1 RECEPTOR AGONISTS (MAXCAPS) AND USES THEREOF

CROSS-REFERENCE TO RELATED APPLICATIONS

This application is a continuation of U.S. Ser. No. 16/473,240, filed on Jun. 24, 2019, which is a U.S. 371 National Phase of PCT/US2018/012405, filed on Jan. 4, 2018, which claims benefit of and priority to U.S. Ser. No. 62/442,906, filed on Jan. 5, 2017, each of which is incorporated herein by reference in its entirety for all purposes.

STATEMENT OF GOVERNMENTAL SUPPORT

This work was supported by the U.S. Department of Veterans Affairs, and the Federal Government has certain rights in the invention.

INCORPORATION BY REFERENCE OF SEQUENCE LISTING PROVIDED AS A TEXT FILE

A Sequence Listing is provided herewith as a text file, "UCLA-P176C1US_ST25.txt" created on Oct. 25, 2021 and having a size of 71,632 bytes. The contents of the text file are incorporated by reference herein in their entirety.

BACKGROUND

Pituitary Adenylate Cyclase Activating Polypeptide (PACAP) is a 27- or 38-amino acid peptide. The primary sequence of PACAP is 68% identical to its closest hormone relative, VIP. PACAP and VIP bind with the same affinity to VPAC1 and VPAC2 receptors, but only PACAP binds with a 1000-fold greater affinity to PAC1 receptor. PACAP and PAC1 immunoreactivities show a similar distribution pattern in the myenteric ganglia and in the nerve fibers, localized in the muscle layers of the gastrointestinal tract. The human PACAP gene (ADCYAP1) is localized to chromosome 18p11.32. The high affinity receptor for PACAP, PAC1 R, is localized to chromosome 7p14 in humans.

PACAP is widely distributed in the brain and peripheral organs, notably in the endocrine pancreas, gonads, respiratory and urogenital tracts. Molecular cloning of PACAP receptors has shown the existence of three distinct receptor subtypes: the PACAP-specific PAC1-R, which is coupled to several transduction systems, and the PACAP/VIP-indifferent VPAC1-R and VPAC2-R, which are primarily coupled to adenylyl cyclase. PAC1-Rs are particularly abundant in the brain, the pituitary and the adrenal gland, whereas VPACs receptors are expressed mainly in lung, liver, and testis. Consistent with the wide distribution of PACAP and its receptors, the peptide has now been shown to exert a large array of pharmacological effects and biological functions.

Several N-terminally shortened $PACAP_{27}$ or $PACAP_{38}$ peptides up to PACAP(9-27) or PACAP(9-38) have been observed to act as PAC1 receptor antagonists but, surprisingly, shorter fragments are agonists though with low potencies (Vandermeers et al. (1992) *Eur. J. Biochem.* 208: 815-819. Other findings have indicated that $PACAP_{27}$ and $PACAP_{38}$ differ in terms of their requirements of the amino acids in positions 4, 5, 9, 11 and 13 for maximal interaction with the PAC1 receptor (Schafer et al. (1999) *Regul. Pept.* 79: 83-92). C-terminally shortened $PACAP_{26}$ to $PACAP_{23}$ are full agonists with low potency which discriminate the three subtypes of PACAP receptors having the highest affinity for VPAC1, intermediate affinity for PAC1 and lowest affinity for VPAC2 (Gourlet et al. (1996) *Regul. Pept.* 62: 125-130). Maxadilan is a 61 amino acid peptide that is a potent and selective PAC1 receptor agonist and deletion of its 25-41 sequence results in a potent (Ki=3.9 nM) PAC1 receptor antagonist referred to as M65 (Uchida et al. (1998) *Ann. N.Y. Acad. Sci.* 865: 253-258). It has also been shown that deletion of the 19 amino acids between positions 24 and 42 in maxadilan results in a peptide with binding but no functional activity at the PAC1 receptor (Moro et al. (1999) *J. Biol. Chem.* 274: 23103-23110). This peptide referred to as [d.24-42]-GS-Maxadilan is a potent PAC1 receptor antagonist with a Ki~nM (Id.). Unlike $PACAP_{6-38}$ which interacts with VPAC1 and VPAC2 receptors, [d.24-42]-GS-Maxadilan appears to be highly specific for PAC1 receptor (Id.).

SUMMARY

During the course of our research on the effects of PACAP, VIP and their PAC1, VPAC1 and VPAC2 receptors on appetite/satiety regulation, metabolic syndrome, glucose metabolism, insulin resistance, pre-diabetic syndrome, diabetes type 2 (T2D), chronic inflammation, inflammatory bowel diseases, obesity and liver steatosis, we discovered that compounds that specifically bind and activate PAC1 receptors significantly increase satiety and body lean mass, while suppressing appetite, body fat mass and liver fat accumulation, blood glucose levels, chronic inflammation, improving hepatic steatosis, non-alcoholic steatohepatitis (NASH), non-alcoholic fatty liver disease (NAFLD) and colitis.

We have developed novel specific PAC1 receptor agonists, MAXCAP(s) that can be absorbed systemically to activate PAC1 receptors. These novel agonists were prepared by the identification of key amino acid residues of the native sequence of $PACAP_{1-27}$, $PACAP_{1-38}$ and the inclusion of amino acid sequences from the maxadilan peptide. Maxadilan and PACAP have no structural homology. In certain embodiments these PAC1 receptor agonists utilize the Maxadilan peptide or fragments thereof (e.g., Maxadilan N-terminus fragments (or variants thereof)) to specifically and exclusively bind to PAC1 receptor and fragments of the PACAP C-terminus to activate PAC1 signaling. Without being bound to a particular theory, it is believed that these PAC1 agonists are more resistant to DPP-IV protease degradation than the native $PACAP_{1-27}$ and $PACAP_{1-38}$ and thus have a longer half-life.

Accordingly, various embodiments contemplated herein may include, but need not be limited to, one or more of the following:

Embodiment 1: A PAC1 receptor agonist, said agonist comprising:
  a targeting sequence that binds to the PAC1 receptor attached to a peptide that activates PAC1 signaling, wherein:
    said targeting sequence comprises a maxadilan peptide or fragment thereof effective to bind a PAC1 receptor; and
    said peptide that activates PAC1 signaling comprises $PACAP_{1-38}$ or a fragment thereof, effective to activate PAC1 signaling, wherein said $PACAP_{1-38}$ or fragment thereof optionally comprises an amino acid deletion, insertion, or substitution.

Embodiment 2: The PAC1 receptor agonist of embodiment 1, wherein said $PACAP_{1-38}$ comprises an amino acid insertion between residues 11 and 12 of said $PACAP_{1-38}$.

Embodiment 3: The PAC1 receptor agonist according to any one of embodiments 1-2, wherein said PAC1 receptor agonist does not substantially activate the VPAC2 receptor or the PAC2 receptor.

Embodiment 4: The PAC1 receptor agonist according to any one of embodiments 1-2, wherein said PAC1 receptor agonist does not activate the VPAC2 receptor or the PAC2 receptor.

Embodiment 5: The PAC1 receptor agonist according to any one of embodiments 1-4, wherein said peptide that activates PAC1 signaling comprises an amino acid insertion between residues 11 and 12 of said PACP$_{1-38}$ peptide.

Embodiment 6: The PAC1 receptor agonist of embodiment 5, wherein said insertion is a serine or a threonine.

Embodiment 7: The PAC1 receptor agonist according to any one of embodiments 1-4, wherein said peptide that activates PAC1 signaling does not comprise an amino acid insertion between residues 11 and 12 of said PACP peptide.

Embodiment 8: The PAC1 receptor agonist according to any one of embodiments 1-7, wherein said peptide that activates PAC1 signaling comprise an R to A mutation at residue 12 of said PACP peptide.

Embodiment 9: The PAC1 receptor agonist according to any one of embodiments 1-7, wherein said peptide that activates PAC1 signaling comprise an R to K mutation at residue 12 of said PACP peptide.

Embodiment 10: The PAC1 receptor agonist according to any one of embodiments 1-7, wherein said peptide that activates PAC1 signaling comprise a K to A mutation at residue 15 of said PACP peptide.

Embodiment 11: The PAC1 receptor agonist according to any one of embodiments 1-4, wherein said peptide that activates PAC1 signaling comprises the amino acid sequence HSDGIF.

Embodiment 12: The PAC1 receptor agonist of embodiment 11, wherein said peptide that activates PAC1 signaling comprises the amino acid sequence HSDGIFT.

Embodiment 13: The PAC1 receptor agonist of embodiment 12, wherein said peptide that activates PAC1 signaling comprises the amino acid sequence HSDGIFTDSYSRYRKQMAVKKYLAAVL.

Embodiment 14: The PAC1 receptor agonist according to any one of embodiments 1-4, wherein said peptide that activates PAC1 signaling comprises the amino acid sequence HSDGIFTDSYSSRYRKQMAVKKYLAAVL.

Embodiment 15: The PAC1 receptor agonist of embodiment 7, wherein the amino acid sequence of said peptide that activates PAC1 signaling consists of an amino acid sequence selected from the group consisting of

```
                                      (SEQ ID NO: 95)
HSDGIFTDSYSRYRKQMAVKKYLAAVLGKRYKQRVKNK, (SEQ ID NO: 96)
HSDGIFTDSYSRYRKQMAVKKYLAAVLGKRYKQRVKN, (SEQ ID NO: 97)
HSDGIFTDSYSRYRKQMAVKKYLAAVLGKRYKQRVK, (SEQ ID NO: 98)
HSDGIFTDSYSRYRKQMAVKKYLAAVLGKRYKQRV, (SEQ ID NO: 99)
HSDGIFTDSYSRYRKQMAVKKYLAAVLGKRYKQR, (SEQ ID NO: 100)
HSDGIFTDSYSRYRKQMAVKKYLAAVLGKRYKQ, (SEQ ID NO: 101)
HSDGIFTDSYSRYRKQMAVKKYLAAVLGKRYK, (SEQ ID NO: 102)
HSDGIFTDSYSRYRKQMAVKKYLAAVLGKRY, (SEQ ID NO: 103)
HSDGIFTDSYSRYRKQMAVKKYLAAVLGKR, (SEQ ID NO: 104)
HSDGIFTDSYSRYRKQMAVKKYLAAVLGK, (SEQ ID NO: 105)
HSDGIFTDSYSRYRKQMAVKKYLAAVLG, (SEQ ID NO: 106)
HSDGIFTDSYSRYRKQMAVKKYLAAVL, (SEQ ID NO: 107)
HSDGIFTDSYSRYRKQMAVKKYLAAV, (SEQ ID NO: 108)
HSDGIFTDSYSRYRKQMAVKKYLAA, (SEQ ID NO: 109)
HSDGIFTDSYSRYRKQMAVKKYLA, (SEQ ID NO: 110)
HSDGIFTDSYSRYRKQMAVKKYL, (SEQ ID NO: 111)
HSDGIFTDSYSRYRKQMAVKKY, (SEQ ID NO: 112)
HSDGIFTDSYSRYRKQMAVKK, (SEQ ID NO: 113)
HSDGIFTDSYSRYRKQMAVK, (SEQ ID NO: 114)
HSDGIFTDSYSRYRKQMAV, (SEQ ID NO: 115)
HSDGIFTDSYSRYRKQMA, (SEQ ID NO: 116)
HSDGIFTDSYSRYRKQM, (SEQ ID NO: 117)
HSDGIFTDSYSRYRKQ, (SEQ ID NO: 118)
HSDGIFTDSYSRYRK, (SEQ ID NO: 119)
HSDGIFTDSYSRYRA, (SEQ ID NO: 120)
HSDGIFTDSYSRYR, (SEQ ID NO: 121)
HSDGIFTDSYSRY, (SEQ ID NO: 122)
HSDGIFTDSYSR, (SEQ ID NO: 123)
HSDGIFTDSYSA, (SEQ ID NO: 124)
HSDGIFTDSYSK, (SEQ ID NO: 125)
HSDGIFTDSYS, (SEQ ID NO: 126)
HSDGIFTDSY, (SEQ ID NO: 127)
HSDGIFTDS,
```

```
                                  (SEQ ID NO: 128)
HSDGIFTD, (SEQ ID NO: 129)
HSDGIFT,
and (SEQ ID NO: 130)
HSDGIF.
```

Embodiment 16: The PAC1 receptor agonist of embodiment 5, wherein the amino acid sequence of said peptide that activates PAC1 signaling consists of an amino acid sequence selected from the group consisting of

```
                                            (SEQ ID NO: 131)
HSDGIFTDSYSSRYRKQMAVKKYLAAVLGKRYKQRVKNK, (SEQ ID NO: 132)
HSDGIFTDSYSSRYRKQMAVKKYLAAVLGKRYKQRVKNK, (SEQ ID NO: 133)
HSDGIFTDSYSSRYRKQMAVKKYLAAVLGKRYKQRVKN, (SEQ ID NO: 134)
HSDGIFTDSYSSRYRKQMAVKKYLAAVLGKRYKQRVK, (SEQ ID NO: 135)
HSDGIFTDSYSSRYRKQMAVKKYLAAVLGKRYKQRV, (SEQ ID NO: 136)
HSDGIFTDSYSSRYRKQMAVKKYLAAVLGKRYKQR, (SEQ ID NO: 137)
HSDGIFTDSYSSRYRKQMAVKKYLAAVLGKRYKQ, (SEQ ID NO: 138)
HSDGIFTDSYSSRYRKQMAVKKYLAAVLGKRYK, (SEQ ID NO: 139)
HSDGIFTDSYSSRYRKQMAVKKYLAAVLGKRY, (SEQ ID NO: 140)
HSDGIFTDSYSSRYRKQMAVKKYLAAVLGKR, (SEQ ID NO: 141)
HSDGIFTDSYSSRYRKQMAVKKYLAAVLGK, (SEQ ID NO: 142)
HSDGIFTDSYSSRYRKQMAVKKYLAAVLG, (SEQ ID NO: 143)
HSDGIFTDSYSSRYRKQMAVKKYLAAVL, (SEQ ID NO: 144)
HSDGIFTDSYSSRYRKQMAVKKYLAAV, (SEQ ID NO: 145)
HSDGIFTDSYSSRYRKQMAVKKYLAA, (SEQ ID NO: 146)
HSDGIFTDSYSSRYRKQMAVKKYLA, (SEQ ID NO: 147)
HSDGIFTDSYSSRYRKQMAVKKYL, (SEQ ID NO: 148)
HSDGIFTDSYSSRYRKQMAVKKY, (SEQ ID NO: 149)
HSDGIFTDSYSSRYRKQMAVKK, (SEQ ID NO: 150)
HSDGIFTDSYSSRYRKQMAVK, (SEQ ID NO: 151)
HSDGIFTDSYSSRYRKQMAV, (SEQ ID NO: 152)
HSDGIFTDSYSSRYRKQMA, (SEQ ID NO: 153)
HSDGIFTDSYSSRYRKQM, (SEQ ID NO: 154)
HSDGIFTDSYSSRYRKQ, (SEQ ID NO: 155)
HSDGIFTDSYSSRYRK, (SEQ ID NO: 156)
HSDGIFTDSYSSRYR, (SEQ ID NO: 157)
HSDGIFTDSYSSRY, (SEQ ID NO: 158)
HSDGIFTDSYSSR,
and (SEQ ID NO: 159)
HSDGIFTDSYSS.
```

Embodiment 17: The PAC1 receptor agonist according to any one of embodiments 1-16, wherein said targeting sequence comprises the amino acid sequence PGNSVFKECMKQKKKEFKAGK (SEQ ID NO:4), optimally with one, two, or three amino acid substitutions therein.

Embodiment 18: The PAC1 receptor agonist according to any one of embodiments 1-16, wherein said targeting sequence comprises the amino acid sequence

```
                                            (SEQ ID NO: 4)
PGNSVFKECMKQKKKEFKAGK.
```

Embodiment 19: The PAC1 receptor agonist according to any one of embodiments 1-16, wherein said targeting sequence consists of the amino acid sequence

```
                                            (SEQ ID NO: 4)
PGNSVFKECMKQKKKEFKAGK.
```

Embodiment 20: The PAC1 receptor agonist according to any one of embodiments 1-16, wherein the amino acid sequence of said targeting sequence consists of an amino acid sequence selected from the group consisting of

```
                                            (SEQ ID NO: 26)
MKQILLISLVVVLAVFAFNVAEGCDATCQFRKAIDDCQKQAHHSNVLQTS

VQTTATFTSMDTSQLPGNSVFKECMKQKKKEFSSGK, (SEQ ID NO: 27)
KQILLISLVVVLAVFAFNVAEGCDATCQFRKAIDDCQKQAHHSNVLQTSV

QTTATFTSMDTSQLPGNSVFKECMKQKKKEFSSGK, (SEQ ID NO: 28)
QILLISLVVVLAVFAFNVAEGCDATCQFRKAIDDCQKQAHHSNVLQTSVQ

TTATFTSMDTSQLPGNSVFKECMKQKKKEFSSGK, (SEQ ID NO: 29)
ILLISLVVVLAVFAFNVAEGCDATCQFRKAIDDCQKQAHHSNVLQTSVQT

TATFTSMDTSQLPGNSVFKECMKQKKKEFSSGK, (SEQ ID NO: 30)
LLISLVVVLAVFAFNVAEGCDATCQFRKAIDDCQKQAHHSNVLQTSVQTT

ATFTSMDTSQLPGNSVFKECMKQKKKEFSSGK,
```

-continued (SEQ ID NO: 31)
LISLVVVLAVFAFNVAEGCDATCQFRKAIDDCQKQAHHSNVLQTSVQTTA
TFTSMDTSQLPGNSVFKECMKQKKKEFSSGK, (SEQ ID NO: 32)
ISLVVVLAVFAFNVAEGCDATCQFRKAIDDCQKQAHHSNVLQTSVQTTAT
FTSMDTSQLPGNSVFKECMKQKKKEFSSGK, (SEQ ID NO: 33)
SLVVVLAVFAFNVAEGCDATCQFRKAIDDCQKQAHHSNVLQTSVQTTATF
TSMDTSQLPGNSVFKECMKQKKKEFSSGK, (SEQ ID NO: 34)
LVVVLAVFAFNVAEGCDATCQFRKAIDDCQKQAHHSNVLQTSVQTTATFT
SMDTSQLPGNSVFKECMKQKKKEFSSGK, (SEQ ID NO: 35)
VVVLAVFAFNVAEGCDATCQFRKAIDDCQKQAHHSNVLQTSVQTTATFTS
MDTSQLPGNSVFKECMKQKKKEFSSGK, (SEQ ID NO: 36)
VVLAVFAFNVAEGCDATCQFRKAIDDCQKQAHHSNVLQTSVQTTATFTSM
DTSQLPGNSVFKECMKQKKKEFSSGK, (SEQ ID NO: 37)
VLAVFAFNVAEGCDATCQFRKAIDDCQKQAHHSNVLQTSVQTTATFTSMD
TSQLPGNSVFKECMKQKKKEFSSGK, (SEQ ID NO: 38)
LAVFAFNVAEGCDATCQFRKAIDDCQKQAHHSNVLQTSVQTTATFTSMDT
SQLPGNSVFKECMKQKKKEFSSGK, (SEQ ID NO: 39)
AVFAFNVAEGCDATCQFRKAIDDCQKQAHHSNVLQTSVQTTATFTSMDTS
QLPGNSVFKECMKQKKKEFSSGK, (SEQ ID NO: 40)
VFAFNVAEGCDATCQFRKAIDDCQKQAHHSNVLQTSVQTTATFTSMDTSQ
LPGNSVFKECMKQKKKEFSSGK, (SEQ ID NO: 41)
FAFNVAEGCDATCQFRKAIDDCQKQAHHSNVLQTSVQTTATFTSMDTSQL
PGNSVFKECMKQKKKEFSSGK, (SEQ ID NO: 42)
AFNVAEGCDATCQFRKAIDDCQKQAHHSNVLQTSVQTTATFTSMDTSQLP
GNSVFKECMKQKKKEFSSGK, (SEQ ID NO: 43)
FNVAEGCDATCQFRKAIDDCQKQAHHSNVLQTSVQTTATFTSMDTSQLPG
NSVFKECMKQKKKEFSSGK, (SEQ ID NO: 44)
NVAEGCDATCQFRKAIDDCQKQAHHSNVLQTSVQTTATFTSMDTSQLPGN
SVFKECMKQKKKEFSSGK, (SEQ ID NO: 45)
VAEGCDATCQFRKAIDDCQKQAHHSNVLQTSVQTTATFTSMDTSQLPGNS
VFKECMKQKKKEFSSGK, (SEQ ID NO: 46)
AEGCDATCQFRKAIDDCQKQAHHSNVLQTSVQTTATFTSMDTSQLPGNSV
FKECMKQKKKEFSSGK, (SEQ ID NO: 47)
EGCDATCQFRKAIDDCQKQAHHSNVLQTSVQTTATFTSMDTSQLPGNSVF
KECMKQKKKEFSSGK, (SEQ ID NO: 48)
GCDATCQFRKAIDDCQKQAHHSNVLQTSVQTTATFTSMDTSQLPGNSVFK
ECMKQKKKEFSSGK, (SEQ ID NO: 49)
CDATCQFRKAIDDCQKQAHHSNVLQTSVQTTATFTSMDTSQLPGNSVFKE
CMKQKKKEFSSGK, (SEQ ID NO: 50)
DATCQFRKAIDDCQKQAHHSNVLQTSVQTTATFTSMDTSQLPGNSVFKEC
MKQKKKEFSSGK, (SEQ ID NO: 51)
ATCQFRKAIDDCQKQAHHSNVLQTSVQTTATFTSMDTSQLPGNSVFKECM
KQKKKEFSSGK, (SEQ ID NO: 52)
TCQFRKAIDDCQKQAHHSNVLQTSVQTTATFTSMDTSQLPGNSVFKECMK
QKKKEFSSGK, (SEQ ID NO: 53)
CQFRKAIDDCQKQAHHSNVLQTSVQTTATFTSMDTSQLPGNSVFKECMKQ
KKKEFSSGK, (SEQ ID NO: 54)
QFRKAIDDCQKQAHHSNVLQTSVQTTATFTSMDTSQLPGNSVFKECMKQK
KKEFSSGK, (SEQ ID NO: 55)
FRKAIDDCQKQAHHSNVLQTSVQTTATFTSMDTSQLPGNSVFKECMKQKK
KEFSSGK, (SEQ ID NO: 56)
RKAIDDCQKQAHHSNVLQTSVQTTATFTSMDTSQLPGNSVFKECMKQKKK
EFSSGK, (SEQ ID NO: 57)
KAIDDCQKQAHHSNVLQTSVQTTATFTSMDTSQLPGNSVFKECMKQKKKE
FSSGK, (SEQ ID NO: 58)
AIDDCQKQAHHSNVLQTSVQTTATFTSMDTSQLPGNSVFKECMKQKKKEF
SSGK, (SEQ ID NO: 59)
IDDCQKQAHHSNVLQTSVQTTATFTSMDTSQLPGNSVFKECMKQKKKEFS
SGK, (SEQ ID NO: 60)
DDCQKQAHHSNVLQTSVQTTATFTSMDTSQLPGNSVFKECMKQKKKEFSS
GK, (SEQ ID NO: 61)
DCQKQAHHSNVLQTSVQTTATFTSMDTSQLPGNSVFKECMKQKKKEFSSG
K, (SEQ ID NO: 62)
CQKQAHHSNVLQTSVQTTATFTSMDTSQLPGNSVFKECMKQKKKEFSSGK, -continued

```
                                      (SEQ ID NO: 63)
QKQAHHSNVLQTSVQTTATFTSMDTSQLPGNSVFKECMKQKKKEFSSGK, (SEQ ID NO: 64)
KQAHHSNVLQTSVQTTATFTSMDTSQLPGNSVFKECMKQKKKEFSSGK, (SEQ ID NO: 65)
QAHHSNVLQTSVQTTATFTSMDTSQLPGNSVFKECMKQKKKEFSSGK, (SEQ ID NO: 66)
AHHSNVLQTSVQTTATFTSMDTSQLPGNSVFKECMKQKKKEFSSGK, (SEQ ID NO: 67)
HHSNVLQTSVQTTATFTSMDTSQLPGNSVFKECMKQKKKEFSSGK, (SEQ ID NO: 68)
HSNVLQTSVQTTATFTSMDTSQLPGNSVFKECMKQKKKEFSSGK, (SEQ ID NO: 69)
SNVLQTSVQTTATFTSMDTSQLPGNSVFKECMKQKKKEFSSGK, (SEQ ID NO: 70)
NVLQTSVQTTATFTSMDTSQLPGNSVFKECMKQKKKEFSSGK, (SEQ ID NO: 71)
VLQTSVQTTATFTSMDTSQLPGNSVFKECMKQKKKEFSSGK, (SEQ ID NO: 72)
LQTSVQTTATFTSMDTSQLPGNSVFKECMKQKKKEFSSGK, (SEQ ID NO: 73)
QTSVQTTATFTSMDTSQLPGNSVFKECMKQKKKEFSSGK, (SEQ ID NO: 74)
TSVQTTATFTSMDTSQLPGNSVFKECMKQKKKEFSSGK, (SEQ ID NO: 75)
SVQTTATFTSMDTSQLPGNSVFKECMKQKKKEFSSGK, (SEQ ID NO: 76)
VQTTATFTSMDTSQLPGNSVFKECMKQKKKEFSSGK, (SEQ ID NO: 77)
QTTATFTSMDTSQLPGNSVFKECMKQKKKEFSSGK, (SEQ ID NO: 78)
TTATFTSMDTSQLPGNSVFKECMKQKKKEFSSGK, (SEQ ID NO: 79)
GNSVFKECMKQKKKEFSSGK, (SEQ ID NO: 80)
NSVFKECMKQKKKEFSSGK, (SEQ ID NO: 81)
SVFKECMKQKKKEFSSGK, (SEQ ID NO: 82)
VFKECMKQKKKEFSSGK, (SEQ ID NO: 83)
FKECMKQKKKEFSSGK, (SEQ ID NO: 84)
KECMKQKKKEFSSGK, (SEQ ID NO: 85)
ECMKQKKKEFSSGK, (SEQ ID NO: 86)
CMKQKKKEFSSGK, (SEQ ID NO: 87)
MKQKKKEFSSGK, (SEQ ID NO: 88)
KQKKKEFSSGK, (SEQ ID NO: 89)
QKKKEFSSGK,
```

-continued

```
                                      (SEQ ID NO: 90)
KKKEFSSGK, (SEQ ID NO: 91)
KKEFSSGK, (SEQ ID NO: 92)
KEFSSGK, (SEQ ID NO: 93)
EFSSGK,
and
                                      (SEQ ID NO: 94)
FSSGK.
```

Embodiment 21: The PAC1 receptor agonist according to any one of embodiments 1-16, wherein the amino acid sequence of said targeting sequence comprises a mutation at one or more positions corresponding to one or more of N45, K49, P43, D38, E50, K53, and/or K55 of the full-length maxadilan peptide.

Embodiment 22: The PAC1 receptor agonist of embodiment 21, wherein said targeting sequence comprises one or more mutations selected from the group consisting of N45A, K49A, P43A, D38A, E50A, K53A, and K55A.

Embodiment 23: The PAC1 receptor agonist according to any one of embodiments 1-22, wherein said fragment of the maxadilan amino acid sequence is chemically conjugated to said targeting sequence.

Embodiment 24: The PAC1 receptor agonist of embodiment 23, wherein said fragment of the maxadilan amino acid sequence is chemically conjugated to the amino terminus of said targeting sequence.

Embodiment 25: The PAC1 receptor agonist of embodiment 23, wherein said fragment of the maxadilan amino acid sequence is chemically conjugated to the carboxy terminus of said targeting sequence.

Embodiment 26: The PAC1 receptor agonist according to any one of embodiments 23-25, wherein said fragment of the maxadilan amino acid sequence is chemically conjugated to said targeting sequence via a linker comprising a polyethylene glycol (PEG).

Embodiment 27: The PAC1 receptor agonist according to any one of embodiments 23-25, wherein said fragment of the maxadilan amino acid sequence is chemically conjugated to said targeting sequence via a linker comprising human serum albumin (HSA).

Embodiment 28: The PAC1 receptor agonist according to any one of embodiments 23-25, wherein said fragment of the maxadilan amino acid sequence is chemically conjugated to said targeting sequence via a non-peptide linker found in Table 6.

Embodiment 29: The PAC1 receptor agonist according to any one of embodiments 1-22, wherein said fragment of the maxadilan amino acid sequence attached directly or through an amino acid, or through a peptide linker to said targeting sequence and said PAC1 receptor agonist is a fusion peptide.

Embodiment 30: The PAC1 receptor agonist of embodiment 29, wherein said fragment of the maxadilan amino acid sequence is attached directly to said targeting sequence.

Embodiment 31: The PAC1 receptor agonist of embodiment 29, wherein said fragment of the maxadilan amino acid sequence is attached through an amino acid to said targeting sequence.

Embodiment 32: The PAC1 receptor agonist of embodiment 31, wherein said amino acid is selected from the group consisting of alanine (A), glycine (G), and proline (P).

Embodiment 33: The PAC1 receptor agonist of embodiment 32, wherein said amino acid is alanine.

Embodiment 34: The PAC1 receptor agonist of embodiment 29, wherein said fragment of the maxadilan amino acid sequence is attached through a peptide linker to said targeting sequence.

Embodiment 35: The PAC1 receptor agonist of embodiment 34, wherein the amino acid sequence of said linker comprises a sequence selected from the group consisting of GG, PP, GGG, PPP, GGGG (SEQ ID NO:164), GGGGS (SEQ ID NO:172), and SMDTSQL (SEQ ID NO:171).

Embodiment 36: The PAC1 receptor agonist of embodiment 35, wherein the amino acid sequence of said peptide linker comprises or consists of the sequence SMDTSQL (SEQ ID NO:171).

Embodiment 37: The PAC1 receptor agonist according to any one of embodiments 29-36, wherein said fragment of the maxadilan amino acid sequence is attached directly, or through an amino acid, or through a peptide linker to the amino terminal of said targeting sequence.

Embodiment 38: The PAC1 receptor agonist according to any one of embodiments 29-36, wherein said fragment of the maxadilan amino acid sequence is attached directly, or through an amino acid, or through a peptide linker to the carboxyl terminal of said targeting sequence.

Embodiment 39: The PAC1 receptor agonist of embodiment 29, wherein the amino acid sequence of said agonist comprises or consists of the amino acid sequence (SEQ ID NO: 5)
HSDGIFTDSYSSRYRKQMAVKKYLAAVLPGNSVFKECMKQKKKEFKAGK.

Embodiment 40: The PAC1 receptor agonist of embodiment 29, wherein the amino acid sequence of said agonist comprises or consists of the amino acid sequence (SEQ ID NO: 6)
HSDGIFAPGNSVFKECMKQKKKEFKAGK.

Embodiment 41: The PAC1 receptor agonist of embodiment 29, wherein the amino acid sequence of said agonist comprises or consists of the amino acid sequence (SEQ ID NO: 7)
HSDGIFTSMDTSQLPGNSVFKECMKQKKKEFKAGK.

Embodiment 42: The PAC1 receptor agonist of embodiment 29, wherein the amino acid sequence of said agonist comprises or consists of the amino acid sequence (SEQ ID NO: 8)
HSDGIFTPGNSVFKECMKQKKKEFKAGK.

Embodiment 43: The PAC1 receptor agonist of embodiment 29, wherein the amino acid sequence of said agonist comprises or consists of the amino acid sequence (SEQ ID NO: 9)
HSDGIFTDSYSA PGNSVFKECMKQKKKEFKAGK.

Embodiment 44: The PAC1 receptor agonist of embodiment 29, wherein the amino acid sequence of said agonist comprises or consists of the amino acid sequence (SEQ ID NO: 10)
HSDGIFTDSYSK PGNSVFKECMKQKKKEFKAGK.

Embodiment 45: The PAC1 receptor agonist of embodiment 29, wherein the amino acid sequence of said agonist comprises or consists of the amino acid sequence (SEQ ID NO: 11)
HSDGIFTDSYSRYRA PGNSVFKECMKQKKKEFKAGK.

Embodiment 46: The PAC1 receptor agonist of embodiment 29, wherein the amino acid sequence of said agonist comprises or consists of the amino acid sequence (SEQ ID NO: 12)
HSDGIFTDSYSRYRK PGNSVFKECMKQKKKEFKAGK.

Embodiment 47: The PAC1 receptor agonist according to any one of embodiments 1-46, wherein said agonist is more resistant to DPP-IV protease degradation than native $PACAP_{1-27}$ and/or $PACAP_{1-38}$.

Embodiment 48: The PAC1 receptor agonist of embodiments 1-47, wherein said PAC1 receptor agonist bears one or more protecting groups.

Embodiment 49: The PAC1 receptor agonist of embodiment 48, wherein said one or more protecting groups are independently selected from the group consisting of acetyl, amide, 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bon)), t-butoxycarbonyl (Boc), cyclohexyloxy (cHxO), t-butoxymethyl (Bum), t-butoxy (tBuO), t-Butyl (tBu), and Trifluoroacetyl (TFA).

Embodiment 50: The PAC1 receptor agonist of embodiment 48, wherein said construct comprises a protecting group at a carboxyl and/or amino terminus.

Embodiment 51: The PAC1 receptor agonist of embodiment 50, wherein a carboxyl terminus is amidated.

Embodiment 52: The PAC1 receptor agonist according to any one of embodiments 50-51, wherein an amino terminus is acetylated.

Embodiment 53: The PAC1 receptor agonist according to any one of embodiments 1-52, wherein said PAC1 receptor agonist is functionalized with a polymer to increase serum half-life.

Embodiment 54: The PAC1 receptor agonist of embodiment 53, wherein said polymer comprises polyethylene glycol and/or a cellulose or modified cellulose.

Embodiment 55: The PAC1 receptor agonist according to any one of embodiments 1-54, wherein said targeting sequence, and/or said peptide that activates PAC1 signaling is recombinantly expressed.

Embodiment 56: The PAC1 receptor agonist according to any one of embodiments 1-55, wherein said targeting sequence, and/or said peptide that activates PAC1 signaling is glycosylated.

Embodiment 57: The PAC1 receptor agonist according to any one of embodiments 1-56, wherein said PAC1 receptor agonist, when administered to a mammal, is effective to:
- downregulate appetite and/or reduce obesity, and/or body weight; and/or
- inhibit adipogenesis and/or fat accumulation; and/or
- ameliorate one or more symptoms of, or slow the progression of, or prevent type 2 diabetes; and/or
- ameliorate one or more symptoms of atherosclerosis; and/or slow the progression of, or prevent, or reverse non-alcoholic fatty liver disease (NAFLD); and/or
- ameliorate one or more symptoms of, and/or slow, and/or prevent, and/or reverse hepatosteatosis (fatty liver); and/or
- ameliorate one or more symptoms of, and/or slow the progression of, and/or prevent, and/or reverse metabolic syndrome; and/or
- ameliorate one or more symptoms of, and/or slow the progression of, and/or prevent, and/or reverse insulin resistance; and/or
- ameliorate one or more symptoms of, and/or slow the progression of, and/or prevent, and/or reverse prediabetic syndrome.

Embodiment 58: A pharmaceutical composition comprising a PAC1 receptor agonist according to any of embodiments 1-57 in a pharmaceutically acceptable carrier.

Embodiment 59: The composition of embodiment 58, wherein said composition is formulated as a unit dosage formulation.

Embodiment 60: The composition according to any one of embodiments 58-59, wherein said composition is formulated for administration by a modality selected from the group consisting of intraperitoneal administration, topical administration, oral administration, inhalation administration, transdermal administration, subdermal depot administration, and rectal administration.

Embodiment 61: A method of performing one or more of the following in a mammal:
- downregulating appetite and/or reducing obesity and/or to reducing body weight; and/or
- inhibiting adipogenesis and/or body fat accumulation; and/or
- reducing and/or regulating glucose homeostasis; and/or
- improving or curing diabetes mellitus symptoms; and/or
- reducing or curing e inflammatory bowel diseases; and/or
- reducing or cure chronic inflammatory diseases; and/or
- ameliorating symptoms of and/or to treat systemic and organ-specific autoimmune diseases; and/or
- reducing or cure dry eye syndrome; and/or
- preventing or reducing organ, tissue, and/or stem cell transplant rejection; and/or
- improving embryo implant in uterus for in vitro fertilization; and/or
- ameliorating spermatogenesis and/or male infertility; and/or
- ameliorating female ovulation and/or female fertility; and/or
- ameliorating one or more symptoms of connectivitis; and/or
- slowing the progression of osteoarthritis and/or rheumatoid arthritis, and/or psoriatic arthritis; and/or
- preventing, or reversing systemic hypertension; and/or
- ameliorating one or more symptoms of atherosclerosis; and/or
- slowing the progression of, or preventing, or reversing non-alcoholic fatty liver disease (NAFLD), and/or NASH; and/or
- ameliorating one or more symptoms of, and/or slowing, and/or preventing, and/or reversing hepatosteatosis (fatty liver); and/or
- ameliorating one or more symptoms of, and/or slowing the progression of, and/or preventing, and/or to reversing metabolic syndrome;
- and/or ameliorating one or more symptoms of, and/or slowing the progression of, and/or preventing, and/or reversing insulin resistance; and/or
- ameliorating one or more symptoms of, and/or slowing the progression of, and/or preventing, and/or reversing prediabetic syndrome; and/or
- slowing the progression of, and/or preventing, and/or reversing renal hypertension and/or chronic kidney diseases; and/or
- slowing the progression of, and/or to inhibiting, and/or reversing growth of tumors expressing PAC1 receptors; and/or
- slowing the progression of, and/or preventing, and/or reversing mast cell and/or basophil degranulation and release of allergic mediators; and/or
- ameliorating the symptoms of, and/or treating cystic fibrosis; and/or
- ameliorating the symptoms of, and/or treating celiac disease; and/or
- slowing the progression of, and/or preventing, and/or reversing schizophrenic and paranoid disorders; and/or
- slowing the progression of, and/or preventing, and/or reversing Alzheimer's disease; and/or
- slowing the progression of, and/or ameliorating the symptoms, and/or reversing neuromuscular dystrophy; and/or
- slowing the progression of, and/or preventing, and/or reversing neurological paralysis; and/or
- slowing the progression of, and/or ameliorating the symptoms of nerve injury paralysis; and/or
- slowing the progression of, and/or ameliorating the symptoms of, and/or reversing traumatic brain injury; and/or
- ameliorating the symptoms of, and/or reversing post traumatic stress disorder; and/or
- ameliorating the symptoms of, and/or reversing neuropathic disorders; and/or
- ameliorating the symptoms of, and/or slowing or reversing asthmatic syndrome; and/or
- ameliorating the symptoms of, and/or slowing or reversing chronic obstructive pulmonary disease; and/or
- ameliorating the symptoms of, and/or slowing or reversing lymphoproliferative disorders, and/or myeloproliferative disorders; and/or
- ameliorating the symptoms of, and/or slowing or reversing thrombocytopenia; and/or
- ameliorating the symptoms of, and/or treating multiple myeloma; and/or
- ameliorating the symptoms of, and/or slowing or reversing acute or chronic nephropathies; and/or
- treating transient arterial stenosis and/or hemorrhagic shock; and/or
- treating antibiotic induced nephrotoxicity; and/or
- ameliorating the symptoms of, and/or treating polycystic kidney disease; and/or
- ameliorating the symptoms of, and/or reversing ocular hypertension, and/or glaucoma, and/or retinitis pigmentosa; and/or
- ameliorating the symptoms of, and/or preventing ischemia/reperfusion of tissue and/or organs; and/or
- ameliorating the symptoms of, and/or preventing chronic pulmonary fibrotic processes; and/or ameliorating the symptoms of, and/or reversing or slowing the progression of cancer and metastases;

wherein said method comprises administering to said mammal an effective amount of one or more PAC1 receptor agonists according to any one of embodiments 1-57, and/or a pharmaceutical formulation according to any one of embodiments 58-60.

Embodiment 62: The method of embodiment 61, wherein said mammal is a human.

Embodiment 63: The method of embodiment 61, wherein said mammal is a non-human mammal.

Embodiment 64: The method according to any one of embodiments 61-63, wherein said mammal is diagnosed as clinically obese.

Embodiment 65: The method according to any one of embodiments 61-63, wherein said mammal is diagnosed as clinically obese.

Embodiment 66: The method according to any one of embodiments 61-63, wherein said mammal is diagnosed as having type 2 diabetes.

Embodiment 67: The method according to any one of embodiments 61-63, wherein said mammal is diagnosed as having atherosclerosis.

Embodiment 68: The method according to any one of embodiments 61-63, wherein said mammal is diagnosed as having fatty liver disease (NAFLD).

Embodiment 69: The method according to any one of embodiments 61-63, wherein said mammal is diagnosed as having NASH.

Embodiment 70: The method according to any one of embodiments 61-63, wherein said mammal is diagnosed as having hepatosteatosis (fatty liver).

Embodiment 71: The method according to any one of embodiments 61-63, wherein said mammal is diagnosed as having metabolic syndrome.

Embodiment 72: The method according to any one of embodiments 61-63, wherein said mammal is diagnosed as having insulin resistance.

Embodiment 73: The method according to any one of embodiments 61-63, wherein said mammal is diagnosed as having prediabetic syndrome.

Embodiment 74: The method according to any one of embodiments 61-63, wherein said mammal is diagnosed as having hepatosteatosis.

Embodiment 75: The method according to any one of embodiments 61-74, wherein said PAC1 receptor agonist and/or pharmaceutical formulation is administered in conjunction with one or more dipeptidyl peptidase-IV (DPP-IV) inhibitors.

Embodiment 76: The method of embodiment 75, wherein said dipeptidyl peptidase-IV inhibitor is selected from the group consisting of aminomethylpyridine, NVP DPP728, PSN9301, isoleucine thiazolidide, denagliptin, sitagliptin, vidagliptin, saxgliptin, alogliptin, NN-7201, and ALS 2-0426.

Embodiment 77: The method of embodiment 75, wherein said dipeptidyl peptidase-IV inhibitor comprises sitagliptin.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. In certain embodiments a targeting sequence (that binds a PAC1 receptor) described herein ranges in length up to about 60 aa, or up to about 50 aa, or up to about 40 aa, or up to about 38 aa, or up to about 30 aa, or up to about 27 aa, or up to about 25 aa, or up to about 20 aa, or up to about 15 aa, or up to about 10 aa. In certain embodiments a maxadilan sequence or a sequence comprising a maxadilan sequence (that binds a PAC1 receptor) described herein ranges in length up to 61 aa, or up to 60 aa, or up to about 55 aa, or up to about 50 aa, or up to about 40 aa, or up to about 30 aa, or up to about 21 aa, or up to about 15 aa. In certain embodiments fusion proteins comprising a sequence that binds a PAC1 receptor attached to an amino acid sequence that activates a PAC1 receptor (e.g., a MAXCAP compound) described herein ranges in length up to about 120 aa, or up to about 110 aa, or up to about 100 aa, or up to about 99 aa, or up to about 90 aa, or up to about 80 aa, or up to about 70 aa, or up to about 60 aa, or up to about 50 aa. In certain embodiments the amino acid residues comprising the PAC1 receptor agonists are "L-form" amino acid residues, however, it is recognized that in various embodiments, "D" amino acids can be incorporated. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, phosphonamide, carbomate, hydroxylate, and the like (see, e.g., Spatola, (1983) Chem. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "residue" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, and the like. These modified amino acids are illustrative and not intended to be limiting.

The term(s) "fusion protein" or "fusion peptide" refers to protein/peptide constructs in which two or more proteins/peptides (or fragments thereof, or sequences having substantial sequence identity to (e.g., greater than 80%, or greater than about 90%, or greater than about 95%, or greater than about 98%, or greater than about 99%)) that typically exist separately in nature are joined directly or through an amino acid, or through a peptide linker, to form a single contiguous peptide/protein. In various embodiments, the fusion protein can be chemically synthesized, or recombinantly expressed.

"β-peptides" comprise of "β amino acids", which have their amino group bonded to the β carbon rather than the α-carbon as in the 20 standard biological amino acids. The only commonly naturally occurring β amino acid is β-alanine.

Peptoids, or N-substituted glycines, are a specific subclass of peptidomimetics. They are closely related to their natural peptide counterparts, but differ chemically in that their side chains are appended to nitrogen atoms along the molecule's backbone, rather than to the α-carbons (as they are in natural amino acids).

The terms "conventional" and "natural" as applied to peptides herein refer to peptides, constructed only from the naturally-occurring amino acids: Ala, Cys, Asp, Glu, Glu, Phe, Gly, His, Ile, Lys, Leu, Met, Asn, Pro, Gln, Arg, Ser, Thr, Val, Trp, and Tyr. A compound of the invention "corresponds" to a natural peptide if it elicits a biological activity (e.g., antimicrobial activity) related to the biological activity and/or specificity of the naturally occurring peptide. The elicited activity may be the same as, greater than or less than that of the natural peptide. In general, such a peptoid will have an essentially corresponding monomer sequence, where a natural amino acid is replaced by an N-substituted glycine derivative, if the N-substituted glycine derivative resembles the original amino acid in hydrophilicity, hydrophobicity, polarity, etc. The following are illustrative, but non-limiting N-substituted glycine replacements: N-(1-methylprop-1-yl)glycine substituted for isoleucine (Ile), N-(prop-2-yl)glycine for valine (Val), N-benzylglycine for phenylanlaine (Phe), N-(2-hydroxyethyl)glycine for serine (Ser), and the like. In certain embodiments substitutions need not be "exact". Thus for example, in certain embodiments N-(2-hydroxyethyl)glycine may substitute for Ser, Thr, Cys, and/or Met; N-(2-methylprop-1-yl)glycine may substitute for Val, Leu, and/or Ile. In certain embodiments N-(2-hydroxyethyl)glycine can be used to substitute for Thr and Ser, despite the structural differences: the side chain in N-(2-hydroxyethyl)glycine is one methylene group longer than that of Ser, and differs from Thr in the site of hydroxy-substitution. In general, one may use an N-hydroxyalkyl-substituted glycine to substitute for any polar amino acid, an N-benzyl- or N-aralkyl-substituted glycine to replace any aromatic amino acid (e.g., Phe, Trp, etc.), an N-alkyl-substituted glycine such as N-butylglycine to replace any nonpolar amino acid (e.g., Leu, Val, Ile, etc.), and an N-(aminoalkyl)glycine derivative to replace any basic polar amino acid (e.g., Lys and Arg).

Where an amino acid sequence is provided herein, L-, D-, or beta amino acid versions of the sequence are also contemplated as well as retro, inversion, and retro-inversion isoforms. In addition, conservative substitutions (e.g., in the targeting sequences that bind the PAC1 receptor and/or maxadilan sequences that activate the PAC1 receptor and/or fusion proteins comprising both sequences) are contemplated. Non-protein backbones, such as PEG, alkane, ethylene bridged, ester backbones, and other backbones are also contemplated. Also fragments ranging in length from about 5, 6, 7, 8, 9, 10, 11, 12, 13, 14, 15, 16, 17, 18, 19, 20, 21, 22, 23, 24, or 25 amino acids up to the full length minus one amino acid of the peptide are contemplated where the fragment retains at least 50%, preferably at least 60% 70% or 80%, more preferably at least 90%, 95%, 98%, 99%, or at least 100% of the activity (e.g., binding specificity and/or avidity, antimicrobial activity, etc.) of the full length peptide are contemplated.

In certain embodiments, conservative substitutions of the amino acids comprising any of the sequences described herein are contemplated. In various embodiments one, two, three, four, or five different residues are substituted. The term "conservative substitution" is used to reflect amino acid substitutions that do not substantially alter the activity (e.g., antimicrobial activity and/or specificity) of the molecule. Typically, conservative amino acid substitutions involve substitution one amino acid for another amino acid with similar chemical properties (e.g. charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors. Examples of such "analog substitutions" include, but are not limited to, 1) Lys-Orn, 2) Leu-Norleucine, 3) Lys-Lys[TFA], 4) Phe-Phe[Gly], and 5) δ-amino butylglycine-ξ-amino hexylglycine, where Phe[gly] refers to phenylglycine (a Phe derivative with a H rather than $CH_3$ component in the R group), and Lys[TFA] refers to a Lys where a negatively charged ion (e.g., TFA) is attached to the amine R group. Other conservative substitutions include "functional substitutions" where the general chemistries of the two residues are similar, and can be sufficient to mimic or partially recover the function of the native peptide. Strong functional substitutions include, but are not limited to 1) Gly/Ala, 2) Arg/Lys, 3) Ser/Tyr/Thr, 4) Leu/Ile/Val, 5) Asp/Glu, 6) Gln/Asn, and 7) Phe/Trp/Tyr, while other functional substitutions include, but are not limited to 8) Gly/Ala/Pro, 9) Tyr/His, 10) Arg/Lys/His, 11) Ser/Thr/Cys, 12) Leu/Ile/Val/Met, and 13) Met/Lys (special case under hydrophobic conditions). Various "broad conservative substations" include substitutions where amino acids replace other amino acids from the same biochemical or biophysical grouping. This is similarity at a basic level and stems from efforts to classify the original 20 natural amino acids. Such substitutions include 1) nonpolar side chains: Gly/Ala/Val/Leu/Ile/Met/Pro/Phe/Trp, and/or 2) uncharged polar side chains Ser/Thr/Asn/Gln/Tyr/Cys. In certain embodiments, broad-level substitutions can also occur as paired substitutions. For example, Any hydrophilic neutral pair [Ser, Thr, Gln, Asn, Tyr, Cys]+[Ser, Thr, Gln, Asn, Tyr, Cys] can may be replaced by a charge-neutral charged pair [Arg, Lys, His]+[Asp, Glu]. The following six groups each contain amino acids that, in certain embodiments, are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W). Where amino acid sequences are disclosed herein, amino acid sequences comprising, one or more of the above-identified conservative substitutions are also contemplated.

In certain embodiments, targeting sequences that bind the PAC1 receptor and/or sequences that activate the PAC1 receptor and/or fusion proteins comprising both sequences compromising at least 80%, or at least 85% or 90%, or at least 95% or 98% sequence identity with any of the sequences described herein are also contemplated. The terms "identical" or percent "identity," refer to two or more sequences that are the same or have a specified percentage of amino acid residues that are the same, when compared and aligned for maximum correspondence, as measured using one of the following sequence comparison algorithms or by visual inspection. With respect to the peptides of this invention sequence identity is determined over the full length of the peptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman (1981) *Adv. Appl. Math.* 2: 482, by the homology alignment algorithm of Needleman & Wunsch (1970) *J. Mol. Biol.* 48: 443, by the search for similarity method of Pearson & Lipman (1988) *Proc. Natl. Acad. Sci., USA,* 85: 2444, by computerized implementations of these algorithms (GAP, BESTFIT, FASTA, and TFASTA in the Wisconsin Genetics Software Package, Genetics Computer Group, 575 Science Dr., Madison, WI), or by visual inspection.

A "maxadilan sequence" or a "maxadilan peptide" refers to a full length maxadilan precursor peptide or fragments thereof, or to a mature (61 aa) maxadilan peptide or fragments thereof and includes various mutants thereof (e.g., comprising 1, 2, 3, or 4 amino acid deletions, insertions, or substitutions).

A "PACAP sequence" or a "PACAP peptide" refers to a full length pituitary adenylate cyclase-activating peptide (PACAP) sequence or to fragments thereof capable of activating a PAC1 receptor. In certain embodiments the PACAP sequence comprises $PACAP_{1-38}$ or fragments thereof (e.g., $PACAP_{1-27}$) and includes various mutants thereof (e.g., comprising 1, 2, 3, or 4 amino acid deletions, insertions, or substitutions).

"Treating" or "treatment" of a condition as used herein may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The term "effective amount" or "therapeutically effective amount" or "prophylactically effective amount", or "diagnostically effective amount", refer to an amount of an active agent (e.g., PAC1 receptor agonist (e.g., MAXCAP) described herein that is effective to provide the desired/intended result and/or biological activity. Thus, for example, in various embodiments, an effective amount of a PAC1 receptor agonist described herein is an amount that is effective to downregulate appetite and/or to reduce obesity and/or to reduce body weight, and/or to inhibit adipogenesis and/or body fat accumulation, and/or reduce and/or regulate glucose homeostasis, and/or to improve or cure diabetes mellitus symptoms, and/or to reduce or cure inflammatory bowel diseases, and/or to reduce or cure chronic inflammatory diseases; and/or to ameliorate symptoms of and/or to treat systemic and organ-specific autoimmune diseases, and/or to reduce or cure dry eye syndrome, and/or to prevent or reduce organs, tissues and stem cells transplant rejection, and/or to improve embryo implant in uterus for in vitro fertilization, and/or to ameliorate one or more symptoms of connectivitis, and/or to slow the progression of osteoarthritis and/or rheumatoid arthritis, and/or psoriatic arthritis, and/or to prevent, or to reverse systemic hypertension, and/or to ameliorate one or more symptoms of atherosclerosis, and/or to slow the progression of, or to prevent, or to reverse non-alcoholic fatty liver disease (NAFLD), and/or NASH, and/or to ameliorate one or more symptoms of, and/or to slow, and/or to prevent, and/or to reverse hepatosteatosis (fatty liver), and/or to ameliorate one or more symptoms of, and/or to slow the progression of, and/or to prevent, and/or to reverse metabolic syndrome, and/or to ameliorate one or more symptoms of, and/or to slow the progression of, and/or to prevent, and/or to reverse insulin resistance, and/or to ameliorate one or more symptoms of, and/or to slow the progression of, and/or to prevent, and/or to reverse prediabetic syndrome, and/or to slow the progression of, and/or to prevent, and/or to reverse renal hypertension and/or chronic kidney diseases, and/or to slow the progression of, and/or to inhibit, and/or to reverse growth of tumors expressing PAC1 receptors, and/or to slow the progression of, and/or to prevent, and/or to reverse mast cell and/or basophil degranulation and release of allergic mediators, and/or to ameliorate the symptoms of, and/or to treat cystic fibrosis, and/or to ameliorate the symptoms of, and/or to treat celiac disease, and/or to slow the progression of, and/or to prevent, and/or to reverse schizophrenic and paranoid disorders, and/or to slow the progression of, and/or to prevent, and/or to reverse Alzheimer's disease, and/or to slow the progression of, and/or to ameliorate the symptoms, and/or to reverse neuromuscular dystrophy, and/or to slow the progression of, and/or to prevent, and/or to reverse neurological paralysis, and/or to slow the progression of, and/or to ameliorate the symptoms of, and/or to nerve injury paralysis, and/or to slow the progression of, and/or to ameliorate the symptoms of, and/or to reverse traumatic brain injury, and/or to ameliorate the symptoms of, and/or to reverse post traumatic stress disorder, and/or to ameliorate the symptoms of, and/or to reverse neuropathic disorders, and/or to ameliorate the symptoms of, and/or to reverse asthmatic syndrome, and/or ameliorating spermatogenesis and/or male infertility; and/or ameliorating female ovulation and/or female fertility; and/or to ameliorate the symptoms of, and/or to reverse chronic obstructive pulmonary disease, and/or to ameliorate the symptoms of, and/or to reverse lymphoproliferative disorders and/or myeloproliferative disorders, and/or to ameliorate the symptoms of, and/or to reverse thrombocytopenia, and/or to ameliorate the symptoms of, and/or to treat multiple myeloma, and/or to ameliorate the symptoms of, and/or to reverse acute or chronic nephropathies, and/or transient arterial stenosis and/or hemorrhagic shock, and/or antibiotic induced nephrotoxicity, and/or to ameliorate the symptoms of, and/or to treat polycystic kidney disease, and/or to ameliorate the symptoms of, and/or to reverse ocular hypertension, and/or glaucoma, and/or retinite pigmentosa, and/or to ameliorate the symptoms of, and/or to prevent ischemia/riperfusion of tissue and/or organs, and/or to ameliorate the symptoms of, and/or to prevent chronic pulmonary fibrotic processes, and/or to ameliorate the symptoms of, and/or to reverse, and/or coupled to radionuclides or fluorescent tracers to localize, and/or to diagnose, and/or to treat cancer and metastases.

A "diagnostically effective amount" refers to an amount effective to localize and/or diagnose a disease state when the agent(s) described herein are coupled to a detectable label (e.g., a radiopaque label, an MRI label, an NMR label, ar radionuclide, and a fluorescent tracer.

The term "consisting essentially of" when used with respect to a composition comprising a PAC1 receptor agonist described herein indicates that PAC1 receptor activating activity of the composition is provided predominantly or exclusively by the PAC1 receptor agonists and not by other agents present in the composition. In certain embodiments the PAC1 receptor agonist is the sole active agent in the composition.

The terms "isolated" "purified" or "biologically pure" refer to material which is substantially or essentially free from components that normally accompany it, as found in its native state. In the case of a peptide, an isolated (naturally occurring) peptide is typically substantially free of components with which it is associated in the cell, tissue, or organism. The term isolated also indicates that the peptide is not present in a phage display, yeast display, or other peptide library.

In various embodiments the amino acid abbreviations shown in Table 1 are used herein.

TABLE 1

Amino acid abbreviations.

| Name | 3 Letter | 1 Letter |
|---|---|---|
| Alanine | Ala | A |
| βAlanine (NH$_2$—CH$_2$—CH$_2$—COOH) | βAla | |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| episilon-aminocaproic acid (NH$^2$—(CH$_2$)$_5$—COOH) | Ahx | J |
| 4-aminobutanoic acid (NH$_2$—(CH$_2$)$_3$—COOH) | gAbu | |
| tetrahydroisoquinoline-3-carboxylic acid | | O |
| Lys(N(epsilon)-trifluoroacetyl) | | K[TFA] |
| α-aminoisobutyric acid | Aib | B |

The phrases "in conjunction with" or "in combination with" when used in reference to the use of the PAC1 receptor agonists (MAXCAPs) described herein in conjunction with one or more other drugs described herein (e.g., one or more dipeptidyl peptidase IV inhibitors, Exendin-4, GLP-1 agonists, CGRP, Adrenomedullin, Serotonin, Amylin, VIP and VPAC1 antagonists, VPAC2 agonists, and the like) indicates that the PAC1 receptor agonist(s) and the dipeptidyl peptidase IV inhibitors (or other drugs) are administered so that there is at least some chronological overlap in their physiological activity on the organism.

Thus, in various embodiments, the PAC1 receptor agonists and the dipeptidyl peptidase IV inhibitors can be administered simultaneously and/or sequentially. In sequential administration, there may even be some substantial delay (e.g., minutes or even hours or days) before administration of the second moiety as long as the first administered drug/agent has exerted some physiological alteration on the organism when the second administered agent is administered or becomes active in the organism.

DETAILED DESCRIPTION

Figure 1:
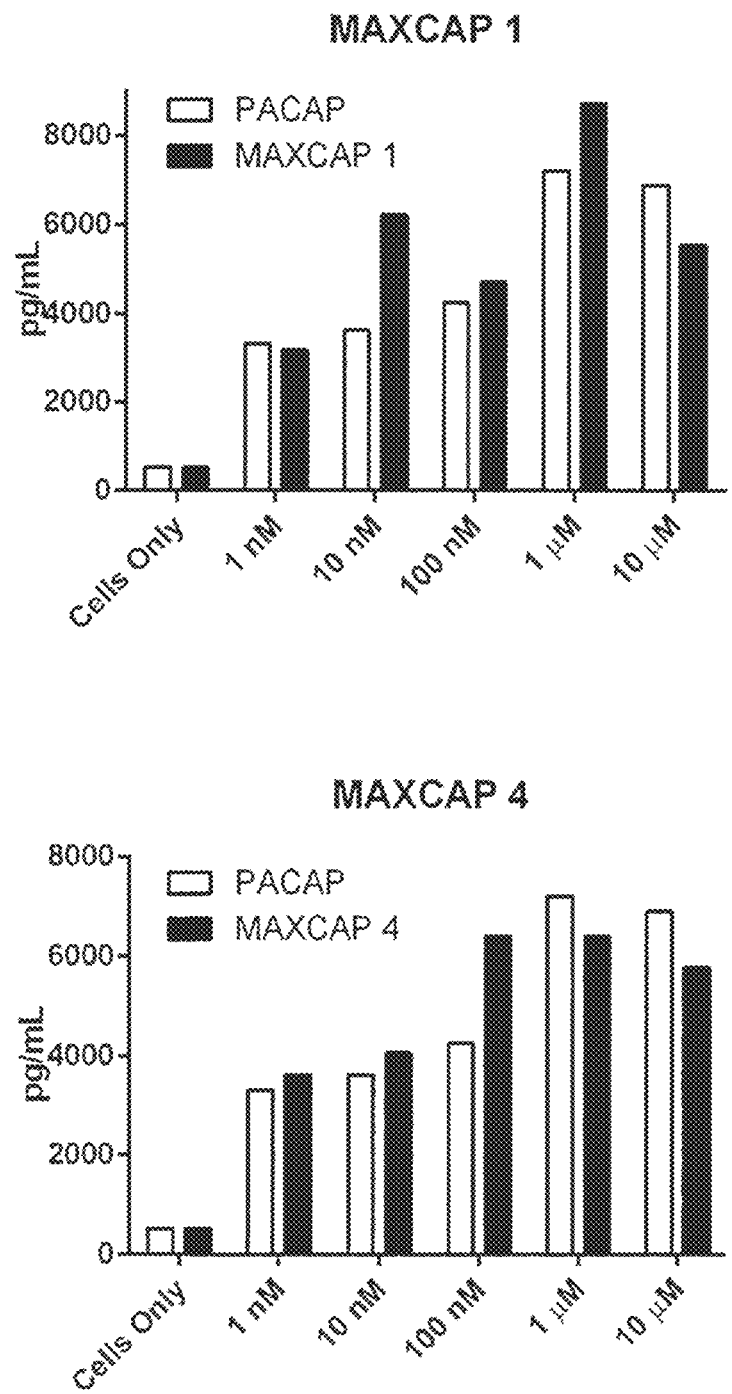
FIG. 1 illustrates stimulation of cAMP by MAXCAP 1 and by MAXCAP 4 as compared to PACAP$_{1-38}$.

PACAP and VIP are gastrointestinal neuropeptides, that bind with high affinity to their respective receptors PAC1 and VPACs in the gastrointestinal tract to regulate the digestive process physiology. Preliminary evidence has shown that PACAP has a role in central regulation of appetite. However, the peripheral role of PACAP and its receptors in the regulation of appetite and body metabolism have not been investigated, nor has its potential use in therapeutic compounds in clinical practice been fully explored.

In various embodiments novel PAC1 receptor agonists (a.k.a., MAXCAP(s)) are provided herein that are able to specifically bind to and activate PAC1 receptors. The role of the various MAXCAP(s) in the regulation of appetite, food intake, feeding behavior, body fat and lean mass composition, glycemia, and liver steatosis was examined. It was demonstrated that exogenous administration of the PAC1 receptor agonists (MAXCAP(s)) results in appetite suppression, lower glycemia, body weight and fat mass loss, improvement of obesity, liver steatosis, NASH and NAFLD, all of which are conditions that can occur commonly in patients with obesity disorders and in type 2 diabetes.

Accordingly, in various embodiments, the PAC1 receptor agonists (MAXCAPs) described herein (and/or pharmaceutical formulations thereof) are contemplated for use in one or more of the following:
  i) downregulating appetite and/or reducing obesity; and/or
  ii) inhibiting adipogenesis and/or fat accumulation; and/or
  iii) ameliorating one or more symptoms of, or slowing the progression of, or preventing, or reversing type 2 diabetes; and/or
  iv) ameliorating one or more symptoms of atherosclerosis; and/or hypertension
  v) slowing the progression of, or preventing, or reversing non-alcoholic fatty liver disease (NAFLD); and/or
  vi) ameliorating one or more symptoms of, and/or slowing, and/or preventing, and/or reversing hepatosteatosis (fatty liver); and/or
  vii) ameliorating one or more symptoms of, and/or slowing the progression of, and/or preventing, and/or reversing metabolic syndrome; and/or
  viii) ameliorating one or more symptoms of, and/or slowing the progression of, and/or preventing, and/or reversing insulin resistance; and/or
  ix) ameliorating one or more symptoms of, and/or slowing the progression of, and/or preventing, and/or reversing prediabetic syndrome; and/or
  x) ameliorating hepatosteatosis; and/or
  xi) ameliorating, and/or preventing, and/or reversing NASH and/or NAFLD.

In various embodiments the PAC1 receptor agonists (MAXCAPs) themselves are provided as are pharmaceutical formulations comprising the PAC1 receptor agonists.

PAC1 Receptor Agonists (MAXCAPs).

In various embodiments specific PAC1 receptor agonists, MAXCAP(s) are provided that can be absorbed systemically to activate PAC1 receptors. In certain illustrative, but non-limiting embodiments these PAC1 receptor agonists were synthesized by the identification of key amino acid residues of the native sequence of $PACAP_{1-27}$ and by including amino acid sequences of the maxadilan peptide. It is believed that maxadilan and PACAP have no structural homology.

In certain embodiments, the PAC1 receptor agonists utilize the maxadilan peptide or a fragment thereof as a "targeting sequence" to specifically bind to PAC1 receptor. The targeting sequence is attached to a pituitary adenylate cyclase-activating peptide (PACAP) or a fragment thereof (e.g., a portion of the PACAP N-terminus) which functions to activate PAC1 signaling. In certain embodiments the PACAP fragment consists or comprise a PACAP1-38 peptide, or a PACAP1-27 peptide or fragments thereof, optimally incorporated one or more mutations or substitutions. By way of reference, the full-length (61 aa) maxadilan peptide and $PACAP_{1-27}$, and $PACAP_{1-38}$ peptides area shown in Table 2.

TABLE 2

Amino acid sequences of maxadilan peptide, $PACAP_{1-38}$, and $PACAP_{1-27}$. Arrows in maxadilan sequence indicates sites that tolerate mutation or where mutation enhances activity. Arrows in PACAP sequences indicates location between residues 11 and 12 of PACAP.

| Peptide | Amino acid Sequence | SEQ ID NO |
|---|---|---|
| Maxadilan | ↓↓<br>CDATCQFRKA IDDCQKQAHH SNVLQTSVQT ↓ TATFTSMDTS<br>↓↓ ↓↓ ↓ ↓<br>QLPGNSVFKE CMKQKKKEFK A | 1 |
| $PACAP_{1-38}$ | ↓<br>HSDGIFTDSY S RYRKQMAVK KYLAAVLGKR YKQRVKNK | 2 |
| $PACAP_{1-27}$ | ↓<br>HSDGIFTDSY S RYRKQMAVK KYLAAVL | 3 |

In certain embodiments the PACAP sequence can be chemically conjugated to the maxadilan sequence, while in other embodiments the two sequences can be directly joined, joined by an amino acid, or joined by a peptide linker to provide a single continuous fusion protein.

The constructs described herein are more resistant to DPP-IV protease degradation than the native $PACAP_{1-27}$ and $PACAP_{1-38}$ and thus have a longer half-life.

In certain embodiments the targeting sequence (e.g., maxadilan peptide or fragments thereof and/or mutants thereof) is chemically conjugated to the peptide that activates PAC1 signalling (e.g., PACAP or fragments thereof such as $PACAP_{1-38}$, $PACAP_{1-27}$, and variants thereof). In certain embodiments the targeting sequence is joined directly toe the peptide that activates PAC1 signaling, or is joined through an amino acid, or is joined through a peptide linker. In these cases, the peptide can be chemically synthesized, or recombinaly expressed as a fusion peptide.

Illustrative PAC1 receptor agonists that have been prepared as fusion proteins and subjected to extensive testing area shown in Table 3.

TABLE 3

Illustrative, but non-limiting examples of PAC1 receptor agonists (MAXCAPs) contemplated herein. Bold indicates amino acid sequence derived from $PACAP_{1-27}$. Single underline indicates amino acid sequence derived from maxadilan (e.g., PGNSVFKECMKQKKKEFKAGK, SEQ ID NO: 4). Double underline indicates amino acid linker or peptide linker.

| Name | Amino Acid Sequence |
|---|---|
| MAXCAP 1 | HSDGIFTDSYSSRYRKQMAVKKYLAAVL PGNSVFKECMKQKKKEFKAGK<br>(SEQ ID NO: 5) |
| MAXCAP 4 | HSDGIF <u>A</u> PGNSVFKECMKQKKKEFKAGK<br>(SEQ ID NO: 6) |

TABLE 3-continued

Illustrative, but non-limiting examples of PAC1 receptor agonists (MAXCAPs) contemplated herein. Bold indicates amino acid sequence derived from PACAP$_{1-27}$. Single underline indicates amino acid sequence derived from maxadilan (e.g., PGNSVFKECMKQKKKEFKAGK, SEQ ID NO: 4). Double underline indicates amino acid linker or peptide linker.

| Name | Amino Acid Sequence |
|---|---|
| MAXCAP A | HSDGIFT <u>SMDTSQL</u> <u>PGNSVFKECMKQKKKEFKAGK</u> (SEQ ID NO: 7) |
| MAXCAP B | HSDGIFT <u>PGNSVFKECMKQKKKEFKAGK</u> (SEQ ID NO: 8) |
| | HSDGIFTDSYS <u><u>A</u></u> <u>PGNSVFKECMKQKKKEFKAGK</u> (SEQ ID NO: 9) |
| | HSDGIFTDSYS <u><u>K</u></u> <u>PGNSVFKECMKQKKKEFKAGK</u> (SEQ ID NO: 10) |
| | HSDGIFTDSYSRYR <u><u>A</u></u> <u>PGNSVFKECMKQKKKEFKAGK</u> (SEQ ID NO: 11) |
| | HSDGIFTDSYSRYRK <u>PGNSVFKECMKQKKKEFKAGK</u> (SEQ ID NO: 12) |

The PAC1 receptor agonists (MAXCAPs) shown in Table 3, especially MAXCAP1 and MAXCAP 4, are illustrative and non-limiting. In view of these illustrative fusion proteins, numerous PAC1 receptor agonists will be available to one of skill in the art (e.g., as described below).

For example, as noted above, the PAC1 receptor agonists need not be provided as fusion proteins. Instead, the targeting sequence (e.g., maxadilan or fragment thereof) and the PACAP sequence can be chemically conjugated using, for example a homo- or hetero-bifunctional linker.

In certain embodiments the targeting sequence (e.g., maxadilan or fragment thereof) can be attached to the amino terminus of the PACAP sequence, while in other embodiments the targeting sequence can be attached to the carboxyl terminus of the PACAP sequence. In certain embodiments a plurality of targeting sequences (e.g., 2, 3, 4, 5, or more) can be attached to a single PACAP sequence. In certain embodiments a plurality of PACAP sequences (e.g., 2, 3, 4, 5, or more) can be attached to a single targeting sequence (e.g., maxadilan or a fragment thereof). In certain embodiments a plurality of targeting sequences (e.g., 2, 3, 4, 5, or more) can be attached to a plurality of PACAP sequences (e.g., 2, 3, 4, 5, or more). In certain embodiments the maxadilan and/or PACAP sequences are components of a dendrimeric construct.

In certain embodiments the PAC1 receptor agonist (MAXCAP) comprises a targeting sequence that binds to the PAC1 receptor attached to a peptide that activates PAC1 signaling, where the targeting sequence comprises a maxadilan peptide or fragment thereof effective to bind a PAC1 receptor, and the peptide that activates PAC1 signaling comprises (PACAP) or a fragment thereof or PACAP$_{1-38}$ or a fragment thereof effective to activate PAC1 signaling, wherein said PACAP or fragment thereof or PACAP$_{1-38}$ or fragment thereof optionally comprises an amino acid insertion between residues 11 and 12 of said PACP$_{1-38}$.

Targeting Sequence(s).

In various embodiments the PAC1 receptor agonists contemplated herein comprise a targeting peptide comprising (or consisting of) an amino acid sequence that binds (e.g., specifically binds) to the PAC1 receptor. In various embodiments the targeting sequence comprises (or consists of) a maxadilan peptide or fragment and/or analogue or homologue thereof that binds to the PAC1 receptor. In certain embodiments, the maxadilan sequence comprises or consists of a full-length maxadilan sequence (precursor sequence) or fragment thereof. In certain embodiments the maxadilan sequence comprises or consists of a mature maxadilan (61 aa peptide) sequence or fragments there of effective to bind to a PAC1 receptor. In certain embodiments, the maxadilan sequence is a maxadilan fragment. Illustrative maxadilan sequences are shown in Table 4.

TABLE 4

Illustrative, but non-limiting examples of maxadilan sequences. Arrows indicate sites known to be tolerant of mutation (see, e.g., Reddy et al. (2006) J. Biol. Chem., 281(24): 16197-16201).

| Amino Acid Sequence | SEQ. ID. NO. |
|---|---|
| ↓    ↓↓  ↓↓  ↓ ↓<br>TATFTSMDTS QLPGNSVFKE CMKQKKKEFK A | 13 |
| ATFTSMDTS QLPGNSVFKE CMKQKKKEFK A | 14 |
| TFTSMDTS QLPGNSVFKE CMKQKKKEFK A | 15 |
| FTSMDTS QLPGNSVFKE CMKQKKKEFK A | 16 |
| TSMDTS QLPGNSVFKE CMKQKKKEFK A | 17 |

TABLE 4-continued

Illustrative, but non-limiting examples of maxadilan sequences. Arrows indicate sites known to be tolerant of mutation ( TABLE 4-continued Illustrative, but non-limiting examples of maxadilan sequences. Arrows indicate sites known to be tolerant of mutation (see, e.g., Reddy et al. (2006) *J. Biol. Chem.*, 281(24): 16197-16201).

| Amino Acid Sequence | SEQ. ID. NO. |
|---|---|
| NVAEGCDATCQFRKAIDDCQKQAHHSNVLQTSVQTTATFTSMDTSQLPGNSVFKECMKQKKKEFSSGK | 44 |
| VAEGCDATCQFRKAIDDCQKQAHHSNVLQTSVQTTATFTSMDTSQLPGNSVFKECMKQKKKEFSSGK | 45 |
| AEGCDATCQFRKAIDDCQKQAHHSNVLQTSVQTTATFTSMDTSQLPGNSVFKECMKQKKKEFSSGK | 46 |
| EGCDATCQFRKAIDDCQKQAHHSNVLQTSVQTTATFTSMDTSQLPGNSVFKECMKQKKKEFSSGK | 47 |
| GCDATCQFRKAIDDCQKQAHHSNVLQTSVQTTATFTSMDTSQLPGNSVFKECMKQKKKEFSSGK | 48 |
| CDATCQFRKAIDDCQKQAHHSNVLQTSVQTTATFTSMDTSQLPGNSVFKECMKQKKKEFSSGK | 49 |
| DATCQFRKAIDDCQKQAHHSNVLQTSVQTTATFTSMDTSQLPGNSVFKECMKQKKKEFSSGK | 50 |
| ATCQFRKAIDDCQKQAHHSNVLQTSVQTTATFTSMDTSQLPGNSVFKECMKQKKKEFSSGK | 51 |
| TCQFRKAIDDCQKQAHHSNVLQTSVQTTATFTSMDTSQLPGNSVFKECMKQKKKEFSSGK | 52 |
| CQFRKAIDDCQKQAHHSNVLQTSVQTTATFTSMDTSQLPGNSVFKECMKQKKKEFSSGK | 53 |
| QFRKAIDDCQKQAHHSNVLQTSVQTTATFTSMDTSQLPGNSVFKECMKQKKKEFSSGK | 54 |
| FRKAIDDCQKQAHHSNVLQTSVQTTATFTSMDTSQLPGNSVFKECMKQKKKEFSSGK | 55 |
| RKAIDDCQKQAHHSNVLQTSVQTTATFTSMDTSQLPGNSVFKECMKQKKKEFSSGK | 56 |
| KAIDDCQKQAHHSNVLQTSVQTTATFTSMDTSQLPGNSVFKECMKQKKKEFSSGK | 57 |
| AIDDCQKQAHHSNVLQTSVQTTATFTSMDTSQLPGNSVFKECMKQKKKEFSSGK | 58 |
| IDDCQKQAHHSNVLQTSVQTTATFTSMDTSQLPGNSVFKECMKQKKKEFSSGK | 59 |
| DDCQKQAHHSNVLQTSVQTTATFTSMDTSQLPGNSVFKECMKQKKKEFSSGK | 60 |
| DCQKQAHHSNVLQTSVQTTATFTSMDTSQLPGNSVFKECMKQKKKEFSSGK | 61 |
| CQKQAHHSNVLQTSVQTTATFTSMDTSQLPGNSVFKECMKQKKKEFSSGK | 62 |
| QKQAHHSNVLQTSVQTTATFTSMDTSQLPGNSVFKECMKQKKKEFSSGK | 63 |
| KQAHHSNVLQTSVQTTATFTSMDTSQLPGNSVFKECMKQKKKEFSSGK | 64 |
| QAHHSNVLQTSVQTTATFTSMDTSQLPGNSVFKECMKQKKKEFSSGK | 65 |
| AHHSNVLQTSVQTTATFTSMDTSQLPGNSVFKECMKQKKKEFSSGK | 66 |
| HHSNVLQTSVQTTATFTSMDTSQLPGNSVFKECMKQKKKEFSSGK | 67 |
| HSNVLQTSVQTTATFTSMDTSQLPGNSVFKECMKQKKKEFSSGK | 68 |
| SNVLQTSVQTTATFTSMDTSQLPGNSVFKECMKQKKKEFSSGK | 69 |
| NVLQTSVQTTATFTSMDTSQLPGNSVFKECMKQKKKEFSSGK | 70 |
| VLQTSVQTTATFTSMDTSQLPGNSVFKECMKQKKKEFSSGK | 71 |

TABLE 4-continued

Illustrative, but non-limiting examples of maxadilan sequences. Arrows indicate sites known to be tolerant of mutation (see, e.g., Reddy et al. (2006) *J. Biol. Chem.*, 281(24): 16197-16201).

| Amino Acid Sequence | SEQ. ID. NO. |
|---|---|
| LQTSVQTTATFTSMDTSQLPGNSVFKECMKQKKKEFSSGK | 72 |
| QTSVQTTATFTSMDTSQLPGNSVFKECMKQKKKEFSSGK | 73 |
| TSVQTTATFTSMDTSQLPGNSVFKECMKQKKKEFSSGK | 74 |
| SVQTTATFTSMDTSQLPGNSVFKECMKQKKKEFSSGK | 75 |
| VQTTATFTSMDTSQLPGNSVFKECMKQKKKEFSSGK | 76 |
| QTTATFTSMDTSQLPGNSVFKECMKQKKKEFSSGK | 77 |
| TTATFTSMDTSQLPGNSVFKECMKQKKKEFSSGK | 78 |
| GNSVFKECMKQKKKEFSSGK | 79 |
| NSVFKECMKQKKKEFSSGK | 80 |
| SVFKECMKQKKKEFSSGK | 81 |
| VFKECMKQKKKEFSSGK | 82 |
| FKECMKQKKKEFSSGK | 83 |
| KECMKQKKKEFSSGK | 84 |
| ECMKQKKKEFSSGK | 85 |
| CMKQKKKEFSSGK | 86 |
| MKQKKKEFSSGK | 87 |
| KQKKKEFSSGK | 88 |
| QKKKEFSSGK | 89 |
| KKKEFSSGK | 90 |
| KKEFSSGK | 91 |
| KEFSSGK | 92 |
| EFSSGK | 93 |
| FSSGK | 94 |

In certain embodiments the maxadilan fragment comprises a fragment shown in Table 4, having a mutation corresponding to N45 and/or K49, and/or P43, and/or D38, and/or E50, and/or K53, and/or K55 of the full-length maxadilan peptide (see, e.g., arrows in Table 4). In certain embodiments, the mutation is a mutation to alanine, or to serine, or to cysteine, or to threonine. In certain embodiments, the mutation(s) comprise an N45A mutation. In certain embodiments the mutation(s) comprise a K49A mutation. In certain embodiments, the mutation(s) comprise a P43A mutation. In certain embodiments the mutation(s) comprise an E50A mutation. In certain embodiments, the mutation(s) comprise a K53A mutation.

In certain embodiments the maxadilan sequence comprises or consists of a peptide that binds (e.g. specifically binds) to the PAC1 receptor and that shows at least 85%, or at least 90%, or at least 95%, or at least 98%, or at least 99% sequence identity with any one or more of the foregoing maxadilan sequences. In certain embodiments the maxadilan sequence comprises or consists of a peptide that binds to the PAC1 receptor and that does not substantially bind to the VPAC1 receptor and/or to the VPAC2 receptor and that shows at least 85%, or at least 90%, or at least 95%, or at least 98%, or at least 99% sequence identity with any one or more of the foregoing maxadilan sequences.

In certain embodiments the maxadilan sequences comprises all "L" amino acids. In certain embodiments, the maxadilan sequences comprise one or more "D" amino acids selected so that the maxadilan sequence retains the ability to activate the PAC1 receptor.

In certain embodiments the maxadilan sequences comprise beta peptides and/or peptidomimetics.

In certain embodiments moieties that bind to the PAC1 receptor that are not maxadilan peptides are contemplated. For example, U.S. Patent Publ. No: 2016/0039939 describes anti-PAC1 antibodies and antibody fragments that bind to the PAC1 receptor signaling.

It will be recognized that the above-described targeting sequences are illustrative and using the teaching provided herein numerous other PAC1 binding sequences will be available to one of skill in the art.

PAC1 Activating Peptides (PACAP and Fragments Thereof).

In various embodiments the targeting sequence(s) comprising the PAC1 receptor agonist(s) contemplated herein comprise a PAC1 activator (e.g. an amino acid sequence that activates the PAC1 receptor (e.g., PACAP or fragments thereof)). Illustrative, but non-limiting PAC1 activating sequences comprise pituitary adenylate cyclase-activating peptide (PACAP) or a fragment thereof (e.g., $PACAP_{1-38}$ or a fragment thereof and/or $PACAP_{1-27}$ or a fragment thereof). In certain embodiments, the PAC1 activator sequence comprise one or more (e.g., 1, 2, 3, 4, 5, 6, or more) amino acid insertions and/or one or more (e.g., 1, 2, 3, 4, 5, 6, or more) conservative amino acid substitutions of PACAP or a PACAP fragment. Illustrative, but non-limiting examples of PAC1 activating sequences are shown in Table 5.

TABLE 5

Illustrative examples of PAC1 activating sequences comprising fragements of PACAP. It will be recognized that where serine is shown as an insertion, the residue can be replaced with threonine or other conservative substitution. In certain embodiments R at position 12 can be substituted with A or K or the PAC1 activating sequence can consist of the sequence HSDGIFTDSYS (SEQ ID NO: 125) and R or K are used as a linker. In certain embodiments, K at position 15 can be substituted with A, or the the PAC1 activating sequence can consist of the sequence HSDGIFTDSYSRYR (SEQ ID NO: 120) and A can be used as a linker.

| Amino Acid Sequence | SEQ ID NO |
|---|---|
| HSDGIFTDSYSRYRKQMAVKKYLAAVLGKRYKQRVKNK | 95 |
| HSDGIFTDSYSRYRKQMAVKKYLAAVLGKRYKQRVKN | 96 |
| HSDGIFTDSYSRYRKQMAVKKYLAAVLGKRYKQRVK | 97 |
| HSDGIFTDSYSRYRKQMAVKKYLAAVLGKRYKQRV | 98 |
| HSDGIFTDSYSRYRKQMAVKKYLAAVLGKRYKQR | 99 |
| HSDGIFTDSYSRYRKQMAVKKYLAAVLGKRYKQ | 100 |
| HSDGIFTDSYSRYRKQMAVKKYLAAVLGKRYK | 101 |
| HSDGIFTDSYSRYRKQMAVKKYLAAVLGKRY | 102 |
| HSDGIFTDSYSRYRKQMAVKKYLAAVLGKR | 103 |
| HSDGIFTDSYSRYRKQMAVKKYLAAVLGK | 104 |
| HSDGIFTDSYSRYRKQMAVKKYLAAVLG | 105 |
| HSDGIFTDSYSRYRKQMAVKKYLAAVL | 106 |
| HSDGIFTDSYSRYRKQMAVKKYLAAV | 107 |
| HSDGIFTDSYSRYRKQMAVKKYLAA | 108 |
| HSDGIFTDSYSRYRKQMAVKKYLA | 109 |
| HSDGIFTDSYSRYRKQMAVKKYL | 110 |
| HSDGIFTDSYSRYRKQMAVKKY | 111 |
| HSDGIFTDSYSRYRKQMAVKK | 112 |
| HSDGIFTDSYSRYRKQMAVK | 113 |
| HSDGIFTDSYSRYRKQMAV | 114 |

TABLE 5-continued

Illustrative examples of PAC1 activating sequences comprising fragements of PACAP. It will be recognized that where serine is shown as an insertion, the residue can be replaced with threonine or other conservative substitution. In certain embodiments R at position 12 can be substituted with A or K or the PAC1 activating sequence can consist of the sequence HSDGIFTDSYS (SEQ ID NO: 125) and R or K are used as a linker. In certain embodiments, K at position 15 can be substituted with A, or the the PAC1 activating sequence can consist of the sequence HSDGIFTDSYSRYR (SEQ ID NO: 120) and A can be used as a linker.

| Amino Acid Sequence | SEQ ID NO |
|---|---|
| HSDGIFTDSYSRYRKQMA | 115 |
| HSDGIFTDSYSRYRKQM | 116 |
| HSDGIFTDSYSRYRKQ | 117 |
| HSDGIFTDSYSRYRK | 118 |
| HSDGIFTDSYSRYRA | 119 |
| HSDGIFTDSYSRYR | 120 |
| HSDGIFTDSYSRY | 121 |
| HSDGIFTDSYSR | 122 |
| HSDGIFTDSYSA | 123 |
| HSDGIFTDSYSK | 124 |
| HSDGIFTDSYS | 125 |
| HSDGIFTDSY | 126 |
| HSDGIFTDS | 127 |
| HSDGIFTD | 128 |
| HSDGIFT | 129 |
| HSDGIF | 130 |
| Sequences with amino acid insertion: | |
| HSDGIFTDSYSSRYRKQMAVKKYLAAVLGKRYKQRVKNK | 131 |
| HSDGIFTDSYSSRYRKQMAVKKYLAAVLGKRYKQRVKNK | 132 |
| HSDGIFTDSYSSRYRKQMAVKKYLAAVLGKRYKQRVKN | 133 |
| HSDGIFTDSYSSRYRKQMAVKKYLAAVLGKRYKQRVK | 134 |
| HSDGIFTDSYSSRYRKQMAVKKYLAAVLGKRYKQRV | 135 |
| HSDGIFTDSYSSRYRKQMAVKKYLAAVLGKRYKQR | 136 |
| HSDGIFTDSYSSRYRKQMAVKKYLAAVLGKRYKQ | 137 |
| HSDGIFTDSYSSRYRKQMAVKKYLAAVLGKRYK | 138 |
| HSDGIFTDSYSSRYRKQMAVKKYLAAVLGKRY | 139 |
| HSDGIFTDSYSSRYRKQMAVKKYLAAVLGKR | 140 |
| HSDGIFTDSYSSRYRKQMAVKKYLAAVLGK | 141 |
| HSDGIFTDSYSSRYRKQMAVKKYLAAVLG | 142 |
| HSDGIFTDSYSSRYRKQMAVKKYLAAVL | 143 |
| HSDGIFTDSYSSRYRKQMAVKKYLAAV | 144 |
| HSDGIFTDSYSSRYRKQMAVKKYLAA | 145 |

TABLE 5-continued

Illustrative examples of PAC1 activating sequences comprising fragments of PACAP. It will be recognized that where serine is shown as an insertion, the residue can be replaced with threonine or other conservative substitution. In certain embodiments R at position 12 can be substituted with A or K or the PAC1 activating sequence can consist of the sequence HSDGIFTDSYS (SEQ ID NO: 125) and R or K are used as a linker. In certain embodiments, K at position 15 can be substituted with A, or the the PAC1 activating sequence can consist of the sequence HSDGIFTDSYSRYR (SEQ ID NO: 120) and A can be used as a linker.

| Amino Acid Sequence | SEQ ID NO |
|---|---|
| HSDGIFTDSYSSRYRKQMAVKKYLA | 146 |
| HSDGIFTDSYSSRYRKQMAVKKYL | 147 |
| HSDGIFTDSYSSRYRKQMAVKKY | 148 |
| HSDGIFTDSYSSRYRKQMAVKK | 149 |
| HSDGIFTDSYSSRYRKQMAVK | 150 |
| HSDGIFTDSYSSRYRKQMAV | 151 |
| HSDGIFTDSYSSRYRKQMA | 152 |
| HSDGIFTDSYSSRYRKQM | 153 |
| HSDGIFTDSYSSRYRKQ | 154 |
| HSDGIFTDSYSSRYRK | 155 |
| HSDGIFTDSYSSRYR | 156 |
| HSDGIFTDSYSSRY | 157 |
| HSDGIFTDSYSSR | 158 |
| HSDGIFTDSYSS | 159 |

In certain embodiments the PAC1 activating sequence comprises or consists of the amino acid sequence HSDGIF (SEQ ID NO:130). In certain embodiments the PAC1 activating sequence comprises or consists of the amino acid sequence HSDGIFT (SEQ ID NO:129). In certain embodiments, the PAC1 activating sequence comprises or consists of the amino acid sequence HSDGIFTDSYS-RYRKQMAVKKYLAAVL (SEQ ID NO:106). In certain embodiments, the PAC1 activating sequence comprises or consists of the amino acid sequence HSDGIFTDSYS-SRYRKQMAVKKYLAAVL (SEQ ID NO: 143).

In certain embodiments the PAC1 activating sequence comprises or consists of a peptide that activates the PAC1 receptor and that shows at least 85%, or at least 90%, or at least 95%, or at least 98%, or at least 99% sequence identity with any one or more of the foregoing PAC1 receptor activating sequences.

In certain embodiments the PAC1 activating sequences comprises all "L" amino acids. In certain embodiments, the targeting sequences comprise one or more "D" amino acids selected so that the targeting sequence retains the ability to bind to the PAC1 receptor.

In certain embodiments the PAC1 activating sequences comprise beta peptides and/or peptidomimetics.

It will be recognized that the above-described PAC1 activating sequences are illustrative and using the teaching provided herein numerous other PAC1 activating sequence will be available to one of skill in the art.

Preparing PAC1 Receptor Agonists (MAXCAPs).

The targeting sequences (e.g., maxadilan peptides or fragments thereof), and/or the sequences that activate PAC1 receptor (e.g., PACAP sequences or fragments there of), and/or fusion proteins described herein can be chemically synthesized using standard chemical peptide synthesis techniques or, particularly where the peptide does not comprise "D" amino acid residues, the peptide can be recombinantly expressed. Where the "D" polypeptides are recombinantly expressed, a host organism (e.g. bacteria, plant, fungal cells, etc.) can be cultured in an environment where one or more of the amino acids is provided to the organism exclusively in a D form. Recombinantly expressed peptides in such a system then incorporate those D amino acids.

In certain embodiments, D amino acids can be incorporated in recombinantly expressed peptides using modified amino acyl-tRNA synthetases that recognize D-amino acids.

In certain embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) *Solid-Phase Peptide Synthesis*; pp. 3-284 in *The Peptides: Analysis, Synthesis, Biology. Vol. 2: Special Methods in Peptide Synthesis, Part A*; Merrifield et al. (1963) *J. Am. Chem. Soc.*, 85: 2149-2156, and Stewart et al. (1984) *Solid Phase Peptide Synthesis*, 2nd ed. Pierce Chem. Co., Rockford, Ill.

In one embodiment, the peptides can be synthesized by the solid phase peptide synthesis procedure using a benzhyderylamine resin (Beckman Bioproducts, 0.59 mmol of NH$_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor can be used for this purpose.

It is noted that in the chemical synthesis of peptides, particularly peptides comprising D amino acids, the synthesis usually produces a number of truncated peptides in addition to the desired full-length product. Thus, the peptides are typically purified using, e.g., HPLC.

D-amino acids, beta amino acids, non-natural amino acids, and the like can be incorporated at one or more positions in the peptide simply by using the appropriately derivatized amino acid residue in the chemical synthesis. Modified residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form and/or otherwise modified amino acids can be completely omitted or incorporated at any position in the peptide as desired. Thus, for example, in certain embodiments, the peptide can comprise a single modified acid, while in other embodiments, the peptide comprises at least two, generally at least three, more generally at least four, most generally at least five, preferably at least six, more preferably at least seven or even all modified amino acids. In certain embodiments, essentially every amino acid is a D-form amino acid.

As indicated above, the peptides comprising the PAC1 receptor agonists and/or the PAC1 receptor agonist fusion proteins described herein can also be recombinantly expressed. Accordingly, in certain embodiments, targeting sequences and/or the maxadilan sequences and/or the fusion peptides described herein are synthesized using recombinant expression systems. Generally, this involves creating a DNA sequence that encodes the desired peptide or fusion protein, placing the DNA in an expression cassette under the control of a particular promoter, expressing the peptide or fusion protein in a host, isolating the expressed peptide or fusion protein and, if required, renaturing the peptide or fusion protein.

DNA encoding the peptide(s) or fusion protein(s) described herein can be prepared by any suitable method as described above, including, for example, cloning and restriction of appropriate sequences or direct chemical synthesis.

This nucleic acid can be easily ligated into an appropriate vector containing appropriate expression control sequences (e.g. promoter, enhancer, etc.), and, optionally, containing one or more selectable markers (e.g. antibiotic resistance genes).

The nucleic acid sequences encoding the peptides or fusion proteins described herein can be expressed in a variety of host cells, including, but not limited to, *E. coli*, other bacterial hosts, yeast, fungus, and various higher eukaryotic cells such as insect cells (e.g. SF3), the COS, CHO and HeLa cells lines and myeloma cell lines. The recombinant protein gene will typically be operably linked to appropriate expression control sequences for each host. For *E. coli* this can include a promoter such as the T7, trp, or lambda promoters, a ribosome binding site and preferably a transcription termination signal. For eukaryotic cells, the control sequences can include a promoter and often an enhancer (e.g., an enhancer derived from immunoglobulin genes, SV40, cytomegalovirus, etc.), and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant peptide(s) or fusion protein(s) can be purified according to standard procedures of the art, including ammonium sulfate precipitation, affinity columns, column chromatography, gel electrophoresis and the like (see, generally, R. Scopes, (1982) *Protein Purification*, Springer-Verlag, N.Y.; Deutscher (1990) *Methods in Enzymology Vol. 182: Guide to Protein Purification*, Academic Press, Inc. N.Y.). Substantially pure compositions of at least about 90 to 95% homogeneity are preferred, and 98 to 99% or more homogeneity are most preferred.

One of skill in the art would recognize that after chemical synthesis, biological expression, or purification, the peptide(s) or fusion protein(s) may possess a conformation substantially different than desired native conformation. In this case, it may be necessary to denature and reduce the peptide or fusion protein and then to cause the molecule to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski et al., for example, describes the denaturation and reduction of inclusion body proteins in guanidine-DTE. The protein is then refolded in a redox buffer containing oxidized glutathione and L-arginine.

One of skill would recognize that modifications can be made to the peptide(s) and/or fusion protein(s) without diminishing their biological activity. Some modifications may be made to facilitate the cloning, expression, or incorporation of the targeting sequence and/or the maxadilan sequence into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Joining PAC1 Receptor Targeting Sequences to PAC1 Receptor Activating Sequences.

Chemical Conjugation.

In certain embodiments the targeting sequence that binds a PAC1 receptor (e.g., a maxadilan sequence) is chemically conjugated to the sequence effective to activate PAC1 (e.g., a PACAP sequence). In certain embodiments, such chemical conjugates are prepared by conjugation of the targeting sequence directly to the maxadilan peptide via naturally occurring reactive groups or the targeting sequence and/or the maxadilan peptide(s) can be functionalized to provide such reactive groups.

In certain embodiments the targeting sequence that binds a PAC1 receptor is chemically conjugated to the sequence effective to activate PAC1 via one or more linking agents. Thus, in various embodiments the targeting sequence that binds a PAC1 receptor and the PAC1 activator sequence can be conjugated via a single linking agent or multiple linking agents. For example, the targeting sequence and the PAC1 activator sequence can be conjugated via a single multifunctional (e.g., bi-, tri-, or tetra-) linking agent or a pair of complementary linking agents. In another embodiment, the targeting sequence and the PAC1 activator sequence are conjugated via two, three, or more linking agents. Suitable linking agents include, but are not limited to, e.g., functional groups, affinity agents, stabilizing groups, and combinations thereof.

In certain embodiments the linking agent is or comprises a functional group. Functional groups include monofunctional linkers comprising a reactive group as well as multifunctional crosslinkers comprising two or more reactive groups capable of forming a bond with two or more different functional targets. In some embodiments, the multifunctional crosslinkers are heterobifunctional crosslinkers comprising two or more different reactive groups.

Suitable reactive groups include, but are not limited to thiol (—SH), carboxylate (COOH), carboxyl (—COOH), carbonyl, amine ($NH_2$), hydroxyl (—OH), aldehyde (—CHO), alcohol (ROH), ketone ($R_2CO$), active hydrogen, ester, sulfhydryl (SH), phosphate (—$PO_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions useful in forming chimeric moieties include those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) *Advanced Organic Chemistry*, 3rd Ed., John Wiley & Sons, New York, Hermanson (1996) *Bioconjugate Techniques*, Academic Press, San Diego; and Feeney et al. (1982) *Modification of Proteins; Advances in Chemistry Series*, Vol. 198, American Chemical Society, Washington, D.C.

A "linker" or "linking agent" as used herein, is a molecule that is used to join two or more molecules. In certain embodiments, the linker is typically capable of forming covalent bonds to both molecule(s) (e.g., the targeting sequence and the maxadilan sequence). Suitable linkers are well known to those of skill in the art and include, but are not limited to, straight or branched-chain carbon linkers, heterocyclic carbon linkers, or peptide linkers. In certain embodiments, the linkers can be joined to the constituent amino acids through their side groups (e.g., through a disulfide linkage to cysteine). However, in certain embodiments, the linkers will be joined to the alpha carbon amino and carboxyl groups of the terminal amino acids.

A bifunctional linker having one functional group reactive with a group on one molecule (e.g., targeting peptide), and another group reactive on the other molecule (e.g., a maxadilan peptide), can be used to form the desired conjugate. Alternatively, derivatization can be performed to provide functional groups. Thus, for example, procedures for the generation of free sulfhydryl groups on peptides are also known (See U.S. Pat. No. 4,659,839).

In certain embodiments the linking agent is a heterobifunctional crosslinker comprising two or more different reactive groups that form a heterocyclic ring that can interact with a peptide. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. In one embodiment, the heterobifunctional crosslinker is SMCC.

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680, 338; 4,569,789; and 4,589,071; and Borlinghaus et al. (1987) *Cancer Res.* 47: 4071-4075). Illustrative linking protocols are provided herein in Examples 2 and 3.

Fusion Proteins.

In certain embodiments the PAC1 receptor (PAC1r) targeting sequence (e.g., a maxadilan peptide) and the sequence that activates PAC1 (e.g. as PACAP peptide) are joined together directly or through an amino acid, or through a linker to form a single chain fusion protein/peptide. In certain embodiments, such a fusion protein/peptide can readily be chemically synthesized or recombinantly expressed as a fusion protein (i.e., a chimeric fusion protein).

In certain embodiments the chimeric fusion proteins are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein, e.g., as described above.

While the targeting sequence and effector(s) (PAC1 activator(s)) can be directly joined together, one of skill will appreciate that they can be separated by a peptide spacer/linker consisting of one or more amino acids. Generally, the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

In certain embodiments the targeting sequence and the PAC1 activator are joined by a single amino acid such as A, C, P, or G. In certain embodiments, the targeting sequence and the maxadilan sequence are joined by a single alanine.

In certain embodiments a peptide linker is used to join the targeting sequence and the PAC1 activator sequence. In various embodiments, the peptide linker is relatively short, e.g., less than about 15 amino acids, or less than about 13 amino acids, or less than about 10 amino acids, or less than about 8 amino acids, or less than bout 5 amino acids or about 3 amino acids or less. Suitable illustrative linkers include, but are not limited to linkers comprising or consisting of the sequence SMDTSQL (SEQ ID NO:171), PSGSP ((SEQ ID NO:160), ASASA (SEQ ID NO: 161), or GGG (SEQ ID NO: 162). In certain embodiments, longer linkers such as (GGGGS)$_3$ (SEQ ID NO:163) can be used. In certain embodiments, the linker comprises or consists of the sequence SMDTSQL (SEQ ID NO:171). Various illustrative peptide amino acid linkers, peptide linkers, and other linkers are shown in Table 6.

TABLE 6

Illustrative amino acid linkers, peptide linkers, and non-peptide linkers.

| Linker | SEQ ID NO: |
|---|---|
| A | |
| G | |
| P | |
| AA | |
| GG | |
| PP | |
| AAA | |
| GGG | |
| GGGG | 164 |
| SGG | |
| GGSGGS | 165 |
| SAT | |
| PYP | |
| PSPSP | 166 |
| ASA | |
| ASASA | 167 |
| PSPSP | 168 |
| KKKK | 169 |
| RRRR | 170 |
| SMDTSQL | 171 |
| GGGGS | 172 |
| GGGGS GGGGS | 173 |
| GGGGS GGGGS GGGGS | 174 |
| GGGGS GGGGS GGGGS GGGGS | 175 |
| GGGGS GGGGS GGGGS GGGGS GGGGS | 176 |
| GGGGS GGGGS GGGGS GGGGS GGGGS GGGGS | 177 |
| 2-nitrobenzene or O-nitrobenzyl | |
| Nitropyridyl disulfide | |
| Dioleoylphosphatidylethanolamine (DOPE) | |
| S-acetylmercaptosuccinic acid | |
| 1, 4, 7, 10-tetraazacyclododecane-1, 4, 7, 10-tetracetic acid (DOTA) | |
| β-glucuronide and β-glucuronide variants | |
| Poly(alkylacrylic acid) | |
| Benzene-based linkers (for example: 2,5-Bis(hexyloxy)-1,4-bis[2,5-bis(hexyloxy)-4-formyl-phenylenevinylene]benzene) and like molecules | |
| Disulfide linkages | |
| Poly(amidoamine) or like dendrimers linking multiple target and killing peptides in one molecule | |
| Carbon nanotubes | |

TABLE 6-continued

Illustrative amino acid linkers, peptide linkers, and non-peptide linkers.

| Linker | SEQ ID NO: |
|---|---|
| Hydrazone and hydrazone variant linkers | |
| PEG of any chain length | |
| Succinate, formate, acetate butyrate, other like organic acids | |
| Aldols, alcohols, or enols | |
| Peroxides | |
| alkane or alkene groups of any chain length | |
| One or more porphyrin or dye molecules containing free amide and carboxylic acid groups | |
| One or more DNA or RNA nucleotides, including polyamine and polycarboxyl-containing variants | |
| Inulin, sucrose, glucose, or other single, di or polysaccharides | |
| Linoleic acid or other polyunsaturated fatty acids | |
| Variants of any of the above linkers containing halogen or thiol groups | |

(All amino-acid-based linkers could be L, D, combinations of L and D forms, β-form, and the like)

Protecting Groups.

While the various peptides (e.g., the targeting sequence that binds a PAC1 receptor (e.g., maxadilan or a fragment thereof), and/or the sequence effective to activate PAC1 (e.g., PACAP or a fragment thereof), and/or fusion proteins comprising both) described herein may be shown with no protecting groups. However, in certain embodiments they can bear one, two, three, four, or more protecting groups. In various embodiments, the protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus. Illustrative examples of such protected peptides include, but are not limited to:

```
                                        (SEQ ID NO: 178)
HSDGIFTDSYSSRYRKQMAVKKYLAAVLPGNSVFKECMKQKKKEFKAGK*;

(SEQ ID NO: 179)
HSDGIFAPGNSVFKECMKQKKKEFKAGK*

(SEQ ID NO: 180)
HSDGIFTSMDTSQLPGNSVFKECMKQKKKEFKAGK*;
and (SEQ ID NO: 181)
HSDGIFTPGNSVFKECMKQKKKEFKAGK*
``` where the asterisk indicates an amidated carboxyl terminus. Of course, this protecting group can be can be eliminated and/or substituted with another protecting group as described herein.

Without being bound by a particular theory, it is believed that addition of a protecting group, particularly to the carboxyl and in certain embodiments the amino terminus can improve the stability and efficacy of the peptide.

A wide number of protecting groups are suitable for this purpose. Such groups include, but are not limited to acetyl, amide, and alkyl groups with acetyl and alkyl groups being particularly suitable for N-terminal protection and amide groups being particularly suitable for carboxyl terminal protection. In certain embodiments, the protecting groups include, but are not limited to alkyl chains as in fatty acids, propionyl, formyl, and others. Certain suitable carboxyl protecting groups include amides, esters, and ether-forming protecting groups. In one embodiment, an acetyl group is used to protect the amino terminus and an amide group is used to protect the carboxyl terminus. In certain embodiments blocking groups include alkyl groups of various lengths, e.g., groups having the formula: $CH_3-(CH_2)_n-CO-$ where n ranges from about 1 to about 20, or from about 1 to about 16 or 18, or from about 3 to about 13, or from about 3 to about 10.

In certain embodiments, the acid group on the C-terminal can be blocked with an alcohol, aldehyde or ketone group and/or the N-terminal residue can have the natural amide group, or be blocked with an acyl, carboxylic acid, alcohol, aldehyde, or ketone group.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimentyl-2,6-di-axocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), cyclohexyloxy (cHxO), t-butoxymethyl (Bum), t-butoxy (tBuO), t-Butyl (tBu), acetyl (Ac), and trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis, 2nd ed.*, John Wiley & Sons, Inc. Somerset, N.J.). In illustrative embodiment, for example, acetylation is accomplished during the synthesis when the peptide is on the resin using acetic anhydride. Amide protection can be achieved by the selection of a proper resin for the synthesis. For example, a rink amide resin can be used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

Where amino acid sequences are disclosed herein, amino acid sequences comprising, one or more protecting groups, e.g., as described above (or any other commercially available protecting groups for amino acids used, e.g., in boc or fmoc peptide synthesis) are also contemplated.

Identification/Verification of Active PAC1 Receptor Agonists.

Active PAC1 receptor agonists (MAXCAPs) can be identified and/or validated using in vitro and/or in vivo screening assay, e.g., as illustrated in the examples provided herein. For example, the PAC1 receptor agonists (MAXCAPs) can be screened for radioligand binding inhibition at the PAC1 receptor, for stimulation of cAMP stimulation, intracellular substrated phosphorylation and Ca' release in a dose dependent manner similar to native $PACAP_{1-38}$ or $PACAP_{1-27}$. In certain embodiments, the PAC1 receptor agonists (MAXCAPs) can be screened for their ability to suppress appetite and food intake and/or to induce satiety and/or to suppress gastric ghrelin release. In certain embodiments the PAC1 receptor agonists (MAXCAPs) can be evaluated in vivo for their ability to suppress energy expenditure by reducing RQ, $VO_2$, $VCO_2$, total energy expenditure to identify preferred clinical candidates. The PAC1 receptor agonists (MAXCAPs) can be also be screened for their effect on adipogenesis, fatty liver, NAFLD and/or NASH.

Uses of PAC1 Receptor Agonists (MAXCAPs).

As indicated above, it is believed the PAC1 receptor agonists (MAXCAPs) described herein can be used to downregulate appetite and/or to reduce obesity; and/or to inhibit adipogenesis and/or fat accumulation; and/or to ameliorate one or more symptoms of, or to slow the progression of, or to prevent, or reverse type 2 diabetes; and/or to ameliorate one or more symptoms of atherosclerosis; and/or to slow the progression of, or to prevent, or to reverse non-alcoholic fatty liver disease (NAFLD); and/or to ameliorate one or more symptoms of, and/or to slow, and/or to prevent, and/or to reverse hepatosteatosis (fatty liver); and/or to ameliorate one or more symptoms of, and/or to slow the progression of, and/or to prevent, and/or to reverse metabolic syndrome; and/or to ameliorate one or more symptoms of, and/or to slow the progression of, and/or to prevent, and/or to reverse insulin resistance; and/or to ameliorate one or more symptoms of, and/or to slow the progression of, and/or to prevent, and/or to reverse prediabetic syndrome; and/or to ameliorate hepatosteatosis; and/or to ameliorate, and/or to prevent, and/or to reverse NASH and/or NALD, to downregulate appetite and/or to reduce obesity and/or to reduce body weight; and/or to inhibit adipogenesis and/or body fat accumulation, and/or reduce and/or regulate glucose homeostasis, and/or to improve or cure diabetes mellitus symptoms, and/or to reduce or cure inflammatory bowel diseases, and/or to reduce or cure chronic inflammatory diseases; and/or to ameliorate symptoms of and/or to treat systemic and organ-specific autoimmune diseases, and/or to reduce or cure dry eye syndrome, and/or to prevent or reduce organs, tissues and stem cells transplant rejection, and/or to improve embryo implant in uterus for in vitro fertilization, and/or to ameliorate one or more symptoms of connectivitis, and/or to slow the progression of osteoarthritis and/or rheumatoid arthritis, and/or psoriatic arthritis, and/or to prevent, or to reverse systemic hypertension; and/or to ameliorate one or more symptoms of atherosclerosis; and/or to slow the progression of, or to prevent, or to reverse non-alcoholic fatty liver disease (NAFLD), and/or NASH; and/or to ameliorate one or more symptoms of, and/or to slow, and/or to prevent, and/or to reverse hepatosteatosis (fatty liver); and/or to ameliorate one or more symptoms of, and/or to slow the progression of, and/or to prevent, and/or to reverse metabolic syndrome; and/or to ameliorate one or more symptoms of, and/or to slow the progression of, and/or to prevent, and/or to reverse insulin resistance; and/or to ameliorate one or more symptoms of, and/or to slow the progression of, and/or to prevent, and/or to reverse prediabetic syndrome; and/or to slow the progression of, and/or to prevent, and/or to reverse renal hypertension and/or chronic kidney diseases, and/or to slow the progression of, and/or to inhibit, and/or to reverse growth of tumors expressing PAC1 receptors, and/or to slow the progression of, and/or to prevent, and/or to reverse mast cell and/or basophil degranulation and release of allergic mediators, and/or to ameliorate the symptoms of, and/or to treat cystic fibrosis, and/or to ameliorate the symptoms of, and/or to treat celiac disease, and/or to slow the progression of, and/or to prevent, and/or to reverse schizophrenic and paranoid disorders, and/or to slow the progression of, and/or to prevent, and/or to reverse Alzheimer's disease, and/or to slow the progression of, and/or to ameliorate the symptoms, and/or to reverse neuromuscular dystrophy, and/or to slow the progression of, and/or to prevent, and/or to reverse neurological paralysis, and/or to slow the progression of, and/or to ameliorate the symptoms of, and/or to nerve injury paralysis, and/or to slow the progression of, and/or to ameliorate the symptoms of, and/or to reverse traumatic brain injury, and/or to ameliorate the symptoms of, and/or to reverse post traumatic stress disorder, and/or to ameliorate the symptoms of, and/or to reverse neuropathic disorders, and/or to ameliorate the symptoms of, and/or to reverse asthmatic syndrome, and/or to ameliorate the symptoms of, and/or to reverse chronic obstructive pulmonary disease, and/or to ameliorate the symptoms of, and/or to reverse lymphoproliferative disorders and/or myeloproliferative disorders, and/or to ameliorate the symptoms of, and/or to reverse thrombocytopenia, and/or to ameliorate the symptoms of, and/or to treat multiple myeloma, and/or to ameliorate the symptoms of, and/or to reverse acute or chronic nephropathies, and/or transient arterial stenosis and/or hemorrhagic shock, and/or antibiotic induced nephrotoxicity, and/or to ameliorate the symptoms of, and/or to treat polycystic kidney disease, and/or to ameliorate the symptoms of, and/or to reverse ocular hypertension, and/or glaucoma, and/or retinite pigmentosa, and/or to ameliorate the symptoms of, and/or to prevent ischemia/riperfusion of tissue and/or organs, and/or to ameliorate the symptoms of, and/or to prevent chronic fibrotic processes, and/or to ameliorate the symptoms of, and/or to reverse, and/or coupled to radionuclides or fluorescent tracers to localize, and/or to diagnose, and/or to treat cancer and metastases.

It is believed the PAC1 receptor agonists (MAXCAPs) described herein are the first compounds to target a new pathway for appetite/satiety control and have more potent and long term effects than any current pharmacological target. Furthermore, prior to the PAC1 receptor agonists (MAXCAPs) described herein there were no clinically effective anti-appetite, adipogenesis, diabetes type 2, atherosclerosis, obesity and inhibition of fat accumulation pharmacological targets in the market to date. The MAXCAPs described herein induced significant reduction of appetite, body fat accumulation, and body weight decrease in a diet induced obese mouse models. Additionally, a particularly striking effect of MAXCAPs is to treat hepatosteatosis, NAFLD and NASH in a mouse model. Currently there are no effective methods or pharmacological targets to treat these disorders.

Typically, as noted above, the PAC1 receptor agonists (MAXCAPs) described herein are administered to a subject in need thereof (e.g., a subject diagnosed with metabolic syndrome, type II diabetes, obesity, NASH/NLD, and the like).

In certain embodiments the PAC1 receptor agonists (MAXCAPs) described herein are administered in conjunction with one or more dipeptidyl peptidase IV inhibitors. It is believed that such administration, inter alia, can increase the effective half-life of the PAC1 receptor agonists and/or to provide synergic activity with respect to the desired effect (described above).

Dipeptidyl peptidase IV inhibitors are well known to those of skill in the art. Such inhibitors include, but are not limited to aminomethylpyridine (R1438, Roche), NVP DPP728 (Novartis), PSN9301 (Prosidion), isoleucine thiazolidide (P32/92, Probiodrug), denagliptin (GSK823093C, Glaxo Smithkline), sitagliptin (januvia, MK-0431, Merck), vidagliptin (galvus, LAF237, Novartis), saxgliptin (BMS-477118, Bristol-Meyers, Squibb), alogliptin (SYR-322, Takeda), NN-7201 (novoNordisk), and ALS 2-0426 (Alantos).

In certain embodiments the MAXCAPs described herein are administered in conjunction with Exendin-4, GLP-1 agonists, CGRP, Adrenomedullin, Serotonin, Amylin, VIP and VPAC1 antagonists, and/or VPAC2 agonists.

IV. Administration and Formulations.

A) Pharmaceutical Formulations.

In certain embodiments, the PAC1 receptor agonists (MAXCAPs) described herein are administered to a mammal in need thereof. In various embodiments the compositions can be administered to downregulate appetite and/or reduce obesity; and/or to inhibit adipogenesis and/or fat accumulation; and/or to ameliorate one or more symptoms of, or to slow the progression of, or to prevent, or reverse type 2 diabetes; and/or to ameliorate one or more symptoms of atherosclerosis; and/or to slow the progression of, or to prevent, or to reverse non-alcoholic fatty liver disease (NAFLD); and/or to ameliorate one or more symptoms of, and/or to slow, and/or to prevent, and/or to reverse hepatosteatosis (fatty liver); and/or to ameliorate one or more symptoms of, and/or to slow the progression of, and/or to prevent, and/or to reverse metabolic syndrome; and/or to ameliorate one or more symptoms of, and/or to slow the progression of, and/or to prevent, and/or to reverse insulin resistance; and/or to ameliorate one or more symptoms of, and/or to slow the progression of, and/or to prevent, and/or to reverse prediabetic syndrome; and/or to ameliorate hepatostatosis; and/or to ameliorate, and/or to prevent, and/or to reverse NASH and/or NAFLD.

These PAC1 receptor agonists (MAXCAPs) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, the disulfide salts of a number of delivery agents are described in PCT Publication WO 2000/059863 which is incorporated herein by reference. Similarly, acid salts of therapeutic peptides, peptoids (or other mimetics), and the like can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the PAC1 receptor agonists (MAXCAPs) described herein include halide salts, such as may be prepared using hydrochloric or hydrobromic acids. Conversely, preparation of basic salts of the PAC1 receptor agonists (MAXCAPs) described herein are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkylamine.

In various embodiments, the PAC1 receptor agonists (MAXCAPs) described herein are useful for parenteral, topical, oral, nasal (or otherwise inhaled), rectal, or local administration, such as by aerosol or transdermally prophylactic and/or therapeutic treatment as described herein. The compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The PAC1 receptor agonists (MAXCAPs) described herein can also be combined with a pharmaceutically acceptable carrier (excipient) to form a pharmacological composition. In certain embodiments, pharmaceutically acceptable carriers include those approved by a regulatory agency of the Federal or a state government or listed in the U.S. Pharmacopeia or other generally recognized pharmacopeia for use in/on animals, and more particularly in/on humans. A "carrier" refers to, for example, a diluent, adjuvant, excipient, auxiliary agent or vehicle with which an active agent of the present invention is administered.

Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disintegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., active peptide) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain therapeutic applications, the PAC1 receptor agonists (MAXCAPs) described herein are administered, e.g., topically administered or administered to a patient in need thereof to downregulate appetite and/or reduce obesity; and/or to inhibit adipogenesis and/or fat accumulation; and/or to ameliorate one or more symptoms of, or to slow the progression of, or to prevent, or reverse type 2 diabetes; and/or to ameliorate one or more symptoms of atherosclerosis; and/or to slow the progression of, or to prevent, or to reverse non-alcoholic fatty liver disease (NAFLD); and/or to ameliorate one or more symptoms of, and/or to slow, and/or to prevent, and/or to reverse hepatosteatosis (fatty liver); and/or to ameliorate one or more symptoms of, and/or to slow the progression of, and/or to prevent, and/or to reverse metabolic syndrome; and/or to ameliorate one or more symptoms of, and/or to slow the progression of, and/or to prevent, and/or to reverse insulin resistance; and/or to ameliorate one or more symptoms of, and/or to slow the progression of, and/or to prevent, and/or to reverse prediabetic syndrome; and/or to ameliorate hepatosteatosis; and/or to ameliorate, and/or to prevent, and/or to reverse NASH and/or NALD. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the PAC1 receptor agonists (MAXCAPs) described herein to effectively treat (e.g., ameliorate one or more symptoms in) the patient.

The concentration of the PAC1 receptor agonists (MAXCAPs) can vary widely, and will be selected primarily based on activity of the active ingredient(s), body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, or from about 3.5 mg/kg/day to about 7.2 mg/kg/day, or from about 7.2 mg/kg/day to about 11.0 mg/kg/day, or from about 11.0 mg/kg/day to about 15.0 mg/kg/day. In certain embodiments, dosages range from about 10 mg/kg/day to about 50 mg/kg/day. In certain embodiments, dosages range from about 20 mg to about 50 mg given orally once, twice, three times, or 4 times daily. It will be appreciated that such dosages may be varied to optimize a therapeutic and/or phophylactic regimen in a particular subject or group of subjects.

In certain embodiments, the PAC1 receptor agonists (MAXCAPs) described herein are administered to the oral cavity. This is readily accomplished by the use of lozenges, aerosol sprays, mouthwash, coated swabs, and the like.

In certain embodiments the PAC1 receptor agonists (MAXCAPs) described herein are administered systemically (e.g., orally, or as an injectable) in accordance with standard methods well known to those of skill in the art. In other preferred embodiments, the agents, can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

As indicated above, various buccal, and sublingual formulations are also contemplated.

In certain embodiments, one or more the PAC1 receptor agonists (MAXCAPs) described herein can be provided as a "concentrate", e.g., in a storage container (e.g., in a premeasured volume) ready for dilution, or in a soluble capsule ready for addition to a volume of water, alcohol, hydrogen peroxide, or other diluent.

While the use of the PAC1 receptor agonists (MAXCAPs) described herein is described with respect to use in humans, they are also suitable for animal, e.g., veterinary use. Thus certain preferred organisms include, but are not limited to humans, non-human primates, canines, equines, felines, porcines, ungulates, lagomorphs, and the like.

B) Nanoemulsion Formulations.

In certain embodiments the PAC1 receptor agonists (MAXCAPs) described herein described herein are formulated in a nanoemulsion. Nanoemulsions include, but are not limited to oil in water (O/W) nanoemulsions, and water in oil (W/O) nanoemulsions. Nanoemulsions can be defined as emulsions with mean droplet diameters ranging from about 20 to about 1000 nm. Usually, the average droplet size is between about 20 nm or 50 nm and about 500 nm. The terms sub-micron emulsion (SME) and mini-emulsion are used as synonyms.

Illustrative oil in water (O/W) nanoemulsions include, but are not limited to:

Surfactant micelles—micelles composed of small molecules surfactants or detergents (e.g., SDS/PBS/2-propanol) which are suitable for predominantly hydrophobic peptides.

Polymer micelles—micelles composed of polymer, copolymer, or block copolymer surfactants (e.g., Pluronic L64/PBS/2-propanol) which are suitable for predominantly hydrophobic peptides;

Blended micelles: micelles in which there is more than one surfactant component or in which one of the liquid phases (generally an alcohol or fatty acid compound) participates in the formation of the micelle (e.g., Octanoic acid/PBS/EtOH) which are suitable for predominantly hydrophobic peptides;

Integral peptide micelles—blended micelles in which the peptide serves as an auxiliary surfactant, forming an integral part of the micelle (e.g., amphipathic peptide/PBS/mineral oil) which are suitable for amphipathic peptides; and Pickering (solid phase) emulsions—emulsions in which the peptides are associated with the exterior of a solid nanoparticle (e.g., polystyrene nanoparticles/PBS/no oil phase) which are suitable for amphipathic peptides.

Illustrative water in oil (W/O) nanoemulsions include, but are not limited to:

Surfactant micelles—micelles composed of small molecules surfactants or detergents (e.g., dioctyl sulfosuccinate/PBS/2-propanol, isopropylmyristate/PBS/2-propanol, etc.) which are suitable for predominantly hydrophilic peptides;

Polymer micelles—micelles composed of polymer, copolymer, or block copolymer surfactants (e.g., PLURONIC® L121/PBS/2-propanol), which are suitable for predominantly hydrophilic peptides;

Blended micelles—micelles in which there is more than one surfactant component or in which one of the liquid phases (generally an alcohol or fatty acid compound) participates in the formation of the micelle (e.g., capric/caprylic diglyceride/PBS/EtOH) which are suitable for predominantly hydrophilic peptides;

Integral peptide micelles—blended micelles in which the peptide serves as an auxiliary surfactant, forming an integral part of the micelle (e.g., amphipathic peptide/PBS/polypropylene glycol) which are suitable for amphipathic peptides; and Pickering (solid phase) emulsions—emulsions in which the peptides are associated with the exterior of a solid nanoparticle (e.g., chitosan nanoparticles/no aqueous phase/mineral oil) which are suitable for amphipathic peptides.

As indicated above, in certain embodiments the nanoemulsions comprise one or more surfactants or detergents. In some embodiments the surfactant is a non-anionic detergent (e.g., a polysorbate surfactant, a polyoxyethylene ether, etc.). Surfactants that find use in the present invention include, but are not limited to surfactants such as the TWEEN®, TRITON®, and TYLOXAPOL® families of compounds.

In certain embodiments the emulsions further comprise one or more cationic halogen containing compounds, including but not limited to, cetylpyridinium chloride. In still further embodiments, the compositions further comprise one or more compounds that increase the interaction ("interaction enhancers") of the composition with microorganisms (e.g., chelating agents like ethylenediaminetetraacetic acid, or ethylenebis(oxyethylenenitrilo)tetraacetic acid in a buffer).

In some embodiments, the nanoemulsion further comprises an emulsifying agent to aid in the formation of the emulsion. Emulsifying agents include compounds that aggregate at the oil/water interface to form a kind of continuous membrane that prevents direct contact between two adjacent droplets. Certain embodiments of the present invention feature oil-in-water emulsion compositions that may readily be diluted with water to a desired concentration without impairing their anti-pathogenic properties.

In addition to discrete oil droplets dispersed in an aqueous phase, certain oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water).

These lipid structures are formed as a result of hydrophobic forces that drive apolar residues (e.g., long hydrocarbon chains) away from water. The above lipid preparations can generally be described as surfactant lipid preparations (SLPs). SLPs are minimally toxic to mucous membranes and are believed to be metabolized within the small intestine (see e.g., Hamouda et al., (1998) *J. Infect. Disease* 180: 1939).

In certain embodiments the emulsion comprises a discontinuous oil phase distributed in an aqueous phase, a first component comprising an alcohol and/or glycerol, and a second component comprising a surfactant or a halogen-containing compound. The aqueous phase can comprise any type of aqueous phase including, but not limited to, water (e.g., dionized water, distilled water, tap water) and solutions (e.g., phosphate buffered saline solution, or other buffer systems). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In certain embodiments, the oil phase comprises 30-90 vol % of the oil-in-water emulsion (i.e., constitutes 30-90% of the total volume of the final emulsion), more preferably 50-80%.

In certain embodiments the alcohol, when present, is ethanol.

While the present invention is not limited by the nature of the surfactant, in some preferred embodiments, the surfactant is a polysorbate surfactant (e.g., TWEEN 20®, TWEEN 40®, TWEEN 60®, and TWEEN 80®), a pheoxypolyethoxyethanol (e.g., TRITON® X-100, X-301, X-165, X-102, and X-200, and TYLOXAPOL®), or sodium dodecyl sulfate, and the like.

In certain embodiments a halogen-containing component is present. the nature of the halogen-containing compound, in some preferred embodiments the halogen-containing compound comprises a chloride salt (e.g., NaCl, KCl, etc.), a cetylpyridinium halide, a cetyltrimethylammonium halide, a cetyldimethylethylammonium halide, a cetyldimethylbenzylammonium halide, a cetyltributylphosphonium halide, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyldimethylethylammonium bromide, cetyltributylphosphonium bromide, dodecyltrimethylammonium bromide, tetradecyltrimethylammonium bromide, and the like In certain embodiments the emulsion comprises a quaternary ammonium compound. Quaternary ammonium compounds include, but are not limited to, N-alkyldimethyl benzyl ammonium saccharinate, 1,3,5-triazine-1,3,5(2H,4H, 6H)-triethanol; 1-decanaminium, N-decyl-N,N-dimethyl-, chloride (or) didecyl dimethyl ammonium chloride; 2-(2-(p-(diisobuyl)cresosxy)ethoxy)ethyl dimethyl benzyl ammonium chloride; 2-(2-(p-(diisobutyl)phenoxy)ethoxy)ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride;

diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quatemium 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

Nanoemulsion formulations and methods of making such are well known to those of skill in the art and described for example in U.S. Pat. Nos. 7,476,393, 7,468,402, 7,314,624, 6,998,426, 6,902,737, 6,689,371, 6,541,018, 6,464,990, 6,461,625, 6,419,946, 6,413,527, 6,375,960, 6,335,022, 6,274,150, 6,120,778, 6,039,936, 5,925,341, 5,753,241, 5,698,219, an d5,152,923 and in Fanun et al. (2009) *Microemulsions: Properties and Applications* (Surfactant Science), CRC Press, Boca Ratan, Fl.

VI. Kits.

In another embodiment this invention provides kits to downregulate appetite and/or to reduce obesity; and/or to inhibit adipogenesis and/or fat accumulation; and/or to ameliorate one or more symptoms of, or to slow the progression of, or to prevent, or reverse type 2 diabetes; and/or to ameliorate one or more symptoms of atherosclerosis; and/or to slow the progression of, or to prevent, or to reverse non-alcoholic fatty liver disease (NAFLD); and/or to ameliorate one or more symptoms of, and/or to slow, and/or to prevent, and/or to reverse hepatosteatosis (fatty liver); and/ or to ameliorate one or more symptoms of, and/or to slow the progression of, and/or to prevent, and/or to reverse metabolic syndrome; and/or to ameliorate one or more symptoms of, and/or to slow the progression of, and/or to prevent, and/or to reverse insulin resistance; and/or to ameliorate one or more symptoms of, and/or to slow the progression of, and/or to prevent, and/or to reverse prediabetic syndrome; and/or to ameliorate hepatostatosis; and/or to ameliorate, and/or to prevent, and/or to reverse NASH and/or NAFLD.

The kits typically comprise a container containing one or more of the PAC1 receptor agonists (MAXCAPs) described herein. In certain embodiments the PAC1 receptor agonists can be provided in a unit dosage formulation (e.g., suppository, tablet, caplet, patch, etc.) and/or may be optionally combined with one or more pharmaceutically acceptable excipients.

In addition, the kits optionally include labeling and/or instructional materials providing directions (i.e., protocols) for the practice of the methods or use of the "therapeutics" or "prophylactics" described herein. Certain instructional materials describe the use of one or more active agent(s) of this invention to therapeutically or prophylactically to down-regulate appetite and/or to reduce obesity; and/or to inhibit adipogenesis and/or fat accumulation; and/or to ameliorate one or more symptoms of, or to slow the progression of, or to prevent, or reverse type 2 diabetes; and/or to ameliorate one or more symptoms of atherosclerosis; and/or to slow the progression of, or to prevent, or to reverse non-alcoholic fatty liver disease (NAFLD); and/or to ameliorate one or more symptoms of, and/or to slow, and/or to prevent, and/or to reverse hepatosteatosis (fatty liver); and/or to ameliorate one or more symptoms of, and/or to slow the progression of, and/or to prevent, and/or to reverse metabolic syndrome; and/or to ameliorate one or more symptoms of, and/or to slow the progression of, and/or to prevent, and/or to reverse insulin resistance; and/or to ameliorate one or more symptoms of, and/or to slow the progression of, and/or to prevent, and/or to reverse prediabetic syndrome; and/or to ameliorate hepatosteatosis; and/or to ameliorate, and/or to prevent, and/or to reverse NASH and/or NAFL LD. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Preparation and Evaluation of PAC1 Receptor Agonists

We have stably transfected PAC1 receptors into a N|H3T3 cell line. The pCDL-SRd/Neo plasmid containing the human PAC1 insert was linearized at its Aat ll restriction site within the Ampicillin-resistance gene and stably transfected into NIH/3T3 fibroblasts using an electroporator set at 475 V by 1 msec for four pulses on $2 \times 10^7$ cells in 0.25 ml containing 20 µg vector, Wt cDNA, and 500 µg/ml salmon sperm. Geneticin was used to select clones. Ten clones were subjected to radioligand binding. The clones that exhibited the highest efficacy for adenylyl cyclase and radioligand binding inhibition were selected for further study.

Both MAXCAP 1 (SEQ ID NO:5) and MAXCAP 4 (SEQ ID NO:6) stimulated CAMP in a dose dependent manner similarly to native $PACAP_{1-38}$ and $PACAP_{1-27}$ (see, e.g., FIG. 1, and Table 7).

TABLE 7

Cyclic AMP stimulation by maxcap 1 and maxcap 4 compared to PACAP.

|  | MAXCAP 4 cAMP (fmol) | PACAP Mean (fmol) |
| --- | --- | --- |
| Cells Only | 520.7485 | 520.7485 |
| 1 nM | 3614/611 | 3310/137 |
| 10 nM | 4064.583 | 3614.611 |
| 100 nM | 6400 | 4247.405 |
| 1 µM | 6400 | 7201.421 |
| 10 µM | 5779.348 | 6891.447 |

TABLE 7-continued

Cyclic AMP stimulation by maxcap 1 and maxcap 4 compared to PACAP.

|            | MAXCAP 1 cAMP (fmol) | PACAP Mean (fmol) |
|------------|----------------------|-------------------|
| Cells Only | 520.7485             | 520.7485          |
| 1 nM       | 3167.656             | 3310.137          |
| 10 nM      | 6219.068             | 3614.611          |
| 100 nM     | 4706.616             | 4247.405          |

Figure 2:
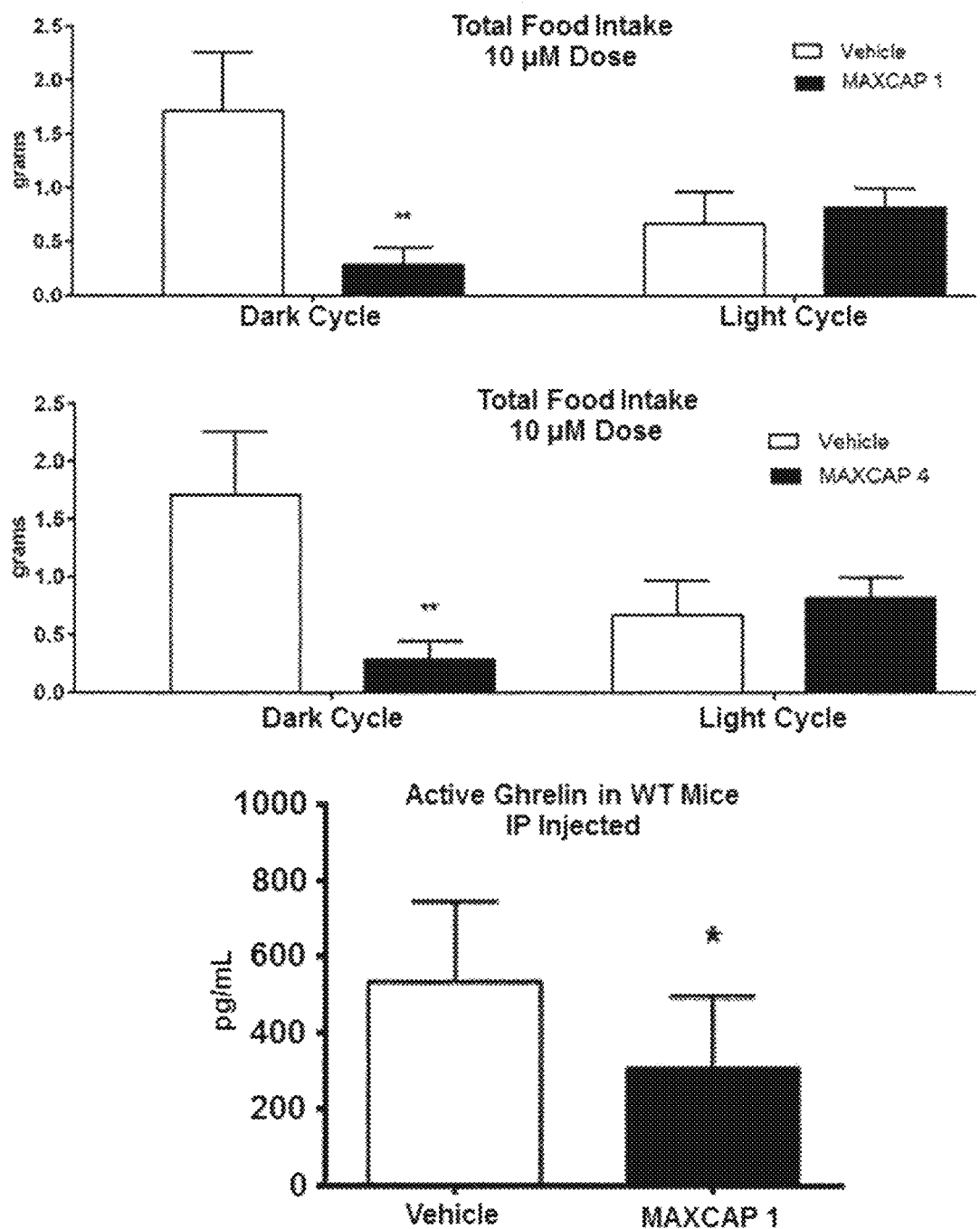
FIG. 2 illustrates the effect of MAXCAP 1 and MAXCAP 4 on food intake and gastric ghrelin release.

We have shown that these newly designed "MAXCAP" compounds, that are PAC1 specific agonists, suppress appetite and food intake and induce satiety through suppression of gastric ghrelin release (see, FIG. 2). We utilized the Promethion Metabolic cage system to measure 24 hour total food intake in 12 hour (dark/light cycle) periods.

Figure 3:
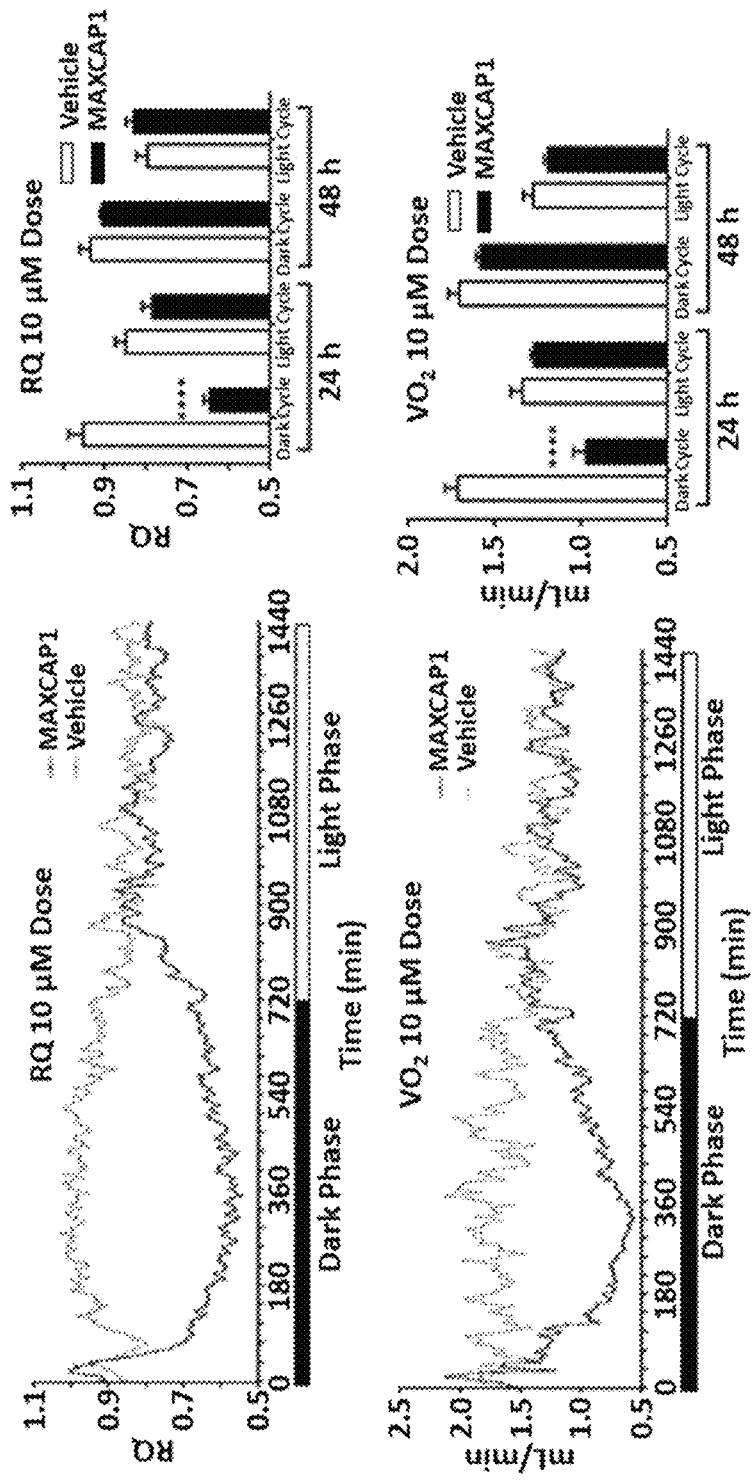
FIG. 3 illustrates the effect of MAXCAP 1 and MAXCAP 4 on RQ, VO$_2$, VCO$_2$, and total energy expenditure (TEE), coarse activity index, and mean locomotion speed.

We have shown that these novel MAXCAP compounds that are PAC1 specific agonists suppress energy expenditure by reducing RQ, $VO_2$, $VCO_2$, and Total Energy Expenditure, Total activity index, coarse activity index, fine activity index and mean locomotion speed (see, FIG. 3). The RQ index is in the 0.6 zone for most of the dark phase after injection, a ketosis state, burning fat mass. We utilized the Promethion Metabolic cage system to gather our results.

Figure 4:
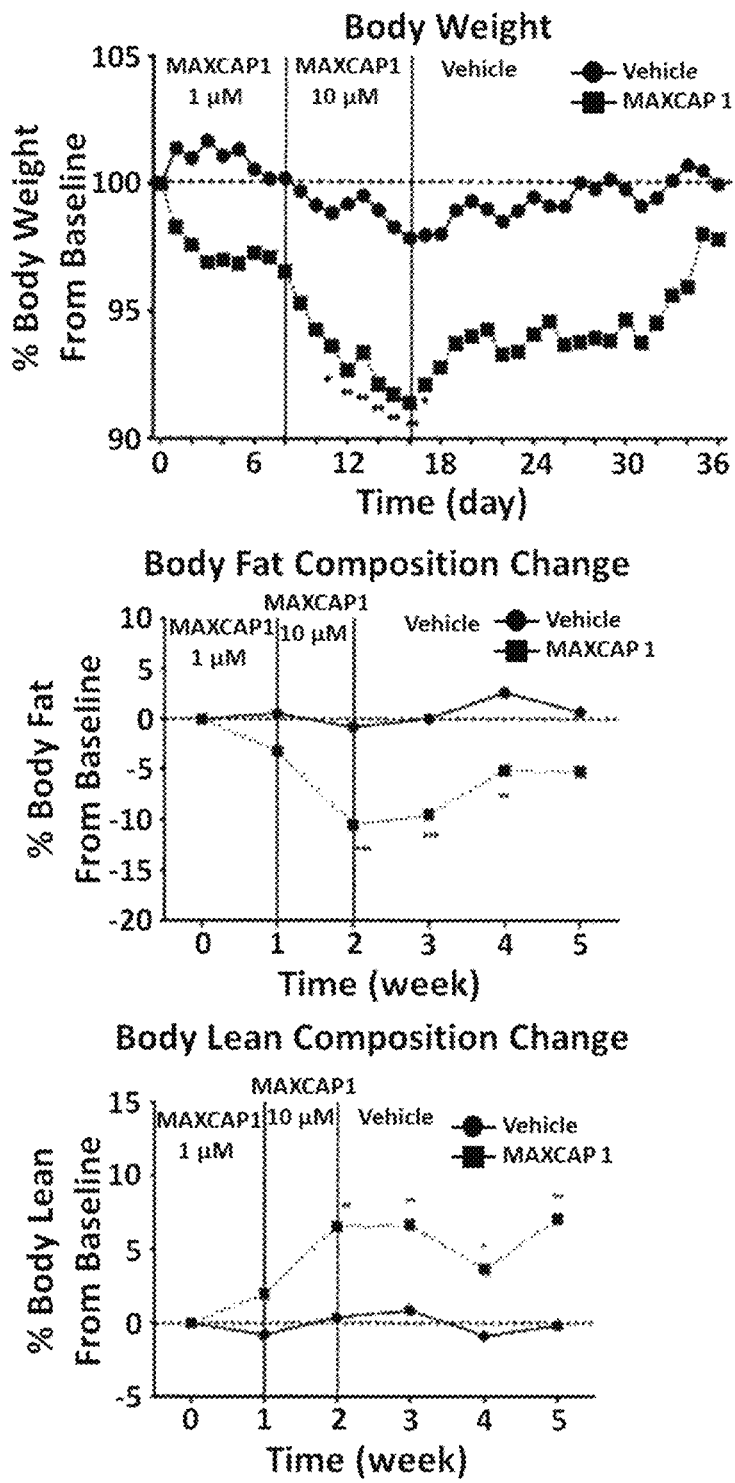
FIG. 4 illustrates the effect of MAXCAP 1 on body weight, body fat, and body lean composition.

We have shown that these novel MAXCAP compounds that are PAC1 specific agonists are potential anti-obesity targets (see, e.g., FIG. 4). We injected these MAXCAP compounds in DIO WT mice to measure body weight and analyze body fat and lean mass composition.

Figure 5:
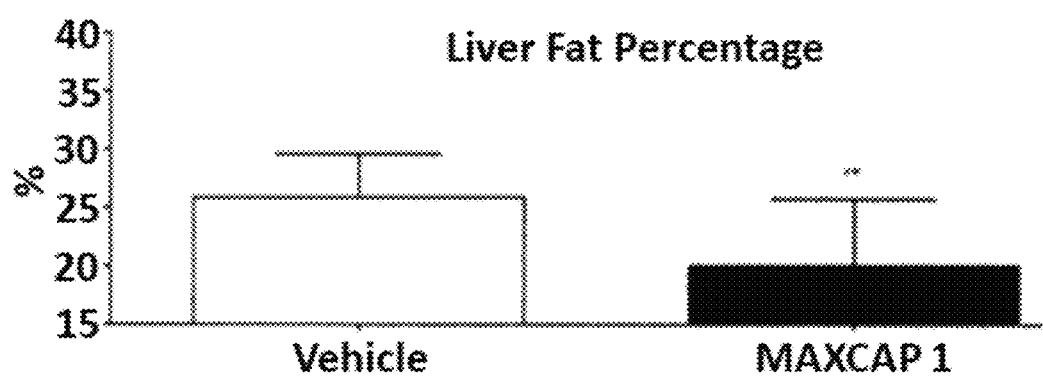
FIG. 5 illustrates the effect of MAXCAP 1 on liver cirrhosis and NASH/NAFLD.

We have shown that these novel MAXCAP compounds, that are PAC1 specific agonists, can potentially treat Non-alcoholic steatohepatitis (NASH), non-alcoholic steatohepatitis (NAFLD) and liver fibrosis. We injected these MAXCAP compounds in DIO WT mice and measured hepatic fat in the liver (see, e.g., FIG. 5). Vehicle treated DIO mice had a significant cirrhosis and hepatic fat composition contributing to a NASH/NAFLD diagnosis, as analyzed by hematoxylin and eosin (H&E) staining, however, treatment by PACAP caused a significant reduction in liver cirrhosis and NASH/NAFLD.

Figure 6:
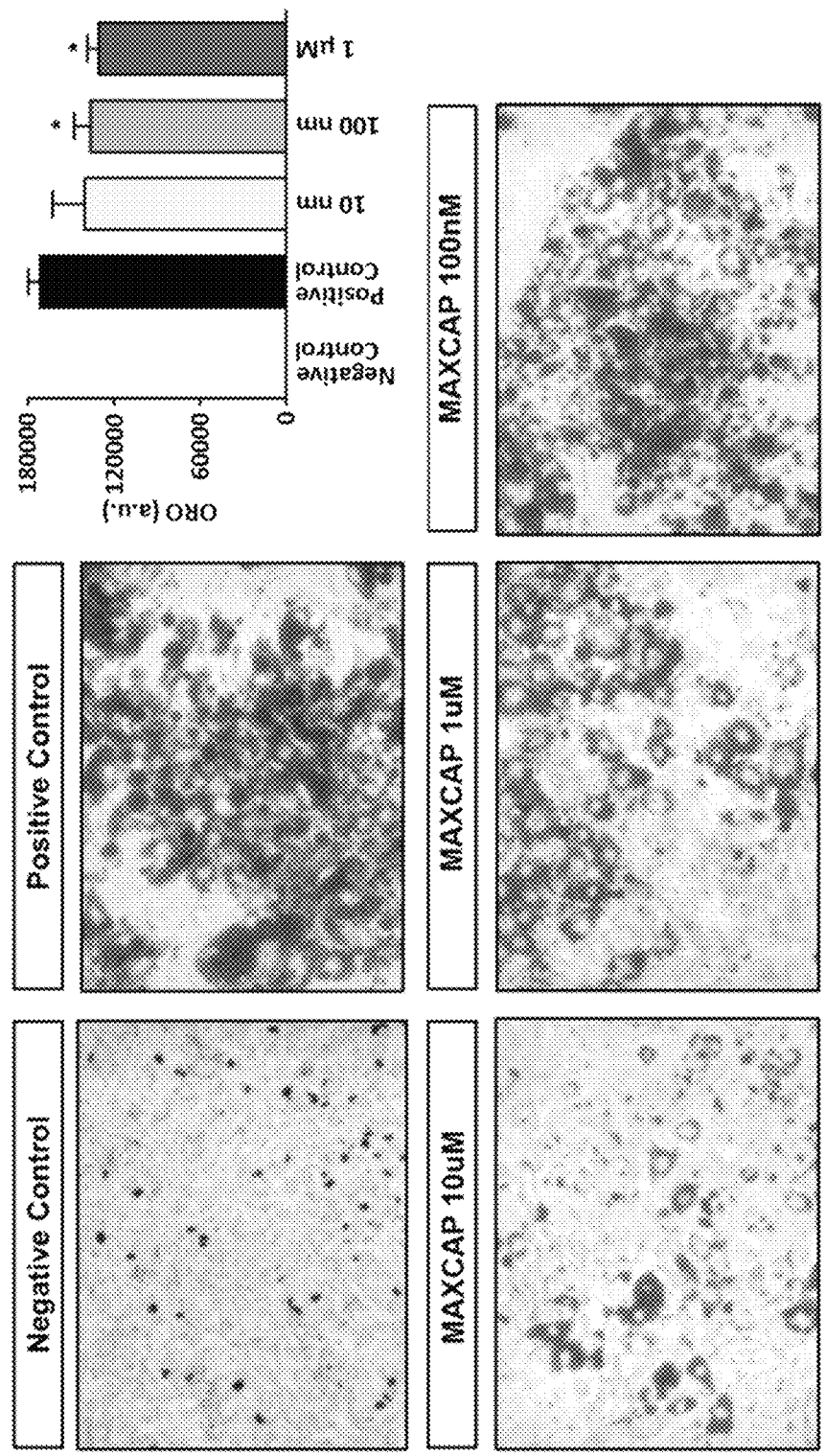
FIG. 6 illustrates the effect of MAXCAP 1 on adipogenesis in hepatocytes and adipocytes.

We have shown that these novel MAXCAP compounds that are PAC1 specific agonists, are inhibitors of adipogenesis in hepatocytes and adipocytes (see, e.g., FIG. 6). NIH 3T3-L1 pre-adipocytes were differentiated in 4.5 mg/mL glucose, 50 mM dexamethasone, 40.5 mM IBMX, and 150 mg/mL insulin differentiation medium for 2 weeks. $PACAP_{1-27}$ was applied daily to differentiating cells in a dose-dependent fashion. Visualization of lipid accumulation by Oil Red 0 staining. Quantification by ImageJ image Processing Software. Scale bars, 200 μm. Images viewed under 20× magnification. N=3-4 per group. a.u., arbitrary units. *P<0.05, P<0.01, *P<0.001 compared to positive control.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A PAC1 receptor agonist, said agonist comprising:
a targeting sequence that binds to the PAC1 receptor attached to a peptide that activates PAC1 signaling, wherein:
said targeting sequence comprises a maxadilan peptide or fragment thereof effective to bind a PAC1 receptor; and
said peptide that activates PAC1 signaling comprises PACAP$_{1-38}$ or a fragment thereof, effective to activate PAC1 signaling, wherein:
said peptide that activates PAC1 signaling comprises an R to A mutation at residue 12 of said PACAP$_{1-38}$; or
said peptide that activates PAC1 signaling comprises an R to K mutation at residue 12 of said PACAP$_{1-38}$; or
said peptide that activates PAC1 signaling comprises a K to A mutation at residue 15 of said PACAP$_{1-38}$.

2. The PAC1 receptor agonist of claim 1, wherein the amino acid sequence of said peptide that activates PAC1 signaling consists of an amino acid sequence selected from the group consisting of HSDGIFTDSYSRYRKA (SEQ ID NO: 119),

```
                                          (SEQ ID NO: 123)
HSDGIFTDSYSA,
and
                                          (SEQ ID NO: 124)
HSDGIFTDSYSK
```

3. The PAC1 receptor agonist of claim 1, wherein said PAC1 receptor agonist, when administered to a mammal, is effective to downregulate appetite, reduce body weight, and/or slow the progression of NAFLD and/or NASH.

4. The PAC1 receptor agonist of claim 1, wherein the amino acid sequence of said targeting sequence consists of an amino acid sequence selected from the group consisting of

```
                                          (SEQ ID NO: 26)
MKQILLISLVVVLAVFAFNVAEGCDATCQFRKAIDDCQKQAHHSN
VLQTSVQTTATFTSMDTSQLPGNSVFKECMKQKKKEFSSGK, (SEQ ID NO: 27)
KQILLISLVVVLAVFAFNVAEGCDATCQFRKAIDDCQKQAHHSNV
LQTSVQTTATFTSMDTSQLPGNSVFKECMKQKKKEFSSGK, (SEQ ID NO: 28)
QILLISLVVVLAVFAFNVAEGCDATCQFRKAIDDCQKQAHHSNVL
QTSVQTTATFTSMDTSQLPGNSVFKECMKQKKKEFSSGK, (SEQ ID NO: 29)
ILLISLVVVLAVFAFNVAEGCDATCQFRKAIDDCQKQAHHSNVLQ
TSVQTTATFTSMDTSQLPGNSVFKECMKQKKKEFSSGK, (SEQ ID NO: 30)
LLISLVVVLAVFAFNVAEGCDATCQFRKAIDDCQKQAHHSNVLQT
SVQTTATFTSMDTSQLPGNSVFKECMKQKKKEFSSGK, (SEQ ID NO: 31)
LISLVVVLAVFAFNVAEGCDATCQFRKAIDDCQKQAHHSNVLQTS
VQTTATFTSMDTSQLPGNSVFKECMKQKKKEFSSGK, (SEQ ID NO: 32)
ISLVVVLAVFAFNVAEGCDATCQFRKAIDDCQKQAHHSNVLQTSV
QTTATFTSMDTSQLPGNSVFKECMKQKKKEFSSGK, (SEQ ID NO: 33)
SLVVVLAVFAFNVAEGCDATCQFRKAIDDCQKQAHHSNVLQTSVQ
TTATFTSMDTSQLPGNSVFKECMKQKKKEFSSGK, (SEQ ID NO: 34)
LVVVLAVFAFNVAEGCDATCQFRKAIDDCQKQAHHSNVLQTSVQT
TATFTSMDTSQLPGNSVFKECMKQKKKEFSSGK, (SEQ ID NO: 35)
VVVLAVFAFNVAEGCDATCQFRKAIDDCQKQAHHSNVLQTSVQTT
ATFTSMDTSQLPGNSVFKECMKQKKKEFSSGK, (SEQ ID NO: 36)
VVLAVFAFNVAEGCDATCQFRKAIDDCQKQAHHSNVLQTSVQTTA
TFTSMDTSQLPGNSVFKECMKQKKKEFSSGK, (SEQ ID NO: 37)
VLAVFAFNVAEGCDATCQFRKAIDDCQKQAHHSNVLQTSVQTTAT
FTSMDTSQLPGNSVFKECMKQKKKEFSSGK, (SEQ ID NO: 38)
LAVFAFNVAEGCDATCQFRKAIDDCQKQAHHSNVLQTSVQTTATF
TSMDTSQLPGNSVFKECMKQKKKEFSSGK, (SEQ ID NO: 39)
AVFAFNVAEGCDATCQFRKAIDDCQKQAHHSNVLQTSVQTTATFT
SMDTSQLPGNSVFKECMKQKKKEFSSGK, (SEQ ID NO: 40)
VFAFNVAEGCDATCQFRKAIDDCQKQAHHSNVLQTSVQTTATFTS
MDTSQLPGNSVFKECMKQKKKEFSSGK, (SEQ ID NO: 41)
FAFNVAEGCDATCQFRKAIDDCQKQAHHSNVLQTSVQTTATFTSM
DTSQLPGNSVFKECMKQKKKEFSSGK, (SEQ ID NO: 42)
AFNVAEGCDATCQFRKAIDDCQKQAHHSNVLQTSVQTTATFTSMD
TSQLPGNSVFKECMKQKKKEFSSGK, (SEQ ID NO: 43)
FNVAEGCDATCQFRKAIDDCQKQAHHSNVLQTSVQTTATFTSMDT
SQLPGNSVFKECMKQKKKEFSSGK, (SEQ ID NO: 44)
NVAEGCDATCQFRKAIDDCQKQAHHSNVLQTSVQTTATFTSMDTS
QLPGNSVFKECMKQKKKEFSSGK, (SEQ ID NO: 45)
VAEGCDATCQFRKAIDDCQKQAHHSNVLQTSVQTTATFTSMDTSQ
LPGNSVFKECMKQKKKEFSSGK, (SEQ ID NO: 46)
AEGCDATCQFRKAIDDCQKQAHHSNVLQTSVQTTATFTSMDTSQL
PGNSVFKECMKQKKKEFSSGK, (SEQ ID NO: 47)
EGCDATCQFRKAIDDCQKQAHHSNVLQTSVQTTATFTSMDTSQLP
GNSVFKECMKQKKKEFSSGK, (SEQ ID NO: 48)
GCDATCQFRKAIDDCQKQAHHSNVLQTSVQTTATFTSMDTSQLPG
NSVFKECMKQKKKEFSSGK, (SEQ ID NO: 49)
CDATCQFRKAIDDCQKQAHHSNVLQTSVQTTATFTSMDTSQLPGN
SVFKECMKQKKKEFSSGK, (SEQ ID NO: 50)
DATCQFRKAIDDCQKQAHHSNVLQTSVQTTATFTSMDTSQLPGNS
VFKECMKQKKKEFSSGK, (SEQ ID NO: 51)
ATCQFRKAIDDCQKQAHHSNVLQTSVQTTATFTSMDTSQLPGNSV
FKECMKQKKKEFSSGK, (SEQ ID NO: 52)
TCQFRKAIDDCQKQAHHSNVLQTSVQTTATFTSMDTSQLPGNSVF
KECMKQKKKEFSSGK, (SEQ ID NO: 53)
CQFRKAIDDCQKQAHHSNVLQTSVQTTATFTSMDTSQLPGNSVFK
ECMKQKKKEFSSGK,
```

(SEQ ID NO: 54)
QFRKAIDDCQKQAHHSNVLQTSVQTTATFTSMDTSQLPGNSVFKE
CMKQKKKEFSSGK, (SEQ ID NO: 55)
FRKAIDDCQKQAHHSNVLQTSVQTTATFTSMDTSQLPGNSVFKEC
MKQKKKEFSSGK, (SEQ ID NO: 56)
RKAIDDCQKQAHHSNVLQTSVQTTATFTSMDTSQLPGNSVFKECM
KQKKKEFSSGK, (SEQ ID NO: 57)
KAIDDCQKQAHHSNVLQTSVQTTATFTSMDTSQLPGNSVFKECMK
QKKKEFSSGK, (SEQ ID NO: 58)
AIDDCQKQAHHSNVLQTSVQTTATFTSMDTSQLPGNSVFKECMKQ
KKKEFSSGK, (SEQ ID NO: 59)
IDDCQKQAHHSNVLQTSVQTTATFTSMDTSQLPGNSVFKECMQK
KKEFSSGK, (SEQ ID NO: 60)
DDCQKQAHHSNVLQTSVQTTATFTSMDTSQLPGNSVFKECMKQKK
KEFSSGK, (SEQ ID NO: 61)
DCQKQAHHSNVLQTSVQTTATFTSMDTSQLPGNSVFKECMKQKKK
EFSSGK, (SEQ ID NO: 62)
CQKQAHHSNVLQTSVQTTATFTSMDTSQLPGNSVFKECMKQKKKE
FSSGK, (SEQ ID NO: 63)
QKQAHHSNVLQTSVQTTATFTSMDTSQLPGNSVFKECMKQKKKEF
SSGK, (SEQ ID NO: 64)
KQAHHSNVLQTSVQTTATFTSMDTSQLPGNSVFKECMKQKKKEFS
SGK, (SEQ ID NO: 65)
QAHHSNVLQTSVQTTATFTSMDTSQLPGNSVFKECMKQKKKEFSS
GK, (SEQ ID NO: 66)
AHHSNVLQTSVQTTATFTSMDTSQLPGNSVFKECMKQKKKEFSSG
K, (SEQ ID NO: 67)
HHSNVLQTSVQTTATFTSMDTSQLPGNSVFKECMKQKKKEFSSGK, (SEQ ID NO: 68)
HSNVLQTSVQTTATFTSMDTSQLPGNSVFKECMKQKKKEFSSGK, (SEQ ID NO: 69)
SNVLQTSVQTTATFTSMDTSQLPGNSVFKECMKQKKKEFSSGK, (SEQ ID NO: 70)
NVLQTSVQTTATFTSMDTSQLPGNSVFKECMKQKKKEFSSGK, (SEQ ID NO: 71)
VLQTSVQTTATFTSMDTSQLPGNSVFKECMKQKKKEFSSGK, (SEQ ID NO: 72)
LQTSVQTTATFTSMDTSQLPGNSVFKECMKQKKKEFSSGK, (SEQ ID NO: 73)
QTSVQTTATFTSMDTSQLPGNSVFKECMKQKKKEFSSGK, (SEQ ID NO: 74)
TSVQTTATFTSMDTSQLPGNSVFKECMKQKKKEFSSGK, (SEQ ID NO: 75)
SVQTTATFTSMDTSQLPGNSVFKECMKQKKKEFSSGK, (SEQ ID NO: 76)
VQTTATFTSMDTSQLPGNSVFKECMKQKKKEFSSGK, (SEQ ID NO: 77)
QTTATFTSMDTSQLPGNSVFKECMKQKKKEFSSGK, (SEQ ID NO: 78)
TTATFTSMDTSQLPGNSVFKECMKQKKKEFSSGK, (SEQ ID NO: 79)
GNSVFKECMKQKKKEFSSGK, (SEQ ID NO: 80)
NSVFKECMKQKKKEFSSGK, (SEQ ID NO: 81)
SVFKECMKQKKKEFSSGK, (SEQ ID NO: 82)
VFKECMKQKKKEFSSGK, (SEQ ID NO: 83)
FKECMKQKKKEFSSGK, (SEQ ID NO: 84)
KECMKQKKKEFSSGK, (SEQ ID NO: 85)
ECMKQKKKEFSSGK, (SEQ ID NO: 86)
CMKQKKKEFSSGK, (SEQ ID NO: 87)
MKQKKKEFSSGK, (SEQ ID NO: 88)
KQKKKEFSSGK, (SEQ ID NO: 89)
QKKKEFSSGK, (SEQ ID NO: 90)
KKKEFSSGK, (SEQ ID NO: 91)
KKEFSSGK, (SEQ ID NO: 92)
KEFSSGK, (SEQ ID NO: 93)
EFSSGK,
and (SEQ ID NO: 94)
FSSGK.

5. A pharmaceutical composition comprising a PAC1 receptor agonist of claim 1 in a pharmaceutically acceptable carrier.

6. The composition of claim 5, wherein said composition is formulated for administration by a modality selected from the group consisting of intraperitoneal administration, topical administration, oral administration, inhalation administration, transdermal administration, subdermal depot administration, and rectal administration.

7. A PAC1 receptor agonist, said agonist comprising:
 a targeting sequence that binds to the PAC1 receptor attached to a peptide that activates PAC1 signaling, wherein:
  said peptide that activates PAC1 signaling comprises PACAP$_{1-38}$ or a fragment thereof, effective to activate PAC1 signaling, wherein said PACAP$_{1-38}$ or fragment thereof optionally comprises an amino acid deletion, or substitution; and
 the amino acid sequence of said targeting sequence consists of an amino acid sequence selected from the group consisting of (SEQ ID NO: 26)
MKQILLISLVVVLAVFAFNVAEGCDATCQFRKAIDDCQKQAHHSNVLQTSV
QTTATFTSMDTSQLPGNSVFKECMKQKKKEFSSGK, (SEQ ID NO: 27)
KQILLISLVVVLAVFAFNVAEGCDATCQFRKAIDDCQKQAHHSNVLQTSVQ
TTATFTSMDTSQLPGNSVFKECMKQKKKEFSSGK, (SEQ ID NO: 28)
QILLISLVVVLAVFAFNVAEGCDATCQFRKAIDDCQKQAHHSNVLQTSVQT
TATFTSMDTSQLPGNSVFKECMKQKKKEFSSGK, (SEQ ID NO: 29)
ILLISLVVVLAVFAFNVAEGCDATCQFRKAIDDCQKQAHHSNVLQTSVQTT
ATFTSMDTSQLPGNSVFKECMKQKKKEFSSGK, (SEQ ID NO: 30)
LLISLVVVLAVFAFNVAEGCDATCQFRKAIDDCQKQAHHSNVLQTSVQTTA
TFTSMDTSQLPGNSVFKECMKQKKKEFSSGK, (SEQ ID NO: 31)
LISLVVVLAVFAFNVAEGCDATCQFRKAIDDCQKQAHHSNVLQTSVQTTAT
FTSMDTSQLPGNSVFKECMKQKKKEFSSGK, (SEQ ID NO: 32)
ISLVVVLAVFAFNVAEGCDATCQFRKAIDDCQKQAHHSNVLQTSVQTTATF
TSMDTSQLPGNSVFKECMKQKKKEFSSGK, (SEQ ID NO: 33)
SLVVVLAVFAFNVAEGCDATCQFRKAIDDCQKQAHHSNVLQTSVQTTATFT
SMDTSQLPGNSVFKECMKQKKKEFSSGK, (SEQ ID NO: 34)
LVVVLAVFAFNVAEGCDATCQFRKAIDDCQKQAHHSNVLQTSVQTTATFTS
MDTSQLPGNSVFKECMKQKKKEFSSGK, (SEQ ID NO: 35)
VVVLAVFAFNVAEGCDATCQFRKAIDDCQKQAHHSNVLQTSVQTTATFTSM
DTSQLPGNSVFKECMKQKKKEFSSGK, (SEQ ID NO: 36)
VVLAVFAFNVAEGCDATCQFRKAIDDCQKQAHHSNVLQTSVQTTATFTSMD
TSQLPGNSVFKECMKQKKKEFSSGK, (SEQ ID NO: 37)
VLAVFAFNVAEGCDATCQFRKAIDDCQKQAHHSNVLQTSVQTTATFTSMDT
SQLPGNSVFKECMKQKKKEFSSGK, (SEQ ID NO: 38)
LAVFAFNVAEGCDATCQFRKAIDDCQKQAHHSNVLQTSVQTTATFTSMDTS
QLPGNSVFKECMKQKKKEFSSGK, (SEQ ID NO: 39)
AVFAFNVAEGCDATCQFRKAIDDCQKQAHHSNVLQTSVQTTATFTSMDTSQ
LPGNSVFKECMKQKKKEFSSGK, (SEQ ID NO: 40)
VFAFNVAEGCDATCQFRKAIDDCQKQAHHSNVLQTSVQTTATFTSMDTSQL
PGNSVFKECMKQKKKEFSSGK, (SEQ ID NO: 41)
FAFNVAEGCDATCQFRKAIDDCQKQAHHSNVLQTSVQTTATFTSMDTSQLP
GNSVFKECMKQKKKEFSSGK, (SEQ ID NO: 42)
AFNVAEGCDATCQFRKAIDDCQKQAHHSNVLQTSVQTTATFTSMDTSQLPG
NSVFKECMKQKKKEFSSGK, (SEQ ID NO: 43)
FNVAEGCDATCQFRKAIDDCQKQAHHSNVLQTSVQTTATFTSMDTSQLPGN
SVFKECMKQKKKEFSSGK, (SEQ ID NO: 44)
NVAEGCDATCQFRKAIDDCQKQAHHSNVLQTSVQTTATFTSMDTSQLPGNS
VFKECMKQKKKEFSSGK, (SEQ ID NO: 45)
VAEGCDATCQFRKAIDDCQKQAHHSNVLQTSVQTTATFTSMDTSQLPGNSV
FKECMKQKKKEFSSGK, (SEQ ID NO: 46)
AEGCDATCQFRKAIDDCQKQAHHSNVLQTSVQTTATFTSMDTSQLPGNSVF
KECMKQKKKEFSSGK, (SEQ ID NO: 47)
EGCDATCQFRKAIDDCQKQAHHSNVLQTSVQTTATFTSMDTSQLPGNSVFK
ECMKQKKKEFSSGK, (SEQ ID NO: 48)
GCDATCQFRKAIDDCQKQAHHSNVLQTSVQTTATFTSMDTSQLPGNSVFKE
CMKQKKKEFSSGK, (SEQ ID NO: 49)
CDATCQFRKAIDDCQKQAHHSNVLQTSVQTTATFTSMDTSQLPGNSVFKEC
MKQKKKEFSSGK, (SEQ ID NO: 50)
DATCQFRKAIDDCQKQAHHSNVLQTSVQTTATFTSMDTSQLPGNSVFKECM
KQKKKEFSSGK, (SEQ ID NO: 51)
ATCQFRKAIDDCQKQAHHSNVLQTSVQTTATFTSMDTSQLPGNSVFKECMK
QKKKEFSSGK, (SEQ ID NO: 52)
TCQFRKAIDDCQKQAHHSNVLQTSVQTTATFTSMDTSQLPGNSVFKECMKQ
KKKEFSSGK, (SEQ ID NO: 53)
CQFRKAIDDCQKQAHHSNVLQTSVQTTATFTSMDTSQLPGNSVFKECMKQK
KKEFSSGK, (SEQ ID NO: 54)
QFRKAIDDCQKQAHHSNVLQTSVQTTATFTSMDTSQLPGNSVFKECMKQKK
KEFSSGK, (SEQ ID NO: 55)
FRKAIDDCQKQAHHSNVLQTSVQTTATFTSMDTSQLPGNSVFKECMKQKKK
EFSSGK, (SEQ ID NO: 56)
RKAIDDCQKQAHHSNVLQTSVQTTATFTSMDTSQLPGNSVFKECMKQKKKE
FSSGK, (SEQ ID NO: 57)
KAIDDCQKQAHHSNVLQTSVQTTATFTSMDTSQLPGNSVFKECMKQKKKEF
SSGK, -continued

```
                                               (SEQ ID NO: 58)
AIDDCQKQAHHSNVLQTSVQTTATFTSMDTSQLPGNSVFKECMKQKKKEFS
SGK, (SEQ ID NO: 59)
IDDCQKQAHHSNVLQTSVQTTATFTSMDTSQLPGNSVFKECMKQKKKEFSS
GK, (SEQ ID NO: 60)
DDCQKQAHHSNVLQTSVQTTATFTSMDTSQLPGNSVFKECMKQKKKEFSSG
K, (SEQ ID NO: 61)
DCQKQAHHSNVLQTSVQTTATFTSMDTSQLPGNSVFKECMKQKKKEFSSG
K, (SEQ ID NO: 62)
CQKQAHHSNVLQTSVQTTATFTSMDTSQLPGNSVFKECMKQKKKEFSSGK, (SEQ ID NO: 63)
QKQAHHSNVLQTSVQTTATFTSMDTSQLPGNSVFKECMKQKKKEFSSGK, (SEQ ID NO: 64)
KQAHHSNVLQTSVQTTATFTSMDTSQLPGNSVFKECMKQKKKEFSSGK, (SEQ ID NO: 65)
QAHHSNVLQTSVQTTATFTSMDTSQLPGNSVFKECMKQKKKEFSSGK, (SEQ ID NO: 66)
AHHSNVLQTSVQTTATFTSMDTSQLPGNSVFKECMKQKKKEFSSGK, (SEQ ID NO: 67)
HHSNVLQTSVQTTATFTSMDTSQLPGNSVFKECMKQKKKEFSSGK, (SEQ ID NO: 68)
HSNVLQTSVQTTATFTSMDTSQLPGNSVFKECMKQKKKEFSSGK, (SEQ ID NO: 69)
SNVLQTSVQTTATFTSMDTSQLPGNSVFKECMKQKKKEFSSGK, (SEQ ID NO: 70)
NVLQTSVQTTATFTSMDTSQLPGNSVFKECMKQKKKEFSSGK, (SEQ ID NO: 71)
VLQTSVQTTATFTSMDTSQLPGNSVFKECMKQKKKEFSSGK, (SEQ ID NO: 72)
LQTSVQTTATFTSMDTSQLPGNSVFKECMKQKKKEFSSGK, (SEQ ID NO: 73)
QTSVQTTATFTSMDTSQLPGNSVFKECMKQKKKEFSSGK, (SEQ ID NO: 74)
TSVQTTATFTSMDTSQLPGNSVFKECMKQKKKEFSSGK, (SEQ ID NO: 75)
SVQTTATFTSMDTSQLPGNSVFKECMKQKKKEFSSGK, (SEQ ID NO: 76)
VQTTATFTSMDTSQLPGNSVFKECMKQKKKEFSSGK, (SEQ ID NO: 77)
QTTATFTSMDTSQLPGNSVFKECMKQKKKEFSSGK, (SEQ ID NO: 78)
TTATFTSMDTSQLPGNSVFKECMKQKKKEFSSGK, (SEQ ID NO: 79)
GNSVFKECMKQKKKEFSSGK, (SEQ ID NO: 80)
NSVFKECMKQKKKEFSSGK, (SEQ ID NO: 81)
SVFKECMKQKKKEFSSGK, (SEQ ID NO: 82)
VFKECMKQKKKEFSSGK, (SEQ ID NO: 83)
FKECMKQKKKEFSSGK, (SEQ ID NO: 84)
KECMKQKKKEFSSGK, (SEQ ID NO: 85)
ECMKQKKKEFSSGK, (SEQ ID NO: 86)
CMKQKKKEFSSGK, (SEQ ID NO: 87)
MKQKKKEFSSGK, (SEQ ID NO: 88)
KQKKKEFSSGK, (SEQ ID NO: 89)
QKKKEFSSGK, (SEQ ID NO: 90)
KKKEFSSGK, (SEQ ID NO: 91)
KKEFSSGK, (SEQ ID NO: 92)
KEFSSGK, (SEQ ID NO: 93)
EFSSGK,
and (SEQ ID NO: 94)
FSSGK.
```

8. A pharmaceutical composition comprising a PAC1 receptor agonist of claim 7 in a pharmaceutically acceptable carrier.

9. A method of downregulating appetite in a mammal, said method comprising administering to said mammal an effective amount of one or more PAC1 receptor agonists of claim 1.

10. The method of claim 9, wherein said one or more PAC1 receptor agonists are administered in conjunction with one or more dipeptidyl peptidase-IV (DPP-IV) inhibitors.

11. The method of claim 9, wherein said mammal is a human.

12. A method of reducing obesity and/or reducing body weight in a mammal, said method comprising administering to said mammal an effective amount of one or more PAC1 receptor agonists of claim 1.

13. A method of slowing the progression of nonalcoholic fatty liver disease (NAFLD), and/or nonalcoholic steatohepatitis (NASH) in a mammal, said method comprising administering to said mammal an effective amount of one or more PAC1 receptor agonists of claim 1.

14. A method of downregulating appetite in a mammal, said method comprising administering to said mammal an effective amount of one or more PAC1 receptor agonists of claim 7.

15. A method of reducing obesity and/or reducing body weight in a mammal, said method comprising administering to said mammal an effective amount of one or more PAC1 receptor agonists of claim 7.

16. A method of slowing the progression of nonalcoholic fatty liver disease (NAFLD), and/or nonalcoholic steatohepatitis (NASH) in a mammal, said method comprising administering to said mammal an effective amount of one or more PAC1 receptor agonists of claim 7.

* * * * *